(12) United States Patent
Venkatesan et al.

(10) Patent No.: US 7,276,603 B2
(45) Date of Patent: Oct. 2, 2007

(54) BENZOFURANYL-AND BENZOTHIENYL-PIPERAZINYL QUINOLINES AND METHODS OF THEIR USE

(75) Inventors: Aranapakam Mudumbai Venkatesan, Regopark, NY (US); Osvaldo Dos Santos, Kew Garden, NY (US); Magda Asselin, Mahwah, NJ (US); George Theodore Grosu, Pearl River, NY (US); Deborah A. Evrard, Hamilton Square, NJ (US); Richard Eric Mewshaw, King of Prussia, PA (US); Kristin Meagher, Novi, MI (US)

(73) Assignee: Wyeth, Madison, NJ (US)

( * ) Notice: Subject to any disclaimer, the term of this patent is extended or adjusted under 35 U.S.C. 154(b) by 213 days.

(21) Appl. No.: 10/835,185

(22) Filed: Apr. 29, 2004

(65) Prior Publication Data

US 2005/0059673 A1    Mar. 17, 2005

Related U.S. Application Data

(60) Provisional application No. 60/467,368, filed on May 2, 2003.

(51) Int. Cl.
  C07D 405/12   (2006.01)
  C07D 409/12   (2006.01)
  A61K 31/496   (2006.01)
(52) U.S. Cl. .................. 544/363; 514/253.06
(58) Field of Classification Search ............... 544/363; 514/253.06
   See application file for complete search history.

(56) References Cited

U.S. PATENT DOCUMENTS 6,313,126 B1   11/2001   Mewshaw et al. .......... 514/249

FOREIGN PATENT DOCUMENTS

| EP | 0 376 607 A1 | 7/1990 |
|---|---|---|
| EP | 0 546 583 A1 | 6/1993 |
| EP | 0 666 258 A1 | 8/1995 |
| EP | 1 092 715 A2 | 4/2001 |
| WO | WO99/51592 A1 | 10/1999 |
| WO | WO99/55695 A1 | 11/1999 |
| WO | WO99/67237 A1 | 12/1999 |
| WO | WO 00/34263 A1 | 6/2000 |
| WO | WO 00/40554 A1 | 7/2000 |
| WO | WO 00/43382 A1 | 7/2000 |
| WO | WO 01/14330 A2 | 3/2001 |
| WO | WO 02/44170 A2 | 6/2002 |

OTHER PUBLICATIONS

Wolff, Manfred E. Burger's Medicinal Chemistry, 5th Ed. Part 1, pp. 975-977 (1995).*
Banker et al. "Modern Pharmaceutics", 3rd Ed. p. 596 (1996).*
Arborelius, L. et al., "HT$_{1A}$ receptor antagonists increase the activity of serotonergic cells in the dorsal raphe nucleus in rats treated acutely or chronically with citalopram," Naunyn-Schmiedeberg's Arch. Pharmacol. 1995, 352: 157-165.

Invernizzi, R. et al., "Chronic treatment with citalopram facilitates the effect of a challenge dose on cortical serotonin output: role of presynaptic 5-HT$_{1A}$ receptors," Eur. J. Pharmacol. 1994, 260: 243-246.
Artigas, F. et al., "Acceleration of the effect of selected antidepressant drugs in major depression by 5-HT$_{1A}$ antagonists," Trends Neurosci. 1996, 19(9): 378-383.
Jean-Luc Malleron et al., "New Indole Derivatives as Potent and Selective Serotonin Uptake Inhibitors," J. Med. Chem. 1993, 36: 1194-1202 [plus erratum: p. 2242].
Wustrow et al., "3-[[(4-Aryl-1-piperazinyl)alkyl]cyclohexyl]-1H-indoles as Dopamine D2 Partial Agonists and Autoreceptor Agonists," J. Med. Chem. 1997, 40: 250-259.
Perez, V., et al., "Randomised double-blind, placebo-controlled trial of pindolol in combination with fluoxetine antidepressant treatment," The Lancet, 1997, 349: 1594-1597.
Feiger, A., "A Double-Blind Comparison of Gepirone Extended Release, Imipramine, and Placebo in the Treatment of Outpatient Major Depression," Psychopharmacol. Bull., 1996, 32(4): 659-665.
Wilcox, C. et al., "A Double-Blind Trial of Low- and High-Dose Ranges of Gepirone-ER Compared With Placebo in the Treatment of Depressed Outpatients," Psychopharmacol. Bull., 1996, 32(3): 335-342.
Grof, P. et al., "An open study of oral flesinoxan, a 5-HT$_{1A}$ receptor agonist, in treatment-resistant depression," International Clinical Psychopharmacology, 1993, 8: 167-172.
Dimitriou, E. et al., "Buspirone Augmentation of Antidepressant Therapy," J. Clinical Psychopharmacol., 1998, 18(6): 465-469.
Krogsgaard-Larsen, et al., (ed.), Design and Application of Prodrugs, Textbook of Drug Design and Development, Chapter 5, 113-191 (1991).
Bundgaard, H. et al., "Prodrugs as a means to improve the delivery of peptide drugs," Advanced Drug Delivery Reviews, Elsevier Science Publishers, 8:1-38 (1992).
Bundgaard, J. et al., "Glycolamide Esters as Biolabile Prodrugs of Carboxylic Acid Agents: Synthesis, Stability, Bioconversion, and Physicochemical Properties," Journal of Pharmaceutical Sciences, 77(4):285-298 (Apr. 1988).

(Continued)

Primary Examiner—Emily Bernhardt
(74) Attorney, Agent, or Firm—Woodcock Washburn LLP

(57) ABSTRACT

Benzofuranyl- and benzothienyl-piperzinyl quinoline derivatives and compositions containing such compounds are disclosed. Methods of using benzofuranyl- and benzothienyl-piperzinyl quinoline derivatives and compositions containing such composition in the treatment and/or prevention of serotonin-related disorders, such as depression and anxiety, are also disclosed. In addition, processes for the preparation of benzofuranyl- and benzothienyl-piperzinyl quinoline derivatives are disclosed. Benzofuranyl- and benzothienyl-piperzinyl quinoline derivatives of Formula I are disclosed:

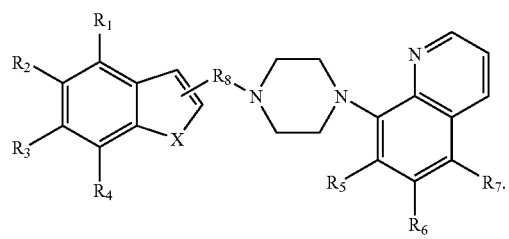

1 Claim, No Drawings

OTHER PUBLICATIONS

Cheetham, S. C. et al., "[$^3$H]Paroxetine Binding in Rat Frontal Cortex Strongly Correlates With [$^3$H]5-HT Uptake: Effect of Administration of Various Antidepressant Treatments," *Neuropharmacol.*, 1993, 32: 737-743.

Cheng, Y-C. et al., "Relationship between the inhibition constant ($K_1$) and the concentration of inhibitor which causes 50 per cent inhibition ($I_{50}$) of an enzymatic reaction," *Biochem. Pharmacol.*, 1973, 22: 3099-3108.

Hall, M. D. et al. "[$^3$H]8-Hydroxy-2-(Di-n-Propylamino)Tetralin Binding to Pre- and Postsynaptic 5-Hydroxytryptamine Sites in Various Regions of the Rat Brain," *J. Neurochem.*, 1985, 44(6): 1685-1696.

Lazareno, S. and Birdsall, N.J.M., "Pharmacological characterization of acetylcholine-stimulated [$^{35}$S]-GTPγS binding mediated by human muscarinic m1-m4 receptors: antagonist studies," *Br. J. Pharmacol.*, 1993, 109:1120-1127.

Burkamp, F. et al., "Preparation of 3-Aminoalkylbenzo[*b*]thiophenes," *Journal of Heterocyclic Chemistry*, Nov.-Dec. 2002, 39(6): 1177-1187.

Orús, L. et al., "Synthesis and Molecular Modeling of New 1-Aryl-3-[4-arylpiperazin-1-yl]-1-propane Derivatives with High Affinity at the Serotonin Transporter and at 5-HT$_{1A}$ Receptors," *J Med Chem*, 2002, 45(19): 4128-4139.

\* cited by examiner

BENZOFURANYL- AND BENZOTHIENYL-PIPERAZINYL QUINOLINES AND METHODS OF THEIR USE

CROSS REFERENCE TO RELATED APPLICATIONS

The present application claims benefit of Provisional Application Ser. No. 60/467,368, filed May 2, 2003, the disclosure of which is hereby incorporated by reference in its entirety.

FIELD OF THE INVENTION

The present invention relates to benzofuranyl- or benzothienyl-piperazinyl quinoline derivatives and, in particular, to their activity both as serotonin reuptake inhibitors and as $5\text{-HT}_{1A}$ receptor antagonists, and to their related use for, inter alia, the treatment and/or prevention of serotonin-related disorders.

BACKGROUND OF THE INVENTION

Major depressive disorder affects an estimated 340 million people worldwide. Depression is the most frequently diagnosed psychiatric disorder and, according to the World Health Organization, is the fourth greatest public health problem. If left untreated, the effects of depression can be devastating, robbing people of the energy or motivation to perform everyday activities and, in some cases, leading to suicide. Symptoms of the disorder include feelings of sadness or emptiness, lack of interest or pleasure in nearly all activities, and feelings of worthlessness or inappropriate guilt. In addition to the personal costs of depression, the disorder also has been estimated to result in more than $40 billion in annual costs in the United States alone, due to premature death, lost productivity, and absenteeism.

Pharmaceuticals that enhance serotonergic neurotransmission have had success in preventing and/or treating many psychiatric disorders, including depression and anxiety. The first generation of non-selective serotonin-affecting drugs operated through a variety of physiological functions that endowed them with several side-effect liabilities. A class of more recently-developed drugs, selective serotonin reuptake inhibitors (SSRIs), have had significant success in preventing and/or treating depression and related illnesses and have become among the most prescribed drugs since the 1980s. Although they have a favorable side effect profile compared to tricyclic antidepressants (TCAs), they have their own particular set of side effects due to the non-selective stimulation of serotonergic sites. They typically have a slow onset of action, often taking several weeks to produce their full therapeutic effect. Furthermore, they have generally been found to be effective in less than two-thirds of patients.

SSRIs are believed to work by blocking the neuronal reuptake of serotonin, increasing the concentration of serotonin in the synaptic space, thus increasing the activation of postsynaptic serotonin receptors. Although a single dose of an SSRI can inhibit the neuronal serotonin transporter, and thus would be expected to increase synaptic serotonin, long-term treatment is usually required before clinical improvement is achieved. It has been suggested that the delay in onset of antidepressant action of the SSRIs is the result of an increase in serotonin levels in the vicinity of the serotonergic cell bodies. This excess serotonin is believed to activate somatodendritic autoreceptors, i.e., $5\text{-HT}_{1A}$ receptors, reduce cell firing activity, and, in turn, decrease serotonin release in major forebrain areas. This negative feedback limits the increment of synaptic serotonin that can be induced by antidepressants acutely. Over time, the somatodendritic autoreceptors become desensitized, allowing the full effect of the SSRIs to be expressed in the forebrain. This time period has been found to correspond to the latency for the onset of antidepressant activity. [Perez, et al., The Lancet, 1997, 349:1594-1597].

In contrast to the SSRIs, a $5\text{-HT}_{1A}$ agonist or partial agonist acts directly on postsynaptic serotonin receptors to increase serotonergic neurotransmission during the latency period for the SSRI effect. Accordingly, the $5\text{-HT}_{1A}$ partial agonists buspirone and gepirone [Feiger, A., Psychopharmacol. Bull., 1996, 32: 659-665, Wilcox, C., Psychopharmacol. Bull., 1996, 32: 335-342], and the $5\text{-HT}_{1A}$ agonist flesinoxan [Grof, P., International Clinical Psychopharmacology, 1993, 8: 167-172], have shown efficacy in clinical trials for the treatment of depression. Furthermore, such agents are believed to stimulate the somatodendritic autoreceptors, thus hastening their desensitization and decreasing the SSRI latency period. Indeed, buspirone augmentation to standard SSRI therapy has been shown to produce marked clinical improvement in patients initially unresponsive to standard antidepressant therapy [Dimitriou, E., J. Clinical Psychopharmacol., 1998, 18: 465-469].

There is still an unfulfilled need for a single agent with a dual mechanism of antidepressant action, i.e., one that not only inhibits or blocks serotonin reuptake (to increase levels of serotonin in the synapse) but also antagonizes the $5\text{-HT}_{1A}$ receptors (to reduce the latency period). The present invention is directed to these, as well as other important ends.

SUMMARY OF THE INVENTION

The present invention relates to benzofuranyl- or benzothienyl-piperazinyl quinoline derivatives and, more particularly, to methods of their use in the treatment and/or prevention of serotonin-related disorders, such as depression, anxiety, cognitive deficits, such as those resulting from Alzheimer's disease and other neurodegenerative disorders, schizophrenia, and prostate cancer. Preferred compounds have the ability to bind and antagonize $5\text{-HT}_{1A}$ receptors, as well as being serotonin reuptake inhibitors.

In one aspect, the present invention provides benzofurynyl- and benzothienyl-piperazino quinoline derivatives of formula I:

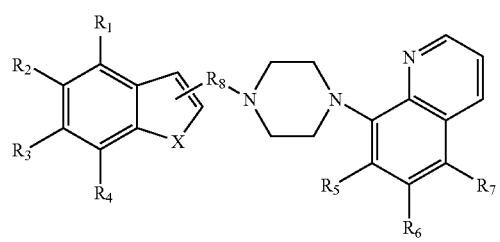

or a prodrug, stereoisomer, N-oxide or pharmaceutically-acceptable salt thereof;
wherein:
X is O or S;
$R_1$, $R_2$, $R_3$, $R_4$, $R_5$, $R_6$, and $R_7$ are independently hydrogen, halo, cyano, —N($R_9$)($R_9$), hydroxy, C(=O)O$R_{10}$, alkyl, alkenyl, alkynyl, aryl, heteroaryl, alkoxy, alkenyloxy, alkynyloxy, aryloxy, heteroaryloxy, perfluoroalkyl, $(R_9)(R_9)$N-alkoxy, $(R_9)(R_9)$N-alkoxyaryl, $S(O)_q$-alkyl where q is 0-2, $S(O)_q$-aryl where q is 0-2, $CONR_{11}R_{12}$, guanidino, cyclic guanidino, alkylaryl, arylalkyl, alkylheteroaryl, heteroarylalkyl, heterocycle, arylalkenyl, —$SO_2NR_{11}R_{12}$, aryloxyaryl, arylalkoxyalkyl, aryloxyalkyl, aryloxyheteroaryl, heteroaryloxyaryl, alkylaryloxyaryl, alkylaryloxyheteroaryl, heteroaryloxyalkyl, or where any two of said $R_1$, $R_2$, $R_3$, $R_4$, $R_5$, $R_6$ or $R_7$ located on adjacent carbon atoms together form an alkylene dioxy group;

$R_8$ is a linker selected from cycloalkyl, alkyl optionally substituted with one or two $R_{13}$, and a moiety of formula:

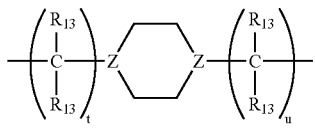

where
Z is N or CH;
t is an integer from 1 to 3; and
u is an integer from 0 to 3;

$R_9$ is hydrogen, alkyl, aryl, heteroaryl, aryloxy, heterocycle, cycloalkyl, alkenyl with the proviso that the double bond of the alkenyl is not present at the carbon atom that is directly linked to N, alkynyl with the proviso that the triple bond of the alkynyl is not present at the carbon atom that is directly linked to N, perfluoroalkyl, —$S(O)_2$alkyl, —$S(O)_2$aryl, —$S(O)_2$aheteroaryl, —(C=O)heteroaryl, —(C=O)aryl, —(C=O)($C_1$-$C_6$) alkyl, —(C=O)cycloalkyl, —(C=O)heterocycle, alkyl-heterocycle, arylalkenyl, —$CONR_{11}R_{12}$, —$SO_2NR_{11}R_{12}$, arylalkoxyalkyl, arylalkylalkoxy, heteroarylalkylalkoxy, aryloxyalkyl, heteroaryloxyalkyl, aryloxyaryl, aryloxyheteroaryl, alkylaryloxyaryl, alkylaryloxyheteroaryl, alkylaryloxyalkyamine, alkoxycarbonyl, aryloxycarbonyl, or heteroaryloxycarbonyl;

$R_{10}$ is hydrogen, alkyl, aryl, heteroaryl, alkylaryl, arylalkyl, heteroarylalkyl, or alkylheteroaryl;

$R_{11}$ and $R_{12}$ are independently hydrogen, alkyl, aryl, heteroaryl, alkylaryl, arylalkyl, heteroarylalkyl, or alkylheteroaryl; and each $R_{13}$ is hydrogen, alkyl, aryl, heteroaryl, alkylaryl, arylalkyl, heteroarylalkyl, alkyl heteroaryl, or —$N(R_9)(R_9)$.

In another aspect, the present invention is directed to compositions comprising a compound of formula I and one or more pharmaceutically-acceptable carriers.

In another aspect, the present invention is directed to methods of treating and/or preventing a patient suspected to suffer from a serotonin-related disorder, comprising the step of administering to the patient a therapeutically effective amount of a compound of formula I.

In yet another aspect, the present invention describes methods of antagonizing 5-$HT_{1A}$ receptors in a patient in need thereof, comprising the step of administering to the patient a therapeutically effective amount of a compound of formula I.

The present invention is also directed to methods of inhibiting the reuptake of in a patient in need thereof, comprising the step of administering to the patient a therapeutically effective amount of a compound of formula I.

In another aspect, this invention is drawn to processes for the preparation of benzofuranyl- and benzothienyl-piperzinyl quinoline derivatives, comprising the step of reacting a compound of formula II:

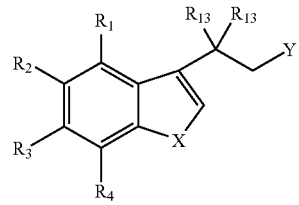

with a compound of formula III:

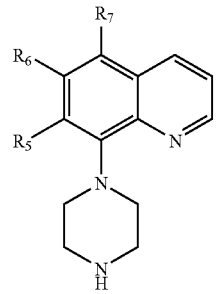

in the presence of at least one aprotic polar solvent and at least one acid binding agent.

As 5-$HT_{1A}$ antagonists, the novel compounds are useful for the treatment and/or prevention of several diseases and disorders, including anxiety, depression, cognitive deficits, such as those resulting from Alzheimer's disease and other neurodegenerative disorders, schizophrenia, and prostate cancer. They are also useful as co-administered therapeutic agents to enhance the onset of the antidepressant action of SSRIs and for relief of the symptoms resulting from nicotine withdrawal.

DETAILED DESCRIPTION OF THE INVENTION

The term "alkyl", as used herein, whether used alone or as part of another group, refers to a substituted or unsubstituted aliphatic hydrocarbon chain attached via a $sp^3$ hybridized carbon atom, and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain attached via a $sp^2$ hybridized carbon atom, and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. Specifically included within the definition of "alkenyl" are those aliphatic hydrocarbon chains that are optionally substituted. Heteroatoms, such as O, S or N—$R_1$, attached to an alkenyl should not be attached to a carbon atom that is bonded to a double bond.

The term "alkynyl", as used herein, whether used alone or as part of another group, refers to a substituted or unsubstituted aliphatic hydrocarbon chain attached via a sp hybridized carbon atom, and includes, but is not limited to, straight and branched chains having 2 to 6 carbon atoms and containing at least one triple bond. Preferably, the alkynyl moiety has 3 to 6 carbon atoms. In certain embodiments, the alkynyl may contain more than one triple bond and, in such cases, the alknyl group must contain at least three carbon atoms. Specifically included within the definition of "alkynyl" are those aliphatic hydrocarbon chains that are optionally substituted. Heteroatoms, such as O, S or N—$R_1$, attached to an alkynyl should not be attached to the carbon that is bonded to a triple bond.

The term "cycloalkyl", as used herein, whether used alone or as part of another group, refers to a substituted or unsubstituted alicyclic hydrocarbon group having 3 to 7 carbon atoms. Specifically included within the definition of "cycloalkyl" are those alicyclic hydrocarbon groups that are optionally substituted.

The term "aryl", as used herein, whether used alone or as part of another group, is defined as a substituted or unsubstituted aromatic hydrocarbon ring group and includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted.

The term "heteroaryl", as used herein, whether used alone or as part of another group, is defined as a substituted or unsubstituted aromatic heterocyclic ring system (monocyclic or bicyclic) where the heteroaryl moiety is:

(1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline;
(2) a bicyclic aromatic heterocycle where a phenyl, pyridine, pyrimidine or pyridizine ring is:
  (a) fused to a 6-membered aromatic (unsaturated) heterocyclic ring having one nitrogen atom;
  (b) fused to a 5- or 6-membered aromatic (unsaturated) heterocyclic ring having two nitrogen atoms;
  (c) fused to a 5-membered aromatic (unsaturated) heterocyclic ring having one nitrogen atom together with either one oxygen or one sulfur atom; or
  (d) fused to a 5-membered aromatic (unsaturated) heterocyclic ring having one heteroatom selected from O, N or S.

Specifically included within the definition of "heteroaryl" are those aromatic heterocyclic rings that are optionally substituted. An optionally substituted heteroaryl may be substituted with 1 or 2 substituents.

An optionally substituted alkyl, alkenyl, alkynyl, cycloalkyl, aryl and heteroaryl may be substituted with one or two substituents. Suitable optionally substituents may be selected independently from nitro, cyano, —N($R_{11}$)($R_{12}$), halo, hydroxy, carboxy, alkyl, alkenyl, alkynyl, cycloalkyl, aryl, heteroaryl, alkoxy, aryloxy, heteroaryloxy, alkylalkoxy, alkoxycarbonyl, alkoxyalkoxy, perfluoroalkyl, perfluoroalkoxy, arylalkyl, alkylaryl, hydroxyalkyl, alkoxyalkyl, alkylthio, —S(O)$_2$—N($R_{11}$)($R_{12}$), —C(=O)—N($R_{11}$)($R_{12}$), ($R_{11}$)($R_{12}$)N-alkyl, ($R_{11}$)($R_{12}$)N-alkoxyalkyl, ($R_{11}$)($R_{12}$)N-alkylaryloxyalkyl, —S(O)$_s$-aryl (where s=0-2) or —S(O)$_s$-heteroaryl (where s=0-2). In certain embodiments of the invention, preferred substitutents for alkyl, alkenyl, alkynyl and cycloalkyl include nitro, cyano, —N($R_{11}$)($R_{12}$), halo, hydroxyl, aryl, heteroaryl, alkoxy, alkoxyalkyl, and alkoxycarbonyl. In certain embodiments of the invention, preferred substituents for aryl and heteroaryl include —N($R_{11}$)($R_{12}$), alkyl, halo, perfluoroalkyl, perfluoroalkoxy, arylalkyl and alkylaryl.

The term "alkoxy", as used herein, whether used alone or as part of another group, refers to the group $R_a$—O—, where $R_a$ is an alkyl group, as defined above.

The term "alkenyloxy", as used herein, whether used alone or as part of another group, refers to the group $R_e$—O—, where $R_e$ is an alkenyl group as defined above.

The term "alkynyloxy", as used herein, whether used alone or as part of another group, refers to the group $R_f$—O—, where $R_f$ is an alkynyl group as defined above.

The term "aryloxy", as used herein, whether used alone or as part of another group, refers to the group $R_b$—O—, where $R_b$ is an aryl group, as defined above.

The term "heteroaryloxy", as used herein, whether used alone or as part of another group, refers to the group $R_c$—O—, where $R_c$ is a heteroaryl group, as defined above.

The term "alkylaryl", as used herein, whether used alone or as part of another group, whether used alone or as part of another group, refers to the group —$R_b$—$R_a$, where $R_b$ is an aryl group, as defined above, substituted by $R_a$, an alkyl group as defined above.

The term "heteroarylalkyl", as used herein, whether used alone or as part of another group, refers to the group —$R_a$—$R_c$, where $R_a$ is an alkyl group as defined above, substituted with $R_c$, a heteroaryl group, as defined above. Heteroarylalkyl moieties include, but are not limited to, heteroaryl-(CH$_2$)$_{1-6}$.

The term "arylalkyl", as used herein, whether used alone or as part of another group, refers to the group —$R_a$—$R_b$, where $R_a$ is an alkyl group as defined above, substituted by $R_b$, an aryl group, as defined above. Examples of arylalkyl moieties include, but are not limited to, benzyl, 1-phenylethyl, 2-phenylethyl, 3-phenylpropyl, 2-phenylpropyl and the like.

The term "alkylheteroaryl", as used herein, whether used alone or as part of another group, refers to the group —$R_c$—$R_a$, where $R_c$ is a heteroaryl group as defined above, substituted with $R_a$, an alkyl group as defined above.

The term "arylalkenyl", as used herein, whether used alone or as part of another group, refers to the group —$R_e$—$R_b$, containing a total of 8 to 16 carbon atoms, where $R_b$ is an aryl group, as defined above, and $R_e$ is an alkenyl group as defined above, with the proviso that no heteroatom such as O, S or N—$R_1$ is attached to a carbon atom, which is attached to a double bond.

The term "heterocycle", as used herein, whether used alone or as part of another group, refers to a stable 3 to 8-member ring containing carbons atoms and from 1 to 3 heteroatoms selected from the group consisting of nitrogen, phosphorus, oxygen, and sulfur. A heterocycle of this invention may be either a monocyclic or bicyclic ring system, and may either be saturated or partially saturated. Heterocycle groups include, but are not limited to, aziridinyl, azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "arylalkoxyalkyl", as used herein, whether used alone or as part of another group, refers to the group $R_b$—$R_a$—O—$R_a$—, where $R_b$ is an aryl group, as defined above, and $R_a$ is an alkyl group as defined above.

The term "alkoxyalkyl", as used herein, whether used alone or as part of another group, refers to the group $R_a$—O—$R_a$—, where $R_a$ is an alkyl group as defined above.

The term "aryloxyalkyl", as used herein, whether used alone or as part of another group, refers to the group $R_b$—O—$R_a$—, where $R_b$ is an aryl group, as defined above, and $R_a$ is an alkyl group as defined above.

The term "aryloxyaryl", as used herein, whether used alone or as part of another group, refers to the group $R_b$—O—$R_b$—, where $R_b$ is an aryl group, as defined above.

The term "aryloxyheteroaryl", as used herein, whether used alone or as part of another group, refers to the group $R_b$—O—$R_c$—, where $R_b$ is an aryl group, as defined above, and $R_c$ is a heteroaryl group, as defined above.

The term "alkylaryloxyaryl", as used herein, whether used alone or as part of another group, refers to the group $R_a$—$R_b$—O—$R_b$—, where $R_a$ is an alkyl group as defined above, and $R_b$ is an aryl group, as defined above.

The term "alkoxycarbonyl", as used herein, whether used alone or as part of another group, refers to the group $R_a$—O—C(=O)—, where $R_a$ is an alkyl group as defined above.

The term "aryloxycarbonyl", as used herein, whether used alone or as part of another group, refers to the group $R_b$—O—C(=O)—, where $R_b$ is an aryl group, as defined above.

The term "heteroaryloxycarbonyl", as used herein, whether used alone or as part of another group, refers to the group $R_c$—O—C(=O)—, where $R_c$ is a heteroaryl group, as defined above.

The term "alkoxyalkoxy", as used herein, whether used alone or as part of another group, refers to the group $R_a$—O—$R_a$—O—, where $R_a$ is an alkyl group, as defined above.

The term "alkylene dioxy", as used herein, is defined as

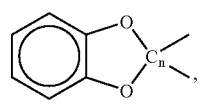

where n=1 or 2 and where the alkylene portion may be substituted with substituents as defined for "alkyl".

The term "heteroaryloxyalkyl", as used herein, whether used alone or as part of another group, refers to the group $R_c$—O—$R_a$—, where $R_c$ is a heteroaryl group, as defined above, and $R_a$ is a alkyl group, as defined above.

The term "heteroaryloxyaryl", as used herein, whether used alone or as part of another group, refers to the group $R_c$—O—$R_b$—, where $R_c$ is a heteroaryl group, as defined above, and $R_b$ is an aryl group, as defined above.

The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "perfluoroalkoxy", as used herein, whether used alone or as part of another group, refers to the group $R_a$—O—, where $R_a$ is a saturated aliphatic hydrocarbon having 1 to 6 carbon atoms and two or more fluorine atoms and includes, but is not limited to, straight or branched chains, such as —$OCF_3$, —$OCH_2CF_3$, —$OCF_2CF_3$ and —$OCH(CF_3)_2$.

The term "halo", as used herein, refers to chloro, bromo, fluoro, or iodo.

The term "guanidino", as used herein, refers to

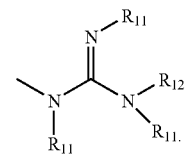

The term "cyclic guanidino", as used herein, refers to

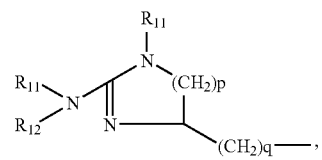

where p is 1 or 2, and q is 0 to 2.

Suitable aprotic polar solvents include, but are not limited to, dimethyl sulfoxide, dimethyl formamide, tetrahydrofuran, acetone and ethanol.

Suitable acid binding agents include, but are not limited to, organic tertiary bases, such as, for example, triethyl amine,triethnaol amine, 1,8-diazabicyclo[5.4.0]undec-7-ene DBU, and diisopropylethylamine; and alkaline metal carbonates, such as, for example, potassium carbonate and sodium carbonates.

It is understood that compounds according to formula I can include asymmetric carbons, and that formula I encompasses all possible stereoisomers and mixtures thereof, as well as racemic modifications, particularly those that possess the activity discussed below. Optical isomers may be obtained in pure form by standard separation techniques.

Preferred among the above noted $R_1$ to $R_7$ groups are alkyl, halo, alkoxy, cyano, alkoxycarbonyl, amido, carboxy, N($R_9$)($R_9$), and C(=O)O$R_{10}$. Particularly preferred are methyl, isopropyl, methoxy, chloro, and fluoro.

Preferred $R_8$ groups are cycloalkyl and $(C_1-C_8)$alkyl optionally substituted with alkyl, aryl, heteroaryl, cycloalkyl, or heterocycle. Particularly preferred are ethyl, propyl, isopropyl, butyl, hexyl and cyclohexyl.

Preferred $R_9$ groups are hydrogen, alkyl, aryl, heteroaryl, heterocycle, cycloalkyl, perfluoroalkyl, —S(O)$_2$alkyl, —S(O)$_2$aryl, —(C=O)aryl, —(C=O)(C$_1$-C$_6$)alkyl, —(C=O)cycloalkyl, —(C=O)heterocycle, —(C=O)NR$_{11}$R$_{12}$, and —SO$_2$NR$_{11}$R$_{12}$. Particularly preferred is alkyl.

Preferred $R_{10}$ groups are hydrogen and alkyl.

Preferred $R_{11}$ and $R_{12}$ are hydrogen, alkyl, alkylaryl, and alkylheteroaryl.

Preferred $R_{13}$ groups are hydrogen and alkyl.

The following compounds are particularly preferred:

8-{4-[2-(1-benzofuran-3-yl)ethyl]-1-piperazinyl}-6-fluoro-quinoline;

8-{4-[2-(1-benzofuran-3-yl)ethyl]-1-piperazinyl}-6-chloro-quinoline;

8-{4-[2-(1-benzofuran-3-yl)ethyl]-1-piperazinyl}-6-methylquinoline;

8-{4-[2-(1-benzofuran-3-yl)ethyl]-1-piperazinyl}-6-methoxyquinoline;

8-{4-[2-(6-chloro-1-benzofuran-3-yl)ethyl]-1-piperazinyl}-quinoline;

8-{4-[2-(6-chloro-1-benzofuran-3-yl)ethyl]-1-piperazinyl}-6-fluoro-quinoline;

8-{4-[2-(6-chloro-1-benzofuran-3-yl)ethyl]-1-piperazinyl}-6-chloro-quinoline;

8-{4-[2-(6-chloro-1-benzofuran-3-yl)ethyl]-1-piperazinyl}-6-methyl-quinoline;

8-{4-[2-(6-methoxy-1-benzofuran-3-yl)ethyl]-1-piperazinyl}-quinoline;

8-{4-[2-(6-methoxy-1-benzofuran-3-yl)ethyl]-1-piperazinyl}-6-methyl-quinoline;

8-{4-[2-(6-methoxy-1-benzofuran-3-yl)ethyl]-1-piperazinyl}-6-chloro-quinoline;

8-{4-[2-(5-chloro-1-benzofuran-3-yl)ethyl]-1-piperazinyl}-quinoline;

8-{4-[2-(5-chloro-1-benzofuran-3-yl)ethyl]-1-piperazinyl}-6-chloro-quinoline;

8-{4-[2-(5-chloro-1-benzofuran-3-yl)ethyl]-1-piperazinyl}-6-methyl-quinoline;

8-{4-[2-(5-fluoro-1-benzofuran-3-yl)ethyl]-1-piperazinyl}-quinoline;

8-{4-[2-(5-fluoro-1-benzofuran-3-yl)ethyl]-1-piperazinyl}-6-methoxyy-quinoline;

8-{4-[2-(5-fluoro-1-benzofuran-3-yl)ethyl]-1-piperazinyl}-6-fluoro-quinoline;

8-{4-[2-(7-methoxy-1-benzofuran-3-yl)ethyl]-1-piperazinyl}-quinoline;

8-{4-[2-(7-methoxy-1-benzofuran-3-yl)ethyl]-1-piperazinyl}-6-methoxy-quinoline;

8-{4-[2-(7-methoxy-1-benzofuran-3-yl)ethyl]-1-piperazinyl}-6-chloro-quinoline;

8-{4-[2-(5-methoxy-1-benzofuran-3-yl)ethyl]-1-piperazinyl}-quinoline;

8-{4-[2-(5-methoxy-1-benzofuran-3-yl)ethyl]-1-piperazinyl}-6-chloro-quinoline;

8-{4-[2-(5-methoxy-1-benzofuran-3-yl)ethyl]-1-piperazinyl}-6-methyl-quinoline;

8-{4-[2-(5-methoxy-1-benzofuran-3-yl)ethyl]-1-piperazinyl}-6-isopropyl-quinoline;

8-{4-[2-(5-methoxy-1-benzofuran-3-yl)ethyl]-1-piperazinyl}-6-methoxy -quinoline;

8-{4-[2-(5-methoxy-1-benzofuran-3-yl)ethyl]-1-piperazinyl}-6-fluoro-quinoline;

8-{4-[2-(1-benzofuran-3-yl)propyl]-1-piperazinyl}quinoline;

8-{4-[2-(1-benzofuran-3-yl)propyl]-1-piperazinyl}-6-chloro-quinoline;

8-{4-[2-(1-benzofuran-3-yl)propyl]-1-piperazinyl}-6-fluoro-quinoline;

8-{4-[2-(1-benzofuran-3-yl)propyl]-1-piperazinyl}-6-methyl-quinoline;

8-{4-[2-(7-methoxy-1-benzofuran-3-yl)propyl]-1-piperazinyl}quinoline;

8-{4-[2-(7-methoxy-1-benzofuran-3-yl)propyl]-1-piperazinyl}-6-methyl-quinoline;

8-{4-[2-(7-methoxy-1-benzofuran-3-yl)propyl]-1-piperazinyl}-6-chloro-quinoline;

8-{4-[2-(7-methoxy-1-benzofuran-3-yl)propyl]-1-piperazinyl}-6-methyl-quinoline;

8-{4-[2-(7-methoxy-1-benzofuran-3-yl)-1-methylethyl)piperazin-1-yl]quinoline;

6-methoxy-8-{4-[2-(7-methoxy-1-benzofuran-3-yl)-1-methylethyl)piperazin-1yl]quinoline;

6-methyl-8-{4-[2-(7-methoxy-1-benzofuran-3-yl)-1-methylethyl)piperazin-1-yl]quinoline;

8-{4-[2-(5-methoxy-1-benzofuran-3-yl)-1-methylethyl)piperazin-1-yl]quinoline;

6-chloro-8-{4-[2-(5-methoxy-1-benzofuran-3-yl)-1-methylethyl)piperazin-1-yl]quinoline;

6-methyl-8-{4-[2-(5-methoxy-1-benzofuran-3-yl)-1-methylethyl)piperazin-1-yl]quinoline;

8-{4-[4-cis-(1-benzothien-3-yl)cyclohexyl]-1-piperazinyl}-6-chloroquinoline;

8-{4-[4-trans(1-benzothien-3-yl)cyclohexyl]-1-piperazinyl}-6-chloroquinoline;

8-{4-[4-cis(1-benzothien-3-yl)cyclohexyl]-1-piperazinyl}-6-fluoroquinoline;

8-{4-[4-trans(1-benzothien-3-yl)cyclohexyl]-1-piperazinyl}-6-fluoroquinoline;

8-{4-[4-cis(1-benzothien-3-yl)cyclohexyl]-1-piperazinyl}-6-methoxyquinoline;

8-{4-[4-trans(1-benzothien-3-yl)cyclohexyl]-1-piperazinyl}-6-methoxyquinoline;

6-fluoro-8-{4-[4-cis(5-fluoro-1-benzothien-3-yl)cyclohexyl]piperazin-1-yl}quinoline;

6-fluoro-8-{4-[4-trans(5-fluoro-1-benzothien-3-yl)cyclohexyl]piperazin-1-yl}quinoline;

6-methoxy-8-{4-[4-cis(5-fluoro-1-benzothien-3-yl)cyclohexyl]piperazin-1-yl}quinoline;

6-methoxy-8-{4-[4-trans(5-fluoro-1-benzothien-3-yl)cyclohexyl]piperazin-1-yl}quinoline;

5-chloro-8-{4-[4-cis(5-fluoro-1-benzothien-3-yl)cyclohexyl]piperazin-1-yl}quinoline;

5-chloro-8-{4-[4-trans(5-fluoro-1-benzothien-3-yl)cyclohexyl]piperazin-1-yl}quinoline;

8-{4-[4-cis(1-benzofuran-3-yl)cyclohexyl]-1-piperazinyl}-5-fluoroquinoline;

8-{4-[4-trans(1-benzofuran-3-yl)cyclohexyl]-1-piperazinyl}-5-fluoroquinoline;

8-{4-[4-cis(1-benzofuran-3-yl)cyclohexyl]-1-piperazinyl}-6-fluoroquinoline;

8-{4-[4-trans(1-benzofuran-3-yl)cyclohexyl]-1-piperazinyl}-6-fluoroquinoline;

5-fluoro-8-{4-[4-cis(7-methoxy-1-benzofuran-3-yl)cyclohexyl]-1-piperazinyl}quinoline;

5-fluoro-8-{4-[4-trans(7-methoxy-1-benzofuran-3-yl)cyclohexyl]-1-piperazinyl}quinoline;

6-fluoro-8-{4-[4-cis(7-methoxy-1-benzofuran-3-yl)cyclohexyl]-1-piperazinyl}quinoline;

6-fluoro-8-{4-[4-trans(7-methoxy-1-benzofuran-3-yl)cyclohexyl]-1-piperazinyl}quinoline;

8-{4-[4-cis(7-methoxy-1-benzofuran-3-yl)cyclohexyl]-1-piperazinyl}quinoline;

8-{4-[4-trans(7-methoxy-1-benzofuran-3-yl)cyclohexyl]-1-piperazinyl}quinoline;

5-chloro-8-{4-[4-cis(7-methoxy-1-benzofuran-3-yl)cyclohexyl]piperazin-1-yl}quinoline;

5-chloro-8-{4-[4-trans(7-methoxy-1-benzofuran-3-yl)cyclohexyl]piperazin-1-yl}quinoline;

5-chloro-8-{4-[4-cis(5-methoxy-1-benzofuran-3-yl)cyclohexyl]piperazin-1-yl}quinoline;

5-chloro-8-{4-[4-trans(5-methoxy-1-benzofuran-3-yl)cyclohexyl]piperazin-1-yl}quinoline;

6-fluoro-8-{4-[4-cis(5-methoxy-1-benzofuran-3-yl)cyclohexyl]piperazin-1-yl}quinoline;

6-fluoro-8-{4-[4-trans(5-methoxy-1-benzofuran-3-yl)cyclohexyl]piperazin-1-yl}quinoline;

8-[4-(4-benzofuran-2-yl-yclohexyl)-piperazin-1-yl]-6-fluoro-quinoline;

cis-8-[4-(4-thiophene-2-yl-cyclohexyl)-piperazin-1-yl]-6-methoxy-quinoline;

trans-8-[4-(4-thiophene-2-yl-cyclohexyl)-piperazin-1-yl]-6-methoxy-quinoline;

8-[4-(4-Benzofuran-2-yl-yclohexyl)-piperazin-1-yl]-6-fluoro-quinoline;

cis-8-[4-(4-thiophene-2-yl-cyclohexyl)-piperazin-1-yl]-6-methoxy-quinoline; or trans-8-[4-(4-thiophene-2-yl-cyclohexyl)-piperazin-1-yl]-6-methoxy-quinoline.

The present invention provides a process for the preparation of a compound of general formula I. These compounds may be prepared by condensing the appropriately substituted 8-piperazino quinoline derivatives 13 with the appropriately substituted heterocycles 14 in solvents such as DMF, THF or DMSO, acetone or ethanol, in the presence of an acid binding agent such as an organic tertiary base, such as triethylamine, triethanolamine, DBU, or diisopropylethylamine, an alkaline metal carbonate such as potassium carbonate or sodium carbonate, at 100-150° C., as illustrated below in Scheme 1. See also, J. March, *Advanced Organic Chemistry, Mechanisms and Structure*, John Wiley and Sons, 4th edition, 1992.

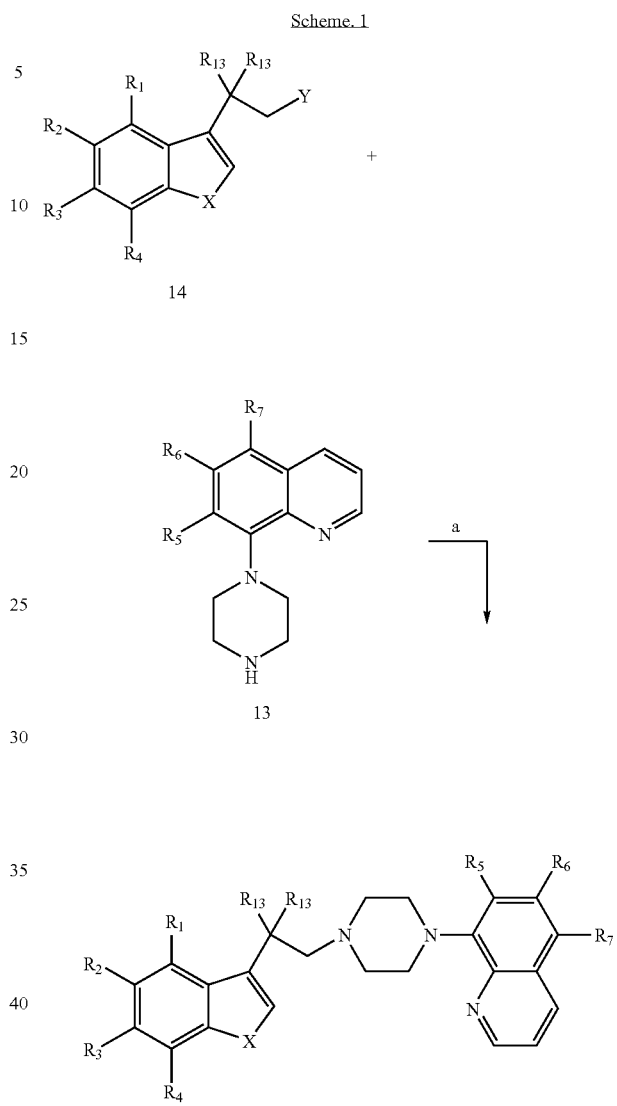

Scheme 1

Y=Halogen, Mesylate or Tosylate: a=DMSO/Diisopropyl ethylamine/120° C.

Alternatively, when the linkers connecting the 8-piperazino quinoline and benzo[1]furan or benzo[1]thiophene are moieties of the following formula:

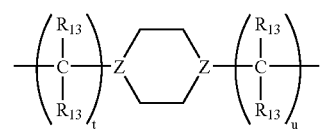

where

Z is N or CH;

t is an integer from 1 to 3; and u is an integer from 1 to 3;

the resultant compounds may be prepared as indicated in Scheme 2, 3 or 4, as illustrated below.

Scheme 2
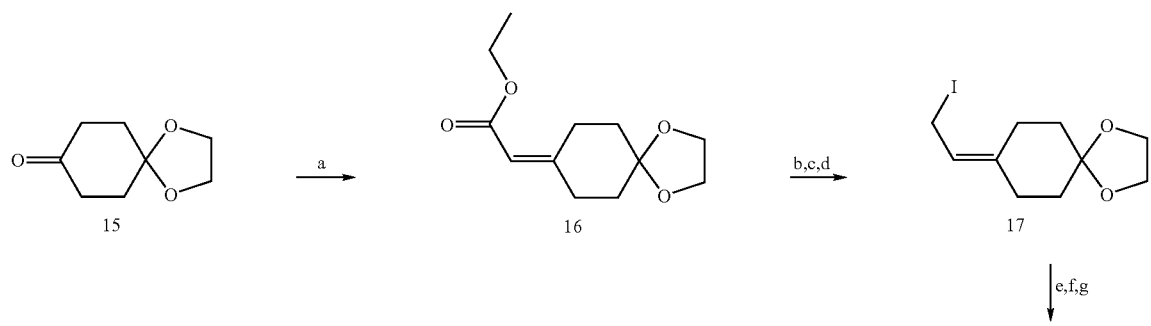
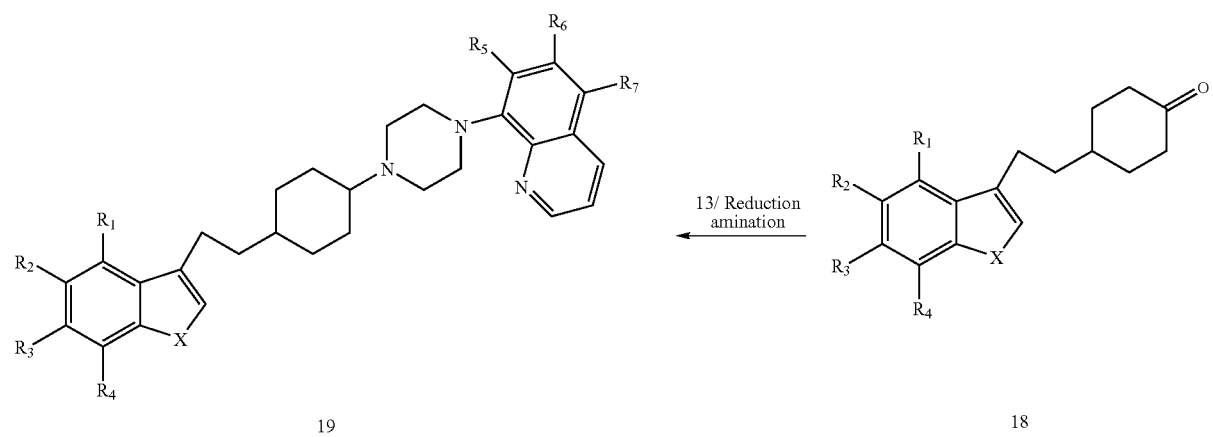
a. Ph₃P=CR₁₃COOEt/Toluene/ Reflux; b. Pt/H₂; c. LiAlH₄/THF; d. Ph₃P/I₂/Imidazole
e. Ph₃P/Base; f. 35/Reflux; g. HCl
Scheme 3
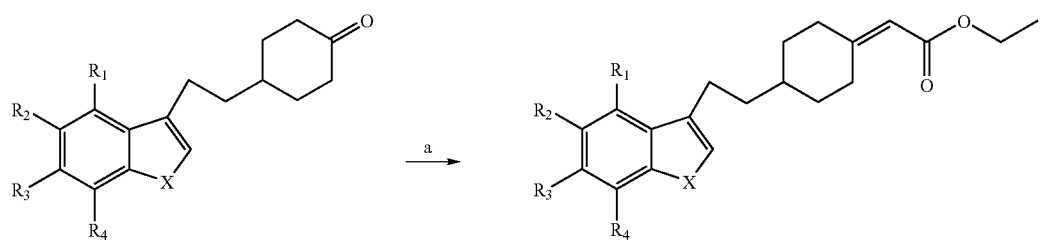

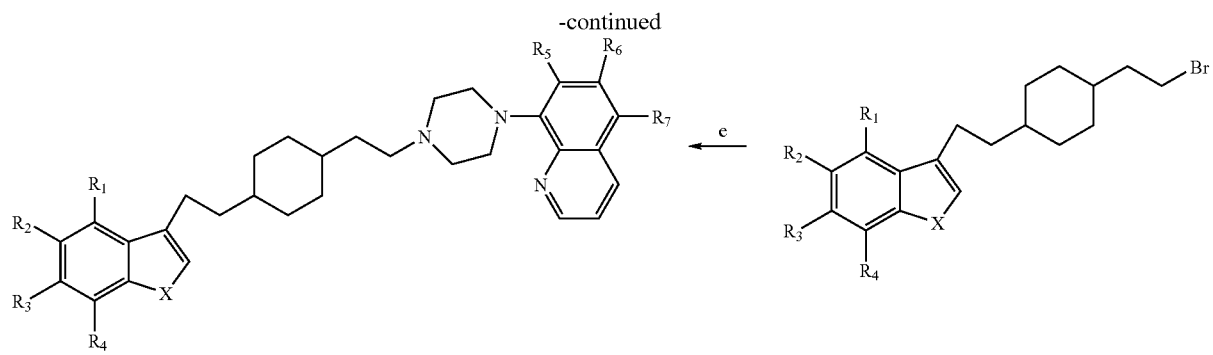
a. Ph₃P=CHCOOEt/ Toluene. Reflux; b. Pt/H₂; c. LiAlH₄/ THF; d. Ph₃P/ CBr₄; e. 13/ Diisopropyl ethyl amine/ DMSO/ 120° C.
Scheme 4
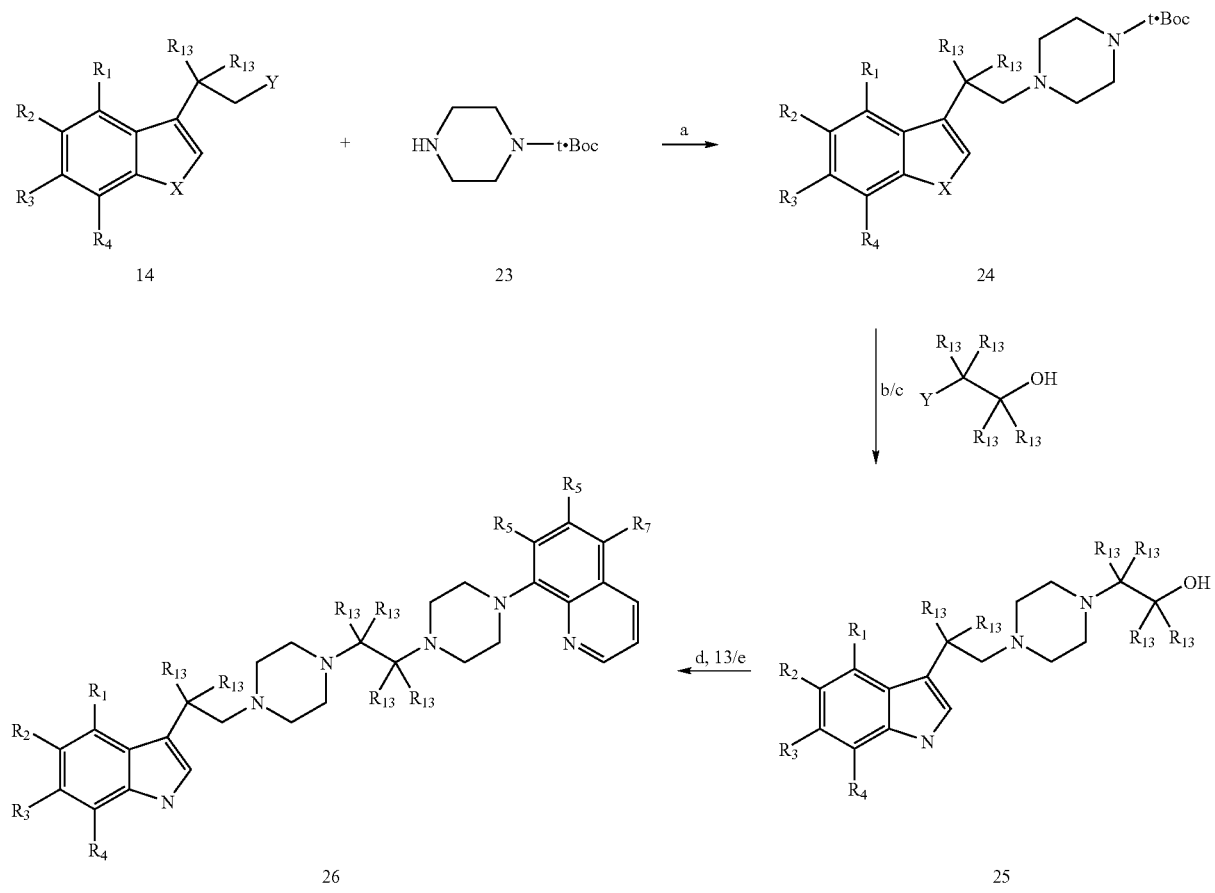
a. DMSO/Diisopropyl ethyl amine; b. HCl/Dioxane; c. DMSO/Diisopropyl ethyl amine; d. Ph₃P/ CBr₄; e. 13/ Diisopropyl ethylamine/ DMSO/ 120° C.
Alternatively, when the linkers connecting the piperazino quinoline and benzo[1]thiophene are
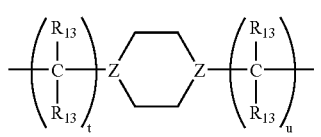

where Z=N or CH, t=1 to 3, u=0, the resultant compounds may be prepared as indicated in Scheme 5, as illustrated below.

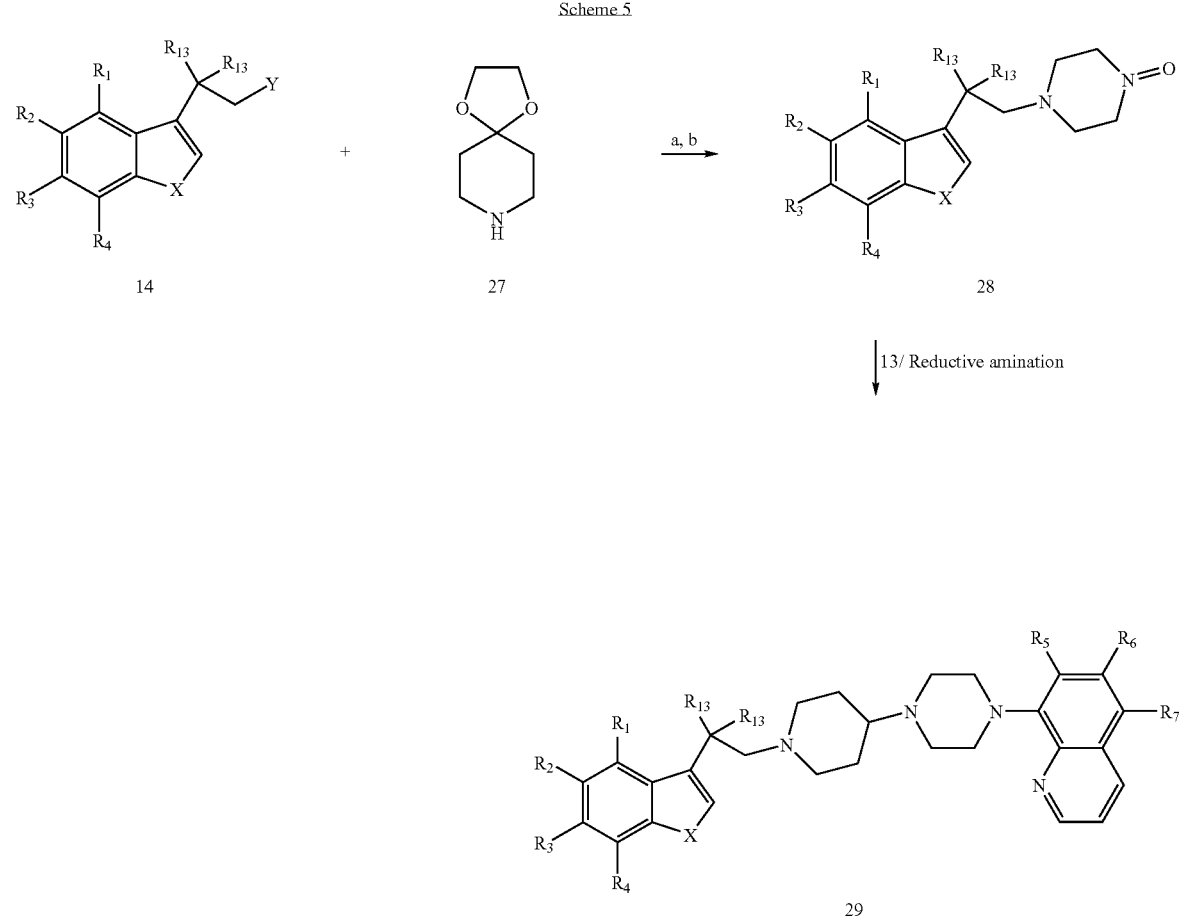

a. DMSO/Diisopropyl ethyl amine; b. HCl/Dioxane

The benzo[1]furan and benzo[1]thiophene 14 may be prepared from the commercially available substituted salicyclic acid derivatives 30, as illustrated below in Scheme 6. Generally, the appropriately substituted salicylic acid derivatives or thiosalicyclic acid derivatives were esterified using the alcoholic hydrochloric acid. Compound 31 was reacted with ethyl bromoacetate in refluxing acetone/ $K_2CO_3$. The resultant diester 32 was hydrolyzed to the diacid 33. The diacid obtained was cyclized using anhydrous $CH_3COONa/(CH_3CO)_2O$ to compound 34. This was hydrolyzed using 1N HCl to produce compound 35. This compound, on reaction with (triphenylphosphoranylidene)ethylacetate or the appropriately substituted (triphenylphosphoranylidene)ethylacetate derivative in boiling organic solvents such as toluene or xylene, yields compound 36. This can be converted to 14 by reduction using LAH and converting it to either tosylate or iodide using $I_2$/imidazole.

Scheme 6
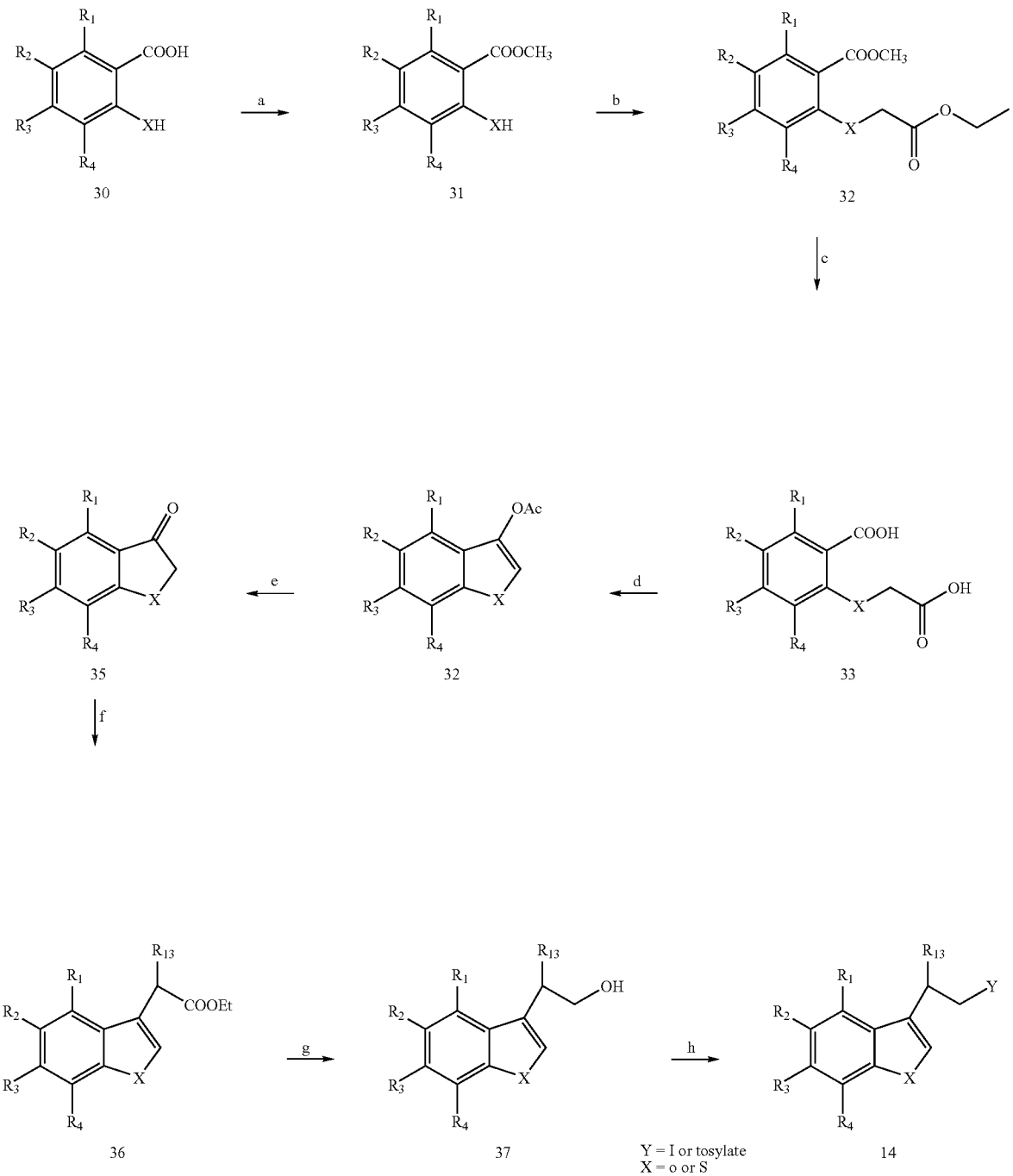
(a) MeOH·HCl/ Reflux; (b) BrCH$_2$COOEt/ K$_2$CO$_3$/ Acetone/ Reflux; (c) NaOH/ EtOH/ THF/ Reflux; (d) (CH$_3$CO)$_2$O/ CH$_3$COONa/ CH$_3$COOH/ reflux; (e) 1N·HCl/ MeOH/ reflux; (f) Ph$_3$P=CHR$_1$COOEt/ Toluene/ Reflux; (g) LAH/ THT/ 0° C.; (h) p-Toluene sulfonyl chloride/ Pyridine or PPh$_3$/ I$_2$/ Imidazole/ THF Alternatively, compound 35 can be reacted with 1-triphenylphosphoranylidene-2-propanone to yield 38, which can be reacted with 8-piperazinoquinoline derivatives 13 using sodium triacetoxyborohydride to give 39, as illustrated in Scheme 7. How ever, when the linker is (R$_8$) cycloalkyl, these class of compounds can be prepared by the methods as indicated in Scheme 8 and Scheme 9.

-continued

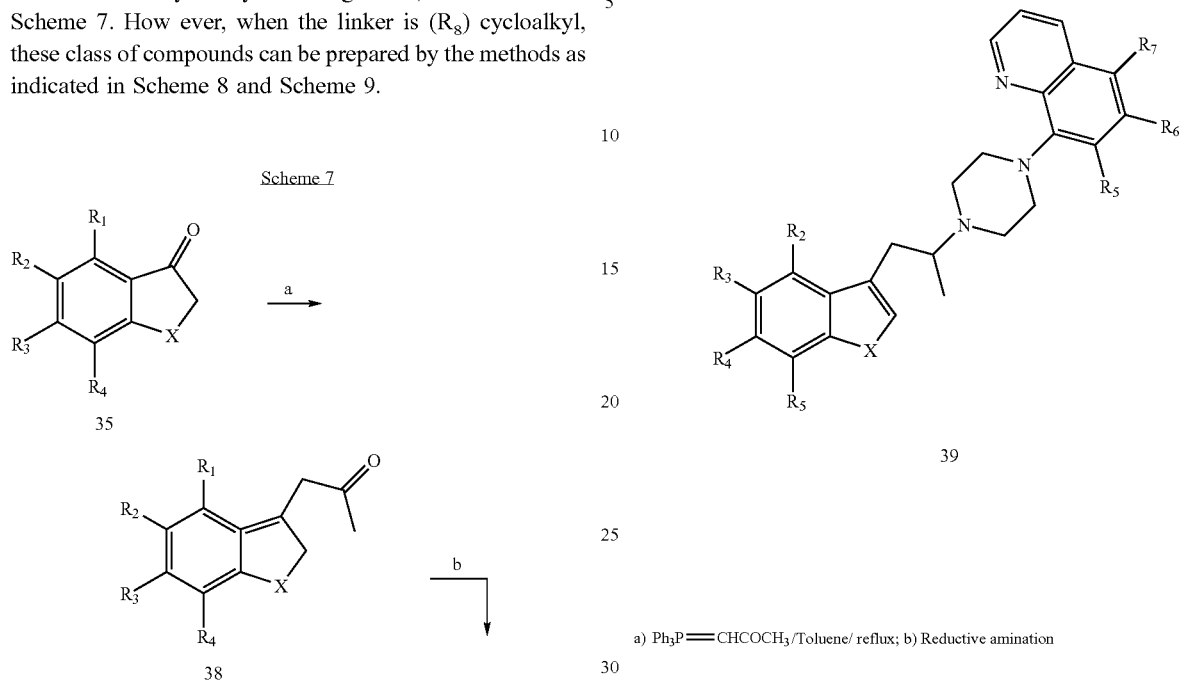

a) Ph$_3$P=CHCOCH$_3$/Toluene/ reflux; b) Reductive amination

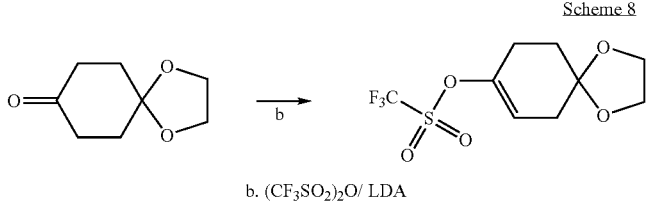

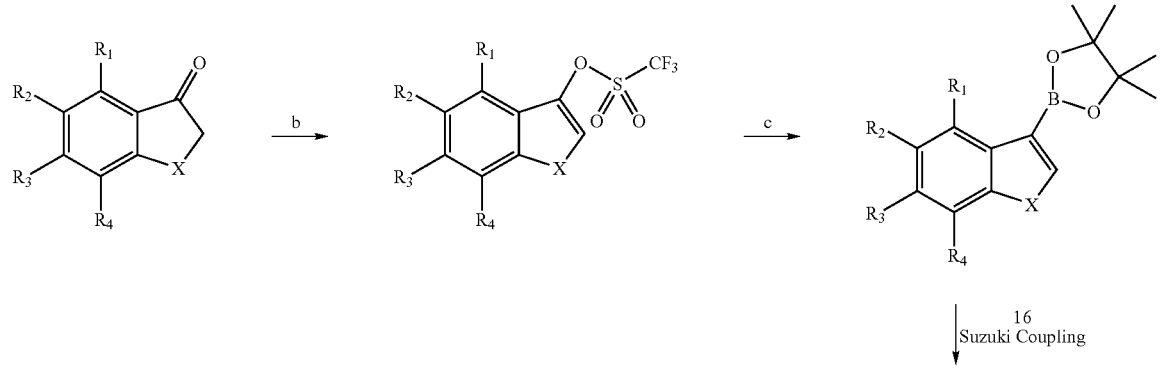

-continued
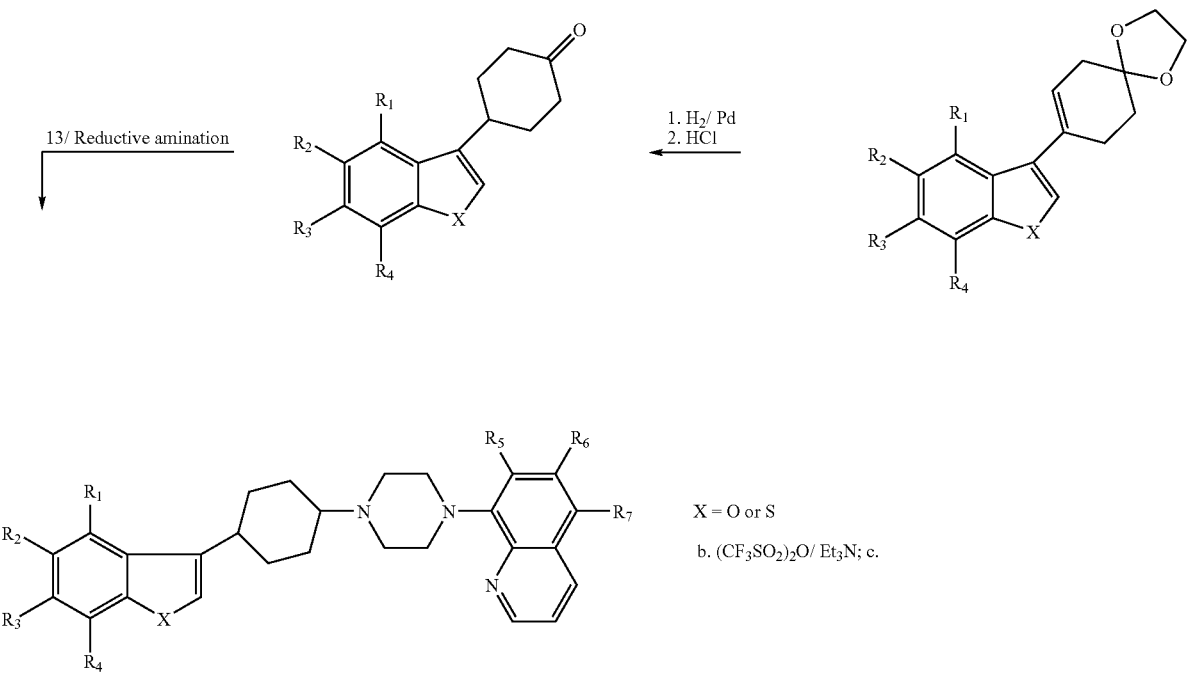
X = O or S
b. (CF$_3$SO$_2$)$_2$O/ Et$_3$N; c.
b. (CF$_3$SO$_2$)$_2$O/ LDA; c. Pinacoleborane/Et3N/PdCl2, dpp ferrocene (Suzuki Coupling) 1,2-Dimethoxy ethane/ LiCl/ (Ph$_3$)$_4$Pd(0)
Scheme 9
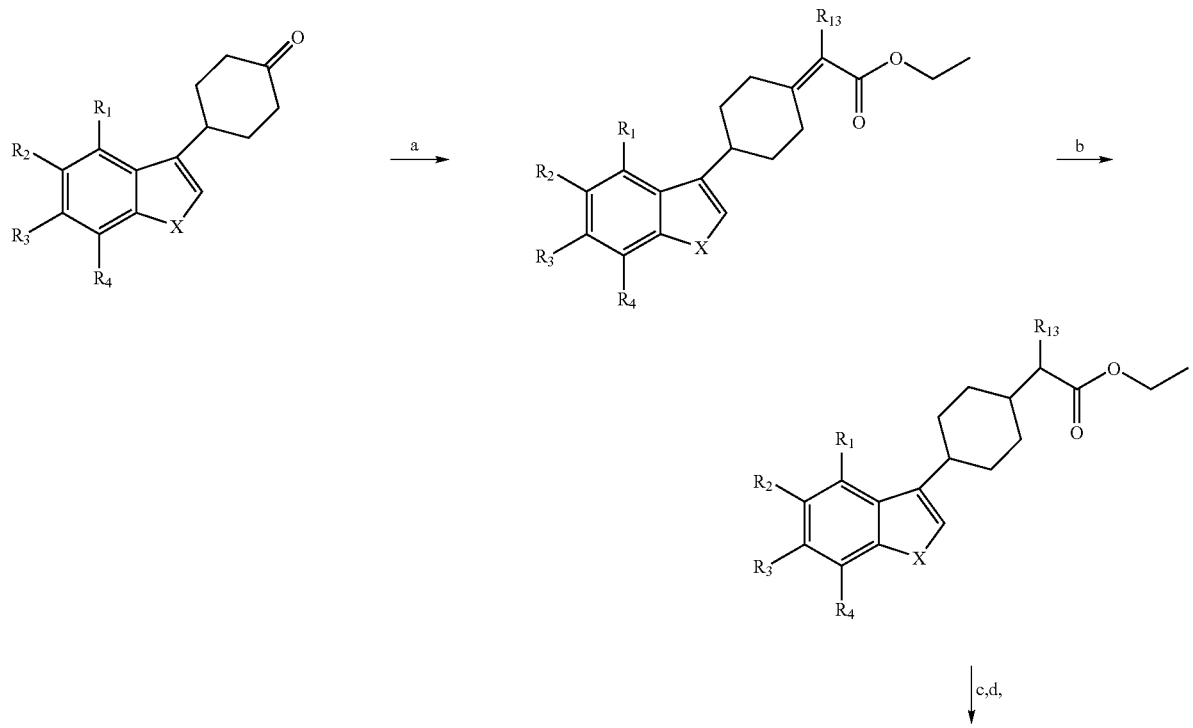

-continued

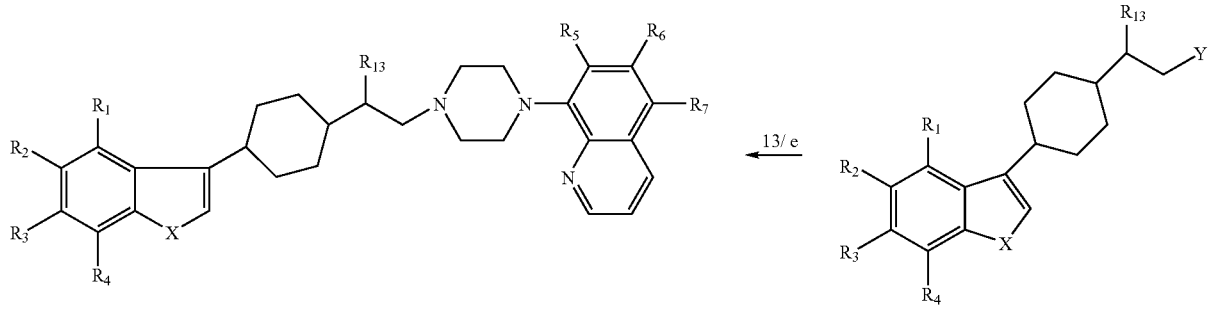

a. Ph$_3$P=CR$_{13}$COOEt/ Toluene/ Reflux; b. Pt/H$_2$; c. LiAlH$_4$/THF; d. Ph$_3$P/CBr$_4$
e. DMSO/Diisopropyl ethylamine, 120° C.

The terms "effective amount", "therapeutically effective amount" and "effective dosage" as used herein, refer to the amount of a compound of formula I that, when administered to a patient, is effective to at least partially ameliorate a condition from which the patient is suspected to suffer. Such conditions include serotonin-related disorders, including but not limited to, anxiety, depression, cognitive deficits, such as those resulting from Alzheimer's disease and other neurodegenerative disorders, schizophrenia, prostate cancer, and nicotine withdrawal.

The term "pharmaceutically acceptable salt", as used hererin, refers to salts derived from organic and inorganic acids as, for example, lactic, citric, acetic, cinnamic, tartaric, succinic, maleic, malonic, mandelic, malic, oxalic, propionic, fumaric, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Where $R_1$ to $R_9$ and $R_{11}$ contain a carboxyl group, salts of the compounds of this invention may be formed with bases such as alkali metals, such as sodium, potassium, and lithium or the alkaline earth metals, such as calcium or magnesium.

The term "patient", as used herein, refers to a mammal, preferably a human.

The terms "administer", "administering" or "administration", as used herein, refer to either directly administering a compound or composition to a patient, or administering a prodrug derivative or analog of the compound to the patient, which will form an equivalent amount of the active compound or substance within the patient's body.

Compounds of formula I have been found to have affinity for the 5-HT reuptake transporter. They are therefore useful in the treatment and/or prevention of serotonin-related disorders. The present invention accordingly provides pharmaceutical compositions that include the compound of formula I; and optionally one or more pharmaceutically-acceptable carriers, excipients, or diluents. The term "carrier", as used herein, shall encompass carriers, excipients and diluents.

Examples of such carriers are well know to those skilled in the art and are prepared in accordance with acceptable pharmaceutical procedures, such as, for example, those described in *Remington's Pharmaceutical Sciences,* 17th edition, ed. Alfonso R. Gennaro, Mack Publishing Company, Easton, Pa. (1985), which is incorporated herein by reference in its entirety. Pharmaceutical acceptable carriers are those carriers that are compatible with the other ingredients in the formulation and are biologically acceptable.

The compounds of formula I can be administered orally or parenterally, neat, or in combination with conventional pharmaceutical carriers. Representative solid carriers include one or more substance that can act as flavoring agents, lubricants, solubilizers, suspending agents, fillers, glidants, compression aids, binders, tablet-disintegrating agents, or encapsulating materials. They are formulated in conventional manner, for example, in a manner similar to that use for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid that is in admixture with the finely divided active ingredient. In tablets, the active ingredient is mixed with a carrier having the necessary compression properties in suitable proportion and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, microcrystalline cellulose, methyl cellulose, sodium carboxymethyl cellulose, carboxymethylcellulose calcium, polyvinylpyrrolidine, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, starches, sugars, low melting waxes, and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Liquid carriers can be used in preparing solutions, suspensions, emulsions, syrups, and elixirs. The active ingredient can be dissolved or suspended in a pharmaceutically acceptable oil or fat. The liquid carrier can obtain other suitable pharmaceutical additives such as, for example, solubilizers, emulsifiers, buffers, preservatives, sweeteners, flavoring agents, suspending agents, thickening agents, colors, viscosity regulators, stablizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myistrate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal, or subcutaneous injection. Sterile solutions can also be administered intravenously. Compositions for oral administration may be in either liquid or solid form.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

When administered for the treatment and/or prevention of a particular disease state or disorder, it is understood that the effective dosage may vary depending upon the particular compound utilized, the mode of administration, the condition, and severity thereof, of the condition being treated, as well as the various physical factors related to the individual being treated. In therapeutic applications, compounds of formula I are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment and/or prevention of a specific case must be subjectively determined by the attending physician. The variables involved include the specific condition and the weight, age, and response pattern of the patient. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the patient's bloodstream, including orally, via implants, parentally (including intravenous, intraperitoneal, intraarticularly and subcutaneous injections), rectally, intranasally, topically, ocularly (via eye drops), vaginally, and transdermally.

In some cases it may be desirable to administer the compounds directly to the airways in the form of an aerosol. For administration by intranasal or intrabrochial inhalation, the compounds of formula I can be formulated into an aqueous or partially aqueous solution.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of formula I can also be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

The compounds of formula I may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of compounds of formula I. The term "prodrug" as used herein, refers to a compound that is convertible in vivo by metabolic means (e.g. by hydrolysis) to a compound of formula I. Various forms of prodrugs are known in the art such as those discussed in, for example, Bundgaard (ed.), Design of Prodrugs, Elsevier (1985); Widder, et al. (ed.), Methods in Enzymology, vol. 4, Academic Press (1985); Krogsgaard-Larsen, et al., (ed.), "Design and Application of Prodrugs, Textbook of Drug Design and Development, Chapter 5, 113-191 (1991); Bundgaard, et al., *Journal of Drug Delivery Reviews*, 8:1-38 (1992); Bundgaard, *Journal of Pharmaceutical Sciences*, 77:285 et seq. (1988); Higuchi and Stella (eds.), *Prodrugs as Novel Drug Delivery Systems*, American Chemical Society (1975), each of which is incorporated by reference in its entirety.

The present invention further provides compounds of the invention for use as an active therapeutic substance. Compounds of formula I are of particular use in the treatment and/or prevention of diseases related to serotonin-related disorders.

The present invention further provides methods of treating and/or preventing serotonin-related disorders, including depression, anxiety, cognitive deficits, schizophrenia, prostate cancer, or nicotine withdrawal, in mammals including humans, which comprises administering to the afflicted mammal an effective amount of a compound or a pharmaceutical composition of the invention.

EXAMPLES

Preparation of Intermediates

Example 1

Intermediate 1—8-piperazino quinoline

This intermediate has been prepared by generally following the procedure described in WO 00/40554, which is incorporated herein by reference.

Example 2

Intermediate 2—6-fluoro-8-bromo-quinoline

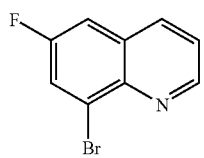

To a mixture of 7.0 g of 2-bromo-4-fluoro-aniline, 7.0 g of glycerol and 13.0 g of m-nitrobenzene sulfonic acid sodium salt, 20 ml of 70% sulfuric acid was added drop by drop. The reaction temperature was raised to 150° C. for 4 hr. The mixture was cooled, poured on water neutralized with NaOH and the formed precipitate was filtered to yield 34.7 g of 6-fluoro-8-bromo-quinoline. MS (ES) m/z (relative intensity): 227 ($M^++H$, 100).

Example 3

Intermediate 3—6-fluoro-8-(t-Boc)-piperazino-quinoline

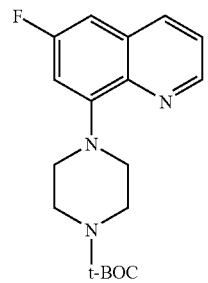

To a mixture of 2.2 g of 6-fluoro-8-bromo-quinoline in THF, was added 0.045 g of $Pd_2(dba)_3$, 1.3 g of NaOt-Bu, 0.044 g of binap, 0.052 g of tetrakis(triphenylphosphine)palladium(0) and 2.2 g of t-Boc piperazine. The mixture was refluxed for 3 hours. The reaction mixture was then cooled to room temperature, diluted with ether, filtered through celite and concentrated in vacuo. The crude material was then purified by flash chromatography to give 3.0 g of 6-fluoro-8(t-Boc)-piperazino-quinoline. MS (ES) m/z (relative intensity): 332 ($M^++H$, 100).

Example 4

Intermediate 4—6-fluoro-8-piperazino-quinoline

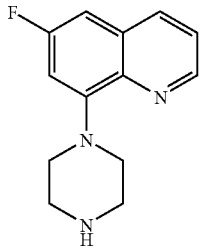

To a solution of 3.0 g 6-fluoro-8-(t-Boc)-piperazino-quinoline in 10 ml of dioxane, 10 ml of 4 N HCl/dioxane was added. The mixture was stirred at room temperature overnight. The formed precipitate was filtered, dissolved in water and extracted with $CH_2Cl_2$, dried, and the solvent removed to yield 1.9 g of 6-fluoro-8-piperazino-quinoline. MP: 103° C.; MS (ES) m/z (relative intensity): 233 ($M^++H$, 100).

Example 5

Intermediate 5—5-fluoro-8-piperazino-quinoline

To a mixture of 9 g of 8-chloro-6-methoxy-quinoline in 75 ml of dry THF, was added 0.64 g of $Pd_2(dba)_3$, 6.2 g of NaOt-Bu, 0.274 g of 2-dicyclohexylphosphino-2'-(N,N-dimethyl-amino)biphenyl (also known as cymap) and 11.2 g of t-Boc piperazine. The mixture was refluxed for 5 hours. The reaction mixture was then cooled to room temperature, diluted with ether and filtered through celite. The filtrate was concentrated in vacuo. The crude material was then purified by flash chromatography using 300 ml of silica gel and 100% $CH_2Cl_2$ then 50% ethyl acetate/hexane to yield 16.5 g of 5-fluoro-8-piperazino-quinoline.

Example 6

Intermediate 6—6-chloro-8-piperazino-quinoline and 6-methyl-8-piperazino-quinoline These intermediates have been prepared generally using the method used to prepare 6-fluoro-8-piperazino-quinoline as detailed above, using the corresponding starting material substituted with aniline.

Example 7

Intermediate 7—5-chloro-8-(trifluoromethylsulfonyloxy)-quinoline

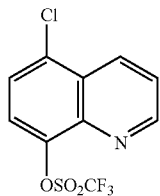

To a suspension of 5-chloro-8-hydroxy-quinoline (8.95 g) in 100 ml of $CH_2Cl_2$, 20 ml of TEA was added. The suspension was dissolved then cooled to −15° C. A solution of 21.1 g of triflic anhydride in 50 ml of $CH_2Cl_2$ was added dropwise, with cooling. After complete addition, the reaction was stirred at −15° C. for 30 min. The reaction was diluted with $CH_2Cl_2$, washed with a solution of $NaHCO_3$, then with water, dried, and the solvent was removed to yield 15.0 g of 5-chloro-8-(trifluoromethylsulfonyloxy)-quinoline. MP: 80-83° C.; MS (ES) m/z (relative intensity): 312 ($M^++H$,100). Elemental analysis for $C_{10}H_5ClF_3NO_3S$; Calculated: C: 38.54; H: 1.62; N: 4.4; Found: C: 38.3; H: 1.73; N: 4.5.

Example 8

Intermediate 8—5-chloro-8-(t-Boc)-piperazino-quinoline

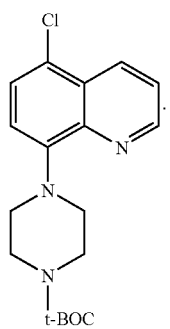

To a mixture of 4.0 g of 5-chloro-8-trifluoromethyl-quinoline in 30 ml of THF, was added 5.9 g of cesium carbonate, 0.360 g of BINAP, 0.120 g of Palladium acetate and 2.8 g of t-Boc piperazine. The mixture was refluxed for 5 hours. The reaction mixture was then cooled to room temperature, diluted with ether, filtered through celite and concentrated in vacuo. The crude material was then purified by flash chromatography to yield 2.4 g of 5-chloro-8-(t-Boc)-piperazino-quinoline. MP: 127° C.; MS (ES) m/z (relative intensity): 348 ($M^++H$, 100). Elemental analysis for $C_{18}H_{22}ClN_3O_2$; Calculated: C: 62.15; H: 6.37; N: 12.0; Found: C: 62.5; H: 6.23; N: 11.66.

Example 9

Intermediate 9—5-chloro-8-piperazino-quinoline

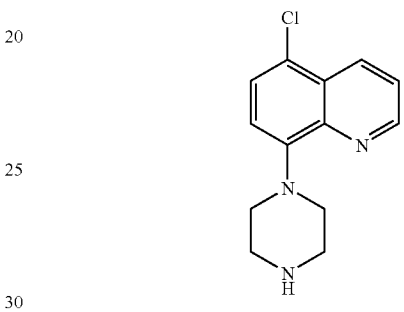

To a solution of 2.2 g 5-Chloro-8-(t-Boc)-piperazino-quinoline in 10 ml dioxane, 5 ml of 4 N HCl/Dioxane were added. The mixture was stirred at room temperature overnight. The formed precipitate was filtered, dissolved in water and extracted with $CH_2Cl_2$, dried and solvent removed to give 1.0 g of the desired product. MS (ES) m/z (relative intensity): 248 ($M^++H$, 100). Elemental analysis for $C_{13}H_{14}ClF_3N_3$; Calculated: C: 63.03; H: 5.7; N: 16.96; C: 62.49; H: 5.32; N: 15.73.

Example 10

Intermediate 10—8-chloro-6-hydroxy-quinoline

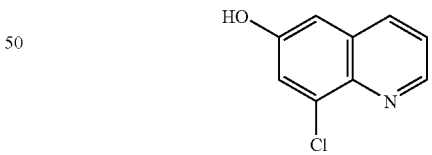

In a 500 ml 3-necked flask equipped with a mechanical stirrer and a reflux condenser, added in order were 2.0 g ferrous sulfate, 6.4 g 4-amino, 3-chloro-phenol (generated from 9.0 g of the corresponding commercially available HCl salt), 2.9 m nitrobenzene and a cold solution of 3.0 g boric acid in 16 g of glycerol. Then, 9 ml of concentrated sulfuric acid was added drop by drop with cooling. The ice bath was removed and replaced by an oil bath and the mixture was heated cautiously to 120° C. for 2 hrs, then at 150° C. and kept stirring under this temperature for 20 hrs. The mixture was then cooled and poured on crushed ice and the resulting solution was neutralized to with $K_2CO_3$ (saturated solution in water) till exactly pH 5. The product separated as a light brown solid which was filtered off, washed with water and hexane and dried in a vacuum oven (35° C.) overnight. The product was purified by dissolving it in a minimal amount of THF, and the solution poured in 20× volume of hexane, giving 7 g (77%) of the desired product.

Example 11

Intermediate 11—8-chloro-6-methoxy-quinoline

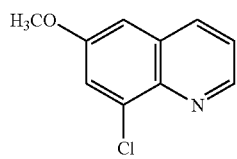

To a solution of 15 g of 8-chloro-6-hydroxy-quinoline in (50 ml) DMF, 23 g of $K_2CO_3$ were added followed by 18 g iodomethane. The mixture was stirred at room temperature overnight. Water was added and the product was extracted with $CH_2Cl_2$ dried and the solvent removed. The crude product was filtered through 250 ml of silica gel using 50% ethyl acetate/hexane to give 11 g of the desired product.

Example 12

Intermediate 12—6-methoxy-8-(t-Boc)-piperazino-quinoline

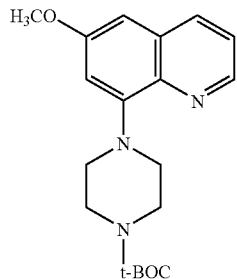

To a mixture of 9 g of 8-chloro-6-methoxy-quinoline in 75 ml dry THF, was added 0.64 g $Pd_2(dba)_3$, 6.2 g NaOt-Bu, 0.274 g of 2-Dicyclohexylphosphino-2'-(N,N-dimethyl-amino)biphenyl (also known as cymap) and 11.2 g t-Boc piperazine. The mixture was refluxed for 5 hrs. The reaction mixture was then cooled to room temperature, diluted with ether, and filtered through celite. The filtrate was concentrated in vacuo. The crude material was then purified by flash chromatography using 300 ml of silica gel and 100% $CH_2Cl_2$ then 50% ethyl acetate/hexane to give 16.5 g of the desired product.

Example 13

Intermediate 13—6-methoxy-8-piperazino-quinoline

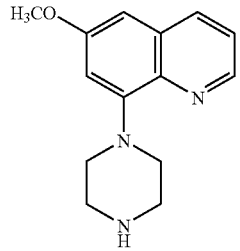

To a solution of 16.0 g 6-methoxy-8-(t-Boc)-piperazino-quinoline in 100 ml dioxane, 30 ml of 4 N HCl/dioxane were added. The mixture was stirred at room temperature overnight. The formed precipitate was filtered, dissolved in water and extracted with $CH_2Cl_2$, dried and solvent removed to give 10.5 g of the desired product.

Example 14

Intermediate 14—trifluoro-methanesulfonic acid 5-fluoro-benzo[b]thiophen-3-yl ester

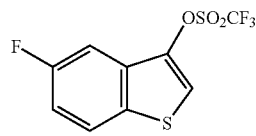

To a cold solution (−20° C.) of 5-fluoro-benzothiophenone (15 g) in $CH_2Cl_2$ (100 ml), TEA (27 g) was added. To the cold mixture, a solution of triflic anhydride (37.7 g) in $CH_2Cl_2$ (25 ml) was added drop by drop. The temperature was left to rise to 0° C. and kept at this temperature for 1 hr. It was then quenched with a solution of $NaHCO_3$ and the product extracted with $CH_2Cl_2$, dried over $MgSO_4$, and the solvent was removed to give 23.0 g of the desired product.

Example 15

Intermediate 15—7-methoxytrifluoro-methanesulfonic acid 5-fluoro-benzo[b]thiophen-3-yl ester

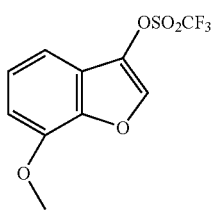

125 To a cold solution (−20° C.) of 7-MeO-Benzofuranone (3.3 g) in $CH_2Cl_2$ (30 ml), TEA (8.3 ml) was added. To the cold mixture, a solution of triflic anhydride (8.5 g) in $CH_2Cl_2$ (20 ml) was added drop by drop. The temperature was kept at this temperature for 1 hr. It was then quenched with a solution of NaHCO$_3$ and the product extracted with CH$_2$Cl$_2$, dried over MgSO$_4$, and the solvent was removed to give 5.6 g of the desired product.

Example 16

Intermediate 16—2-(benzo[b]thiophen-3-yl0-4,4,5, 5-tetramethyl-[1,2]oxaborolane

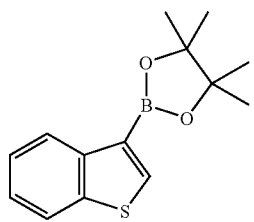

To a solution of 3-bromobenzothiophene (10 g) in dioxane (30 ml) a solution of pinacoleborane (1 M, 9.0 g) in THF (70 ml) was added followed by TEA (10.7 g) and PdCl$_2$, dpp ferrocene. The reaction was heated at 60° C. overnight. The solvent was removed under vacuum. Ether was added and the insoluble was filtered. The filtrate was evaporated and filtered through silica gel (300 ml) using 5% Ethyl acetate/Hexane to give 9.0 g of desired product.

Example 17

Intermediate 17—2-(5-fluoro-benzo[b]thiophen-3-yl0-4,4,5,5-tetramethyl-[1,2]oxaborolane

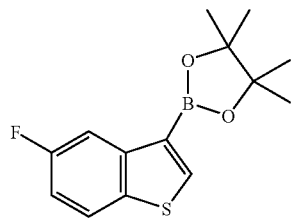

To a solution of 5-fluoro-3-trifluoromethyl-benzothiophene (10 g) in dioxane (50 ml) a solution of pinacoleborane (1 M, 7.2 g) in THF (56 ml) was added, followed by TEA (15 ml) and PdCl$_2$,dpp ferrocene (0.913 g). The reaction is heated at 60° C. overnight. The solvent was removed under vacuum. Ether was added and the insoluble was filtered. The filtrate was evaporated and filtered through (200 ml) of silica gel using 5% Ethyl acetate/hexane to give 3.5 g of desired product. MP: 80-83° C.; MS (ES) m/z (relative intensity): 312 (M$^+$+H,100). Elemental analysis for C$_{14}$H$_{16}$BFO$_2$S; Calculated: C: 60.45; H: 5.8; Found: C: 60.48; H: 5.68.

Example 18

Intermediate 18—2-(benzo[b]furan-3-yl0-4,4,5,5-tetramethyl-[1,2]oxaborolane

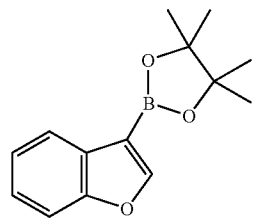

To a mixture of 3-bromo-benzofuran (500 g) in TEA (1 ml) a solution of (1M) pinacoleborane in THF (0.476 g/3.75 ml) in THF was added followed by PdCl$_2$,dpp ferrocene. The reaction is heated at 150° C. for 3 min in the microwave. The solvent was removed under vacuum. The residue was taken in water and extracted with ether, dried over magnesium sulfate and the solvent removed. The residue was filtered through 50 ml of silica gel using 10% Ethyl acetate/hexane to give 0.350 g of desired product.

Example 19

Intermediate 19—2-(7-methoxy benzo[b]furan-3-yl0-4,4,5,5-tetramethyl-[1,2]oxaborolane

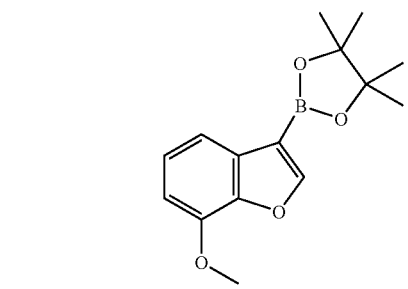

To a mixture of 7-methoxy-3-trifluoromethylsulfonyl-benzofuran (0.660 g) in TEA (1 ml) a solution of (1M) pinacoleborane in THF (0.476 g/3.75 Ml) was added followed by PdCl$_2$,dpp ferrocene. The reaction was heated at 150° C. for 3 min in the microwave. The solvent was removed under vacuum. The residue was taken in water and extracted with ether, dried over magnesium sulfate and the solvent removed. The residue was filtered through 50 ml of silica gel using 10% ethyl acetate/hexane to give 0.350 g of desired product.

Example 20

Intermediate 20—trifluoro-methanesulfonic acid 1,4-dioxa-spiro[4,5]dec-7-en-8yl ester

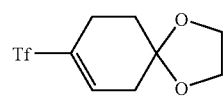

To a cold solution of LDA (2.35 g) in THF (20 ml) at −78° C., a solution of 1,4 cyclohexanedione mono ethylene ketal (3.0 g) in THF (20 ml) was added drop wise with cooling. After 90 min at −78° C., a solution of N-phenyl trifluoromethane sulfonimide (7.8 g) in THF (20 ml) was added drop wise with cooling and the reaction temperature was left to rise to room temperature. The THF is removed under vacuum, and the residue was filtered through silica gel (500 ml) and 2% ethyl acetate/hexane to give 2.0 g of the desired product.

Example 21

Intermediate 21—8-benzo[b]thiophen-3-yl-1,4-dioxa-spiro[4,5]dec-7-ene

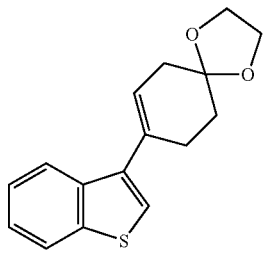

To a mixture of 2-(benzo[b]thiophen-3-yl0-4,4,5,5-tetramethyl-[1,2]oxaborolane (2.6 g) and trifluoro-methanesulfonic acid 1,4-dioxa-spiro[4.5]dec-7-en-8yl ester (2.9 g) in 1,2-dimethoxyethane (DME, 10 ml), $Na_2CO_3$ (2.8 g in 10 ml $H_2O$) was added followed by LiCl (0.421 g) in water and Tetrakis(triphenylphosphine)Palladium(0) (0.100 g). The reaction was heated at 70° C. overnight. The reaction was then cooled to room temperature and the solvent removed under vacuum. The residue was taken in $CH_2Cl_2$ and washed with aqueous 2N $Na_2CO_3$. The organic phase was separated and dried over $MgSO_4$. The solvent was then removed and the residue filtered through 200 ml of silica gel using 15% ethyl acetate/hexane to give 2.0 g of the title compound. MP: 80-83° C.; MS (ES) m/z (relative intensity): 273 ($M^+$+H, 100). Elemental analysis for $C_{16}H_{16}O_2S$: Calculated: C: 70.56; H: 5.92; Found: C: 68.79; H: 5.88.

Example 22

Intermediate 22—8-(5-fluoro-benzo[b]thiophen-3-yl)-1,4-dioxa-spiro[4,5]dec-7-ene

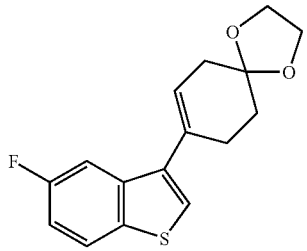

To a mixture of 2-(5-fluoro-benzo[b]thiophen-3-yl0-4,4,5,5-tetramethyl-[1,2]oxaborolane (1.6 g) and trifluoro-methanesulfonic acid 1,4-dioxa-spiro[4.5]dec-7-en-8yl ester (2.0 g) in 1,2-dimethoxyethane (DME, 10 ml ), $Na_2CO_3$ (1.2 g in 6 ml $H_2O$) was added followed by LiCl (0.530 g) in water and Tetrakis(triphenylphosphine)Palladium(0) (100 g). The reaction was heated at 80° C. for 2 hours. The reaction was then cooled to room temperature and the solvent removed under vacuum. The residue was taken in ether and filtered over celite. The organic phase was separated and dried over $MgSO_4$. The solvent was removed and the residue filtered through 150 ml of silica gel using 15% ethyl acetate/hexane to give 2.2 g of the title compound. MP: 80-83° C.; MS (ES) m/z (relative intensity): 291 ($M^+$+H,100).

Example 23

Intermediate 23—8-benzofuran-3-yl-1,4-dioxa-spiro[4,5]dec-7-ene

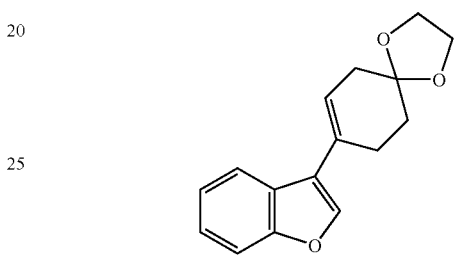

To a mixture of 2-(benzo[b]furan-3-yl0-4,4,5,5-tetramethyl-[1,2]oxaborolane (2.44 g) and trifluoro-methanesulfonic acid 1,4-dioxa-spiro[4.5]dec-7-en-8yl ester (2.9 g) in DME (20 ml), $Na_2CO_3$ (2.9 g in 10 ml $H_2O$) was added followed by a solution of LiCi (1.26 g) in water and Tetrakis(triphenylphosphine)Palladium(0) (0.600 g). The reaction was heated at 80° C. for 1 hr. It was then cooled to room temperature and the solvent was removed under vacuum. The residue was taken in ether and filtered over celite. The organic phase was separated washed with a solution of $Na_2CO_3$, then with a 10% solution of $NH_4OH$, dried over $MgSO_4$. The solvent was then removed and the residue was filtered through 200 ml of silica gel using 10% ethyl acetate/hexane to give 0.800 g of the title compound. MS (ES) m/z (relative intensity): 257 ($M^+$+H, 100).

Example 24

Intermediate 24—8-(7-methoxy-benzofuran-3-yl)-1,4-dioxa-spiro[4,5]dec-7-ene

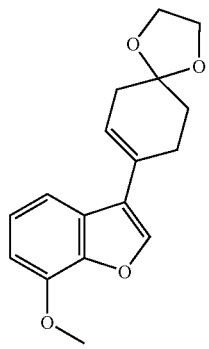

8-(7-methoxy-benzofuran-3-yl)-1,4-dioxa-spiro[4,5]dec-7-ene has been prepared in the same manner as the non substituted analog using 7-methoxy-bezofuranone. MS (ES) m/z (relative intensity): 287 (M$^+$+H,100).

Example 25

Intermediate 25—8-benzo[b]thiophen-3-yl-1,4-dioxa-spiro[4,5]decane

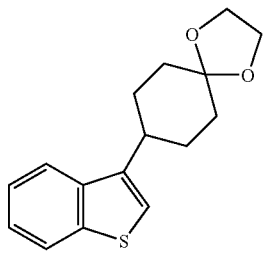

A mixture of 8-benzo[b]thiophen-3-yl-1,4-dioxa-spiro[4,5]dec-7-ene (2.0 g) and 10% palladium on carbon (0.700 g) in ethanol/THF (25 ml/35 ml) was hydrogenated for 90 min. The catalyst was filtered off and the solvent was removed under vacuum to give 1.8 g of the desired product. MP: 80-83° C.; MS (ES) m/z (relative intensity): 275 (M$^+$+H, 100). Elemental analysis for $C_{16}H_{18}O_2$; Calculated: C: 70.04; H: 6.61; N: 0; Found: C: 69.94; H: 6.72; N: 0.

Example 26

Intermediate 26—5-fluoro-8-benzo[b]thiophen-3-yl-1,4-dioxa-spiro[4,5]decane

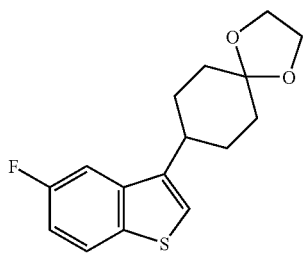

A mixture of 8-(5-fluoro-benzo[b]thiophen-3-yl)-1,4-dioxa-spiro[4,5]dec-7-ene (1.1 g) and 10% palladium on carbon (0.400 g) in ethanol/THF (25 ml/35 ml) was hydrogenated for 6 hrs. The catalyst was filtered off and the solvent was removed under vacuum to give 1.0 g of the desired product. MS (ES) m/z (relative intensity): 293 (M$^+$+H, 100).

Example 27

Intermediate 27—8-benzofuran-3-yl-1,4-dioxa-spiro[4,5]decane

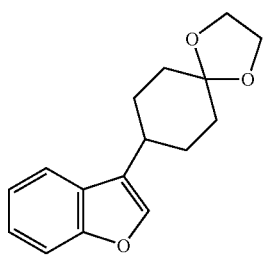

A mixture of 8-benzofuran-3-yl-1,4-dioxa-spiro[4.5]dec-7-ene (0.420 g) and 10% palladium on carbon (0.100 g) in ethanol/THF (20 ml/10 ml) was hydrogenated for 3 hours. The catalyst was filtered off and the solvent was removed under vacuum. The product was filtered through 50 ml of silica gel and 25% ethyl acetate to give 0.350 g of the desired product. MS (ES) m/z (relative intensity): 259 (M$^+$+H, 100).

Example 28

Intermediate 28—7-methoxy-benzofuran-3-yl-1,4-dioxa-spiro[4,5]decane

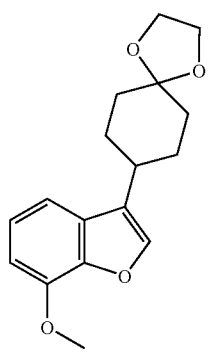

A mixture of 8-(7-methoxy-benzofuran-3-yl)-1,4-dioxa-spiro[4,5]dec-7-ene and 10% palladium on carbon in ethanol/THF was hydrogenated for 3 hrs. The catalyst was filtered off and the solvent was removed under vacuum. The product was filtered through 50 ml of silica gel and 25% ethyl acetate/hexane to give the desired product. MS (ES) m/z (relative intensity): 289 (M$^+$+H, 100).

Example 29

Intermediate 29—4-(3H-inden-1-yl)-cyclohexanone

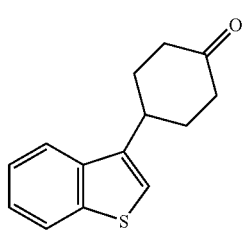

A solution of 8-benzo [b]thiophene-3-yl-1,4-dioxa-spiro[4,5]decane (1.8 g) in (50 ml) 1:1 tetrahydrofuran-hydrochloric acid (2 N) was stirred at room temperature for 5 hrs. THF was removed under vacuum and the product was extracted with $CH_2Cl_2$, dried and solvent removed under reduced pressure to give 1.2 g of the desired product. MP: 97-100° C.; MS (ES) m/z (relative intensity): 231 (M$^+$+H, 100). Elemental analysis for $C_{14}H_{14}OS$; Calculated: C: 73.01; H: 6.13; N: 0; Found: C: 73.38; H: 6.3; N: 0.

Example 30

Intermediate 30—4-(6-fluoro-3H-inden-1-yl)-cyclohexanone

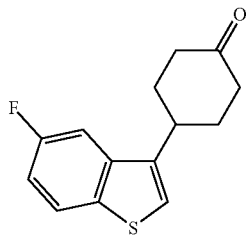

A solution of 8-benzo[b]thiophene-3-yl-1,4-dioxa-spiro [4,5]decane (1.0 g) in (20 ml) tetrahydrofuran-hydrochloric acid (2 N) was stirred at room temperature for 3 hrs. THF was removed under vacuum and the product was extracted with ether, dried and the solvent removed under reduced pressure to give 0.650 g of the desired product. MS (ES) m/z (relative intensity): 237 (M$^+$+H, 100).

Example 31

Intermediate 31—4-(benzofuran-3-yl)-cyclohexanone

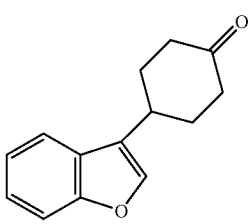

A solution of 8-benzofuran-3-yl-1,4-dioxa-spiro[4,5]decane (0.350 g) in (20 ml) 1:1 tetrahydrofuran-hydrochloric acid (2 N) was stirred at room temperature for 6 hours. THF was removed under vacuum and the product extracted with methylene chloride, dried and solvent removed under reduced pressure to give 0.300 g of the desired product. MS (ES) m/z (relative intensity): 215 (M$^+$+H, 100).

Example 32

Intermediate 32—4-(7-methoxy-benzofuran-3-yl)-cyclohexanone

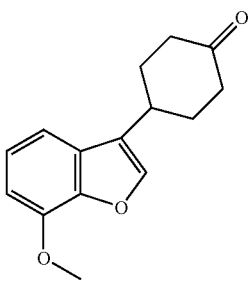

A solution of 7-methoxy-benzofuran-3-yl-1,4-dioxa-spiro [4,5]decane (3.0 g) in (45 ml) 1:1 tetrahydrofuran-hydrochloric acid (2 N) was stirred at room temperature for 3 hrs. THF was removed under vacuum and the product extracted with ethyl acetate, dried and solvent removed under reduced pressure to give 1.3 g of the desired product. MS (ES) m/z (relative intensity): 245 (M$^+$+H, 100).

Example 33

Intermediate 33—8-benzofuran-2-yl-1,4-dioxa-spiro [4,5]decan-8-ol

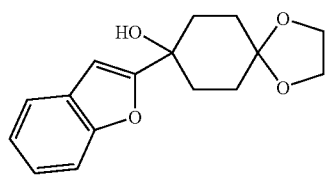

To a cold solution of 2.5 M BuLi (2.35 g) in hexane, 60 ml of THF was added and cooled to −78° C., followed by the addition of a solution of benzofuran (5.0 g) in THF (30 ml), drop by drop. After 30 min at −78° C., a solution of 1,4 cyclohexanedione monoethylene ketal (7.27 g) in THF (30 ml) was added drop wise with cooling, and the reaction temperature was left to rise to room temperature. The reaction mixture was poured on a cold aqueous solution of NH$_4$Cl. The THF was removed under vacuum, and the product was extracted with CH$_2$Cl$_2$ dried over magnesium sulfate to give 7.0 g of the desired product.

Example 34

Intermediate 34—4-benzofuran-2-yl-cyclohex-3-enone

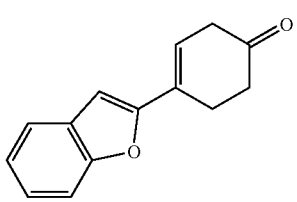

To a solution of benzofuran-2-yl-1,4-dioxa-spiro[4.5]decan-8-ol (2.0 g) in CH$_2$Cl$_2$ (20 ml) was added TFA (4 ml) and the reaction was stirred at room temperature overnight. Water was added and the product was extracted with CH$_2$Cl$_2$. The organic phase was washed with sodium bicarbonate dried over magnesium sulfate and the solvent removed to give 1.20 g of the desired product. MS (ES) m/z (relative intensity): 213 (M$^+$+H, 100).

Example 35

Intermediate 35—4-benzofuran-2-yl-cyclohexanone

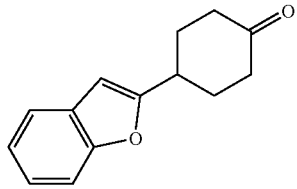

A mixture of 4-benzofuran-2-yl-cyclohex-3-enone (1.2 g) and 10% palladium on carbon in ethanol/THF was hydrogenated for 6 hours. The catalyst was filtered off and the solvent was removed under vacuum. The product was filtered through 50 ml of silica gel and 25% ethyl acetate/Hexane to give 1.1 g of the desired product. MS (ES) m/z (relative intensity): 215 ($M^+$+H, 100).

Example 36

Intermediate 36—8-benzo[b]thiophen-2-yl-1,4-dioxa-spiro[4,5]decan-8-ol

A solution of benzo[b]thiophene (10 g, 75 mmol) in still-dried THF (100 ml) was cooled to −78° C., and n-BuLi (36 ml, 2.5 M in hexane) was added. The reaction was stirred 15 min, then a solution of 1,4-cyclohexanedione mono ethylene ketal (11.12 g, 71 mmol) in THF (20 ml) was added. The reaction mixture was stirred at −78° C. for 10 min, and then slowly warmed to room temperature. The reaction was slowly quenched with water (200 ml) and extracted into EtOAc (2×200 ml). The organic phases were combined, dried over $Na_2SO_4$ and concentrated to a clear oil. The product was precipitated from 40% ethyl acetate/hexane and washed with hexane to give 12.87 g (66%) of the title compound as a white solid. The mother liquor was concentrated and purified by column chromatography (40% EtOAc/hexane) to afford an additional 4.91 g (25%) of the product as a white solid: MP:>145° C. Elemental Analysis for $C_{16}H_{18}O_3S$; Calculated: C, 66.18; H, 6.25; Found: C, 66.26; H, 6.22.

Example 37

Intermediate 37—4-benzo[b]thiophen-2-yl-cyclohex-3-enone

A solution of 8-benzo[b]thiophen-2-yl-1,4-dioxa-spiro[4,5]decan-8-ol (12 g, 44 mmol) was dissolved in THF (150 ml), 1 N aqueous HCl (150 ml) was added, and the mixture was stirred at room temperature overnight. The THF was removed under vacuum, the aqueous residue was made basic with 1 M aqueous NaOH (150 ml) and extracted into ethyl acetate (3×150 ml). The organic phases were combined, dried over $Na_2SO_4$, and concentrated under vacuum, affording 9.8 g (90%) of the title compound as a pale yellow solid: MP: >120° C. Elemental Analysis for $C_{14}H_{14}O_2S$; Calculated: C, 68.26; H, 5.73; Found: C, 67.98; H, 5.71.

Example 38

Intermediate 38—4-benzo[b]thiophen-2-yl-cyclohexanone

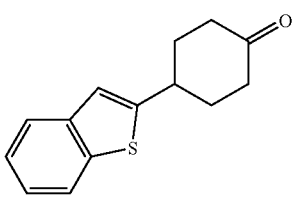

A mixture of 4-benzo[b]thiophen-2-yl-cyclohex-3-enone (0.95 g, 4.2 mmol) and 0.5 g 10% Pd/C in ethanol (100 ml) was hydrogenated at 40 psi overnight. The catalyst was removed by filtration through celite and was washed with ethyl acetate (100 ml) and methylene chloride (100 ml). The filtrate was concentrated under vacuum, and the residue was purified by flash chromatography on silica gel (30% ethyl acetate/hexane), to afford 0.75 g of a yellow oil which crystallized on standing. NMR indicated this product was 2-(4,4-diethoxycyclohexyl)-benzo[b]thiophene. A solution of this ketal in 25 ml THF and 25 ml 1 N HCl was stirred at room temperature over a weekend. The THF was removed under vacuum, and the aqueous residue was made basic with 1 M NaOH (50 ml) and extracted with ethyl acetate (2×100 ml). The combined organic layers were dried over $Na_2SO_4$, filtered and concentrated under vacuum to afford 0.53 g (55%) of the title compound as a brownish solid. MS (ES) m/z (relative intensity): 231 ($M^+$+H, 100).

Preparation of Compounds of the Invention

Example 39

Preparation of 8-{4-[2-(1-benzofuran-3-yl)ethyl]-1-piperazinyl}-6-fluoroquinoline ("Compound 1")

Step 1: To a stirred solution of methyl salicylate (15.2 g, 0.1 mol) and anhydrous potassium carbonate (50.0 g, excess) in acetone (500 ml), ethyl bromoacetate (16.7 g, 0.1 mol) was added. The reaction mixture was refluxed for 24 hrs and cooled to room temperature. It was then filtered and concentrated. The oily residue was extracted with chloroform and washed well with water. The organic layer was dried over anhydrous $MgSO_4$ and filtered. It was concentrated and taken to the next step without any purification. White oil; Yield: 22.0 g (92%); (M+): 239.

Step 2: The methyl-2-(ethoxy-2-oxoethoxy)benzoate obtained from the step 1, (11.9 g, 50 mmol) was dissolved in THF:MeOH (1:1) (300 ml) and 5N NaOH (100 ml) was added. The reaction mixture was refluxed for 24 hrs and cooled to room temperature. Afterwards, it was concentrated to dryness and dissolved in water. The aqueous layer was acidified with con. HCl and the separated solid were filtered. The product was then washed well with water and dried. The product was taken to the next step without any purification. White solid; Yield: 9.0 g 91%; MP: 125-128° C.: 197 (M+H).

Step 3: The 2-(carboxymethoxy)-benzoic acid compound obtained from the step 2 (9.8 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid was then suspended in 1 N HCl and refluxed for 2 hrs. A dark red solid, benzofuran-3 (2H)-one precipitated from the reaction mixture. It was filtered and washed well with water. It was dried at 40° C. and used for the next step with out further purification. Yield: 3.5 g (51%); (M+H): 135.

Step 4: A mixture of benzofuran-3 (2H)-one (1.34 g, 10 mmol) and (carboxymethylene) triphenylphosphorane (5.22 g, 15 mmol) was refluxed in toluene (100 ml) for 48 hrs. At the end, the reaction mixture was concentrated and loaded over a silica-gel column. The column was eluted with hexane (500 ml) and then with 25% ethyl acetate. The product, ethyl(-1-benzofuran-3-yl)acetate was obtained as a white oil. Yield: 2.0 g (98%); (M+H): 205.

Step 5: To a stirred suspension of LiAlH4 (200 mg, excess) in THF at 0° C., ethyl(-1-benzofuran-3-yl)acetate (1.02 g, 5 mmol) in THF (20 mL) was added slowly. After the addition, the reaction mixture was stirred at room temperature for 1 hr and quenched with saturated $NH_4Cl$ solution. The product was extracted with chloroform and washed well with water. It was dried over anhydrous $MgSO_4$, filtered and concentrated. The product 2-(1-benzofuran-3-yl)ethanol obtained as a white oil was pure enough to be taken to next step without further purification. Yield: 800 mg (98%); (M+H): 163.

Step 6: To a stirred solution of 2-(1-benzofuran-3-yl) ethanol (815 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water, and dried over anhydrous $MgSO_4$. It was then filtered and concentrated. The crude product obtained was taken to next step without any purification. A mixture of tosylate (316 mg. 1 mmol) (obtained by the above mentioned process) and 6-fluoro-8-piperazino quinoline (231 mg, 1 mmol) was heated at 120° C. in DMSO in the presence of N,N-diisopropylethylamine (5 ml, excess) for 24 hrs. At the end, reaction mixture was quenched with water and extracted with chloroform. The organic layer was washed with water and dried over anhydrous $MgSO_4$ and concentrated to dryness. The dark colored solid was purified by silica-gel column chromatography by initially eluting it with 70% ethyl acetate:hexane and then with 55% methanol:ethyl acetate. The product, 8-{4-[2-(1-benzofuran-3-yl)ethyl]-1-piperazinyl}-6-fluoroquinoline, was isolated as yellow oil. Yield: 220 mg (58%); (M+H): 376. $^1$HNMR (400 MHz, $CDCl_3$):δ 8.82~8.80 (dd, $J_1$=1.7 Hz, $J_2$=1.7 Hz, 1H), 8.08~8.03 (dd, $J_1$=1.8 Hz, $J_2$=1.8 Hz, 1H), 7.69~6.32 (m, 8H), 3.50~2.63 (m, 12H).

Example 40

Preparation of 8-{4-[2-(1-benzofuran-3-yl)ethyl]-1-piperazinyl}-6-chloroquinoline ("Compound 2")

8-{4-[2-(1-benzofuran-3-yl)ethyl]-1-piperazinyl}-6-chloroquinoline was prepared by generally following the procedure outlined in example 1, step 6, starting from the tosylate (316 mg, 1 mmol) and 6-chloro-8-piperazino quinoline (247 mg, 1 mmol). The product was purified by silica-gel column chromatography by initially eluting it with 70% ethyl acetate:hexane and then with 5% methanol:ethyl acetate to yield a brown oil. Yield: 80 mg (20%); (M+H): 392; $^1$HNMR (400 MHz, $CDCl_3$):δ 8.86~8.82 (dd, $J_1$=1.7 Hz, $J_2$=1.7 Hz, 1H); 8.02~8.00 (dd, $J_1$=1.8, $J_2$=1.8 Hz, 1H); 7.78~6.86); (m, 8H); 3.51~2.58 (m, 12H).

Example 41

Preparation of 8-{4-[2-(1-benzofuran-3-yl)ethyl]-1-piperazinyl}-6-methylquinoline ("Compound 3")

8-{4-[2-(1-benzofuran-3-yl)ethyl]-1-piperazinyl}-6-methylquinoline was prepared by generally following the procedure outlined in example 1, step 6, starting from the tosylate (316 mg, 1 mmol) and 6-methyl-8-piperazino quinoline (227 mg, 1 mmol). The product was purified by silica-gel column chromatography by eluting it initially with 70% ethyl acetate:hexane and then with 5% methanol; ethyl acetate. Brown oil; Yield: 120 mg, 32%; (M+H): 372; $^1$HNMR (400 MHz, $CDCl_3$):δ 8.86~8.80 (dd, $J_1$=1.7 Hz, $J_2$=1.7 Hz, 1H); 8.02~8.00 (dd, $J_1$=1.8 Hz, $J_2$=1.8 Hz, 1H); 7.78~6.98 (m, 8H); 3.50~2.56 (m, 12H); 2.50 (s, 3H).

Example 42

Preparation of 8-{4-[2-(1-benzofuran-3-yl)ethyl]-1-piperazinyl}-6-methoxyquinoline ("Compound 4")

8-{4-[2-(1-benzofuran-3-yl)ethyl]-1-piperazinyl}-6-methoxyquinoline was prepared by generally following the procedure outlined in example 1, step 6, starting from the tosylate (316 mg, 1 mmol) and 6-methoxy-8-piperazino quinoline (243 mg, 1 mmol) (213 mg, 1 mmol). The product was purified by silica-gel column chromatography by initially eluting it with 80% ethyl acetate:hexane and then with 5% methanol:ethyl acetate to yield a brown liquid. Yield: 180 mg (46%); (M+H):388; $^1$H NMR δ8.72 (d, 1H), 8.05 (q, 1H), 7.68 (m, 1H), 7.59~7.25 (m, 5H), 6.81 (d, 1H), 6.71 (d, 1H), 3.91 (s, 3H), 3.49 (bs, 4H), 3.07-2.85 (m, 8H).

Example 43

Preparation of 8-{4-[2-(6-chloro-1-benzofuran-3-yl) ethyl]-1-piperazinyl}-quinoline ("Compound 5")

Step 1: To a stirred solution of methyl-4-chloro-2-hydroxy-benzoate (18. 6 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was then filtered and concentrated. The oily residue was extracted with chloroform and washed well with water. The organic layer was dried over anhydrous $MgSO_4$ and filtered. It was concentrated and taken to the next step without any purification. White oil; Yield: 27.0 g (99%); (M+H): 273.

Step 2: The methyl-2-(ethoxy-2-oxoethoxy)-4-chlorobenzoate obtained from the step 1, (13.6 g, 50 mmol) was dissolved in THF:MeOH (1:1) (300 ml) to which was added 5N NaOH (100 ml). The reaction mixture was refluxed for 24 hrs and cooled to room temperature. Afterwards, it was concentrated to dryness and dissolved in water. The aqueous layer was acidified with con. HCl and the separated solid were filtered. It was then washed well with water and dried. The product was taken to the next step without any purification. White solid; Yield: 10.0 g (86%); (M+H): 231.

Step 3: The 2-(carboxymethoxy)-4-chloro-benzoic acid compound obtained from the step 2 (11.5 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 6-chloro-benzofuran-3 (2H)-one, precipitated from the reaction mixture. It was filtered and washed well with water. It was dried at 40° C. and used for the next step without further purification. Yield: 5.8 g (69%); (M+H): 169.

Step 4: A mixture of 6-chloro-benzofuran-3 (2H)-one (1.68 g, 10 mmol) and (carboxymethylene)triphenylphosphorane (5.22 g, 15 mmol) was refluxed in toluene (100 ml) for 48 hrs. Afterwards, the reaction mixture was concentrated and loaded over a silica-gel column. The column was eluted with hexane (500 ml) and then with 25% ethyl acetate. The product, ethyl(6-chloro-1-benzofuran-3-yl)acetate, was obtained as a white oil. Yield: 2.1 g (87%); (M+H): 239.

Step 5: To a stirred suspension of LiAlH$_4$ (200 mg, excess) in THF at 0° C., ethyl(6-chloro-1-benzofuran-3-yl) acetate (1.19 g, 50 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product obtained, 2-(6-chloro-1-benzofuran-3-yl)ethanol, was a white oil was pure enough and taken to next step without purification. Yield: 900 mg (91%); (M+H): 197.

Step 6: To a stirred solution of 2-(6-chloro-1-benzofuran-3-yl)ethanol (980 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to next step without any purification. A mixture of tosylate (350 mg. 1 mmol) (obtained by the above mentioned process) and 8-piperazino-quinoline (213 mg, 1 mmol) was heat at 120° C. in DMSO in the presence of N,N-diisopropylethylamine (5 ml, excess) for 24 hrs. At the end, reaction mixture was quenched with water and extracted with chloroform. The organic layer was washed with water and dried over anhydrous MgSO$_4$ and concentrated to dryness. The dark colored solid was purified by silica-gel column chromatography by eluting it initially with 70% ethyl acetate:hexane and then with 5% methanol:ethyl acetate. 8-{4-[2-(6-chloro-1-benzofuran-3-yl)ethyl]-1-piperazinyl}-quinoline was isolated as a yellow oil. Yield: 120 mg (30%); (M+H): 392; $^1$HNMR (400 MHz, CDCl$_3$):δ 8.82~8.81 (dd, J$_1$=1.7 Hz, J$_2$=1.7 Hz, 1H); 8.40~8.20 (dd, J$_1$=1.8 Hz, J$_2$=1.8 Hz, 1H); 7.46~6.92 (m, 8H); 3.50~2.70 (m, 12H).

Example 44

Preparation of 8-{4-[2-(6-chloro-1-benzofuran-3-yl) ethyl]-1-piperazinyl}-6-fluoro-quinoline ("Compound 6")

8-{4-[2-(6-chloro-1-benzofuran-3-yl)ethyl]-1-piperazinyl}-6-fluoro-quinoline_ was prepared by generally following the procedure outlined in example 5, step 6, starting from the tosylate (350 mg, 1 mmol) and 6-fluoro-8-piperazino quinoline (231 mg, 1 mmol). The product was purified by silica-gel column chromatography by eluting it initially with 80% ethyl acetate:hexane and then with 5% methanol:ethyl acetate, to yield a brown oil. Yield: 90 mg, (22%); (M+H): 410; $^1$HNMR (400 MHz, CDCl$_3$): δ 8.82~8.81 (dd, J$_1$=1.7 Hz, J$_2$=1.7 Hz, 1H); 8.05~8.03 (dd, J$_1$=1.8 Hz, J$_2$=1.8 Hz, 1H); 7.64~6.43 (m, 7H); 3.51~2.80 (m, 12H).

Example 45

Preparation of 8-{4-[2-(6-chloro-1-benzofuran-3-yl) ethyl]-1-piperazinyl}-6-chloro-quinoline ("Compound 7")

8-{4-[2-(6-chloro-1-benzofuran-3-yl)ethyl]-1-piperazinyl}-6-chloro-quinoline was prepared by generally following the procedure outlined in example 5, step 6, starting from the tosylate (350 mg, 1 mmol) and 6-chloro-8-piperazino quinoline (247 mg, 1 mmol). The product was purified by silica-gel column chromatography by eluting it initially with 80% ethyl acetate:hexane and then with 5% methanol:ethyl acetate, to yield a brown oil. Yield: 110 mg, (25%); (M+H): 427; $^1$HNMR (400 MHz, CDCl$_3$): δ 8.80~8.81 (dd, J$_1$=1.7 Hz, J$_2$=1.7 Hz, 1H); 8.22~8.23 (dd, J$_1$=1.8 Hz, J$_2$=1.8 Hz, 1H); 7.87~6.99 (m, 7H); 3.50~2.58 (m, 12H).

Example 46

Preparation of 8-{4-[2-(6-chloro-1-benzofuran-3-yl) ethyl]-1-piperazinyl}-6-methyl-quinoline ("Compound 8")

8-{4-[2-(6-chloro-1-benzofuran-3-yl)ethyl]-1-piperazinyl}-6-methyl-quinoline was prepared by following the procedure outlined in example 5, step 6, starting from the tosylate (350 mg, 1 mmol) and 6-methyl-8-piperazino quinoline (227 mg, 1 mmol). The product was purified by silica-gel column chromatography by eluting it initially with 80% ethyl acetate:hexane and then with 5% methanol:ethyl acetate, to yield a brown oil. Yield: 89 mg, (21%); (M+H): 406; $^1$HNMR (400 MHz, CDCl$_3$):δ 8.74~8.72 (dd, J$_1$=1.7 Hz, J$_2$=1.7 Hz, 1H); 8.13~7.94 (dd, J$_1$=1.8 Hz, J$_2$=1.8 Hz, 1H); 7.40~6.71 (m, 7H); 3.40~2.73 (m, 12H); 2.42 (s, 3H).

Example 47

Preparation of 8-{4-[2-(6-methoxy-1-benzofuran-3-yl)ethyl]-1-piperazinyl}-quinoline ("Compound 9")

Step 1: To a stirred solution of methyl-4-methoxy-2-hydroxy-benzoate (18.2 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to the next step without any purification. White oil; Yield: 24.0 g (89%); (M+H): 269.

Step 2: The methyl-2-(ethoxy-2-oxoethoxy)-4-methoxybenzoate obtained from the step 1, (13.4 g, 50 mmol) was dissolved in THF:MeOH (1:1) (300 ml) to which was added 5N NaOH (100 ml). The reaction mixture was refluxed for 24 hrs and cooled to room temperature. Afterwards, it was concentrated to dryness and dissolved in water. The aqueous layer was acidified with con. HCl and the separated solid was filtered. The product was then washed well with water and dried. The product was taken to step without any purification. White solid; Yield: 8.5 g (75%); (M+H): 227.

Step 3: The 2-(carboxymethoxy)-4-methoxy-benzoic acid compound obtained from the step 2 (11.3 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 6-methoxy-benzofuran-3 (2H)-one, precipitated from the reaction mixture. It was filtered and washed well with water. It was dried at 40° C. and used for the next step without further purification. Yield: 4.7 g (57%); (M+H): 165.

Step 4: A mixture of 6-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. Afterwards, reaction mixture was concentrated and loaded over a silica-gel column. The column was eluted with hexane (500 ml) and then with 25% ethyl acetate. The product, ethyl(6-methoxy-1-benzofuran-3-yl)acetate, was obtained as a white oil. Yield: 1.8 g (76%); (M+H): 235.

Step 5: To a stirred suspension of LiAlH$_4$ (200 mg, excess) in THF at 0° C., ethyl(6-methoxy-1-benzofuran-3-yl)acetate (1.17 g, 5 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(6-methoxy-1-benzofuran-3-yl)ethanol, was obtained as a white oil and was pure enough to be taken to the next step without purification. Yield: 850 mg (88%); (M+H): 193.

Step 6: To a stirred solution of 2-(6-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. The product was then extracted with chloroform, washed well with 5% Na$_2$S$_2$O$_3$ solution and the organic layer dried over anhydrous MgSO$_4$. It was then filtered and concentrated. The residue was purified by silica-gel column chromatography by eluting it with 30% ethyl acetate:hexane. The product, 2-(6-methoxy-1-benzofuran-3-yl)ethyl iodide, was obtained as a brown liquid. Yield: 1.2 g (80%); (M+H): 302.

A mixture of 2-(6-methoxy-1-benzofuran-3-yl)ethyl iodide (301 mg, 1 mmol) (obtained by the above mentioned process) and 8-piperazino quinoline (213 mg, 1 mmol) was heated at 120° C. in DMSO in the presence of N,N-diisopropylethylamine (5 ml, excess) for 24 hrs. Afterwards, the reaction mixture was quenched with water and extracted with chloroform. The organic layer was washed with water and dried over anhydrous MgSO$_4$ and concentrated to dryness. The dark colored solid was purified by silica-gel column chromatography by eluting it initially with 70% ethyl acetate:hexane and then with 5% methanol:ethyl acetate. 8-{4-[2-(6-methoxy-1-benzofuran-3-yl)ethyl]-1-piperazinyl}-quinoline was isolated as yellow oil. Yield: 120 mg (31%); (M+H): 388; $^1$HNMR (400 MHz, CDCl$_3$): δ 8.82~8.81 (dd, J$_1$=1.8 Hz, J$_2$=1.8 Hz, 1H); 8.05~8.02 (dd, J$_1$=1.8 Hz, J$_2$=1.8 Hz, 1H); 7.44~6.35 (m, 8H); 3.9 (s, 3H); 3.60~2.70 (m, 12H).

Example 48

Preparation of 8-{4-[2-(6-methoxy-1-benzofuran-3-yl)ethyl]-1-piperazinyl}-6-methyl-quinoline ("Compound 10")

8-{4-[2-(6-methoxy-1-benzofuran-3-yl)ethyl]-1-piperazinyl}-6-methyl-quinoline was prepared by generally following the procedure outlined in example 9, step 6, starting from the step of 2-(6-methoxy-1-benzofuran-3-yl)ethyl iodide (301 mg, 1 mmol) and 6-methyl-8-piperazino quinoline (227 mg, 1 mmol). The product was purified by silica-gel column chromatography by initially eluting it with 80% ethyl acetate:hexane and then with 5% methanol:ethyl acetate, yielding a brown oil Yield: 210 mg (52%); (M+H): 402; $^1$HNMR (400 MHz, CDCl$_3$):δ 8.81~8.80 (dd, J$_1$=1.8 Hz, J$_2$=1.8 Hz, 1H); 8.02~7.99 (dd, J$_1$=1.8 Hz, J$_2$=1.8 Hz, 1H) 7.46~6.88 (m, 7H); 3.9 (s, 3H); 3.60~2.82 (m, 12H); 2.5 (s, 3H).

Example 49

Preparation of 8-{4-[2-(6-methoxy-1-benzofuran-3-yl)ethyl]-1-piperazinyl}-6-chloro-quinoline ("Compound 11")

8-{4-[2-(6-methoxy-1-benzofuran-3-yl)ethyl]-1-piperazinyl}-6-chloro-quinoline was prepared by generally following the procedure outlined in example 9, step 6, starting from 2-(6-methoxy-1-benzofuran-3-yl)ethyl iodide (301 mg, 1 mmol) and 6-chloro-8-piperazino quinoline (247 mg, 1 mmol). The product was purified by silica-gel column chromatography by initially eluting it with 80% ethyl acetate:hexane and then with 5% methanol:ethyl acetate, yielding a brown oil Yield: 140 mg (33%); (M+H): 422; $^1$HNMR (400 MHz, CDCl$_3$):δ 8.86~8.68 (dd, J$_1$=1.8 Hz, J$_2$=1.8 Hz, 1H); 8.02~7.99 (dd, J$_1$=1.8 Hz, J$_2$=1.8 Hz, 1H); 7.45~6.63 (m, 7H); 3.9 (s, 3H); 3.65~2.71 (m, 12H).

Example 50

Preparation of 8-{4-[2-(5-chloro-1-benzofuran-3-yl)ethyl]-1-piperazinyl}-quinoline ("Compound 12")

Step 1: To a stirred solution of methyl-5-chloro-2-hydroxy-benzoate (18. 6 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to the next step without any purification. White oil; Yield: 22.0 g (80%); (M+H): 273.

Step 2: The methyl-2-(ethoxy-2-oxoethoxy)-5-chloro-benzoate obtained from the step 1, (13.6 g, 50 mmol) was dissolved in THF:MeOH (1:1) (300 ml) and 5N NaOH (100 ml) was added. The reaction mixture was refluxed for 24 hrs and cooled to room temperature. Afterwards, it was concentrated to dryness and dissolved in water. The aqueous layer was acidified with con. HCl and the separated solid were filtered. The product was then washed well with water and dried. The product was taken to step without any purification. White solid; Yield: 8.0 g (69%); (M+H): 231.

Step 3: The 2-(carboxymethoxy)-5-chloro-benzoic acid compound obtained from the step 2 (11.5 g, 50 mmol) was dissolved in acetic anhydride (100 ml) and anhydrous sodium acetate (10.0 g, excess) was added. The reaction mixture was heated to 150° C. for 4 hrs. During this time, the reaction mixture turned dark red. The reaction mixture was cooled to room temperature and quenched carefully with ice cold water. The red solid obtained was filtered and washed well with water. The red solid was then suspended in 1 N HCl and refluxed for 2 hrs. A dark red solid, 5-chloro-benzofuran-3 (2H)-one, precipitated from the reaction mixture. It was filtered and washed well with water. It was dried at 40° C. and used for the next step without further purifications. Yield: 6.2 g (73%); (M+H): 169.

Step 4: A mixture of 5-chloro-benzofuran-3 (2H)-one (1.68 g, 10 mmol) and (carboxymethylene)triphenylphosphorane (5.22 g, 15 mmol) was refluxed in toluene (100 ml) for 48 hrs. At the end, reaction mixture was concentrated and loaded over silica-gel column. The column was eluted with hexane (500 ml) and then with 25% ethyl acetate. The product, ethyl(5-chloro-1-benzofuran-3-yl)acetate, was obtained as a white oil. Yield: 1.8 g (75%); (M+H): 239.

Step 5: To a stirred suspension of LiAlH$_4$ (200 mg, excess) in THF at 0° C., ethyl(5-chloro-1-benzofuran-3-yl)acetate (1.19 g, 50 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(5-chloro-1-benzofuran-3-yl)ethanol, was obtained as a white oil and was pure enough and be taken to the next step without purification. Yield: 850 mg (86%); (M+H): 197.

Step 6: To a stirred solution of 2-(5-chloro-1-benzofuran-3-yl)ethanol (980 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was then extracted with chloroform, washed well with 5% Na$_2$S$_2$O$_3$ and the organic layer dried over anhydrous MgSO$_4$. It was filtered and concentrated. The residue was purified by silica-gel column chromatography by eluting it with 30% ethyl acetate:hexane. The product, 2-(5-chloro-1-benzofuran-3-yl)ethyl iodide, was obtained as brown liquid; Yield: 1.2 g (80%); (M+H): 306.

A mixture of 2-(5-chloro-1-benzofuran-3-yl)ethyl iodide (305 mg. 1 mmol) (obtained by the above mentioned process) and 8-piperazino quinoline (213 mg, 1 mmol) was heated at 120° C. in DMSO in the presence of N,N-diisopropylethylamine (5 ml, excess) for 24 hrs. Afterwards, the reaction mixture was quenched with water and extracted with chloroform. The organic layer was washed with water and dried over anhydrous MgSO$_4$ and concentrated to dryness. The dark colored solid was purified by silica-gel column chromatography by initially eluting it with 70% ethyl acetate:hexane and then with 5% methanol:ethyl acetate. 8-{4-[2-(5-chloro-1-benzofuran-3-yl)ethyl]-1-piperazinyl}-quinoline was isolated as a yellow oil. Yield: 120 mg (30%); (M+H): 392; $^1$HNMR (400 MHz, CDCl$_3$): δ 8.86~8.85 (dd, J$_1$=1.8 Hz, J$_2$=1.8 Hz, 1H); 8.03~8.01 (dd, J$_1$=1.8 Hz, J$_2$=1.8 Hz, 1H); 7.57~7.10 (m, 8H); 3.51~2.50 (m, 12H).

Example 51

Preparation of 8-{4-[2-(5-chloro-1-benzofuran-3-yl) ethyl]-1-piperazinyl}-6-chloro-quinoline ("Compound 13")

8-{4-[2-(5-chloro-1-benzofuran-3-yl)ethyl]-1-piperazinyl}-6-chloro-quinoline was prepared by generally following the procedure outlined in example 12, step 6, starting from the 2-(5-chloro-1-benzofuran-3-yl)ethyl iodide (306 mg, 1 mmol) and 6-chloro-8-piperazino quinoline (247 mg, 1 mmol). The product was purified by silica-gel column chromatography by initially eluting it with 80% ethyl acetate:hexane and then with 5% methanol:ethyl acetate, yielding a brown oil. Yield: 110 mg (25%); (M+H): 427; $^1$HNMR (400 MHz, CDCl$_3$):δ 8.86~8.85 (dd, J$_1$=1.8 Hz, J$_2$=1.8 Hz, 1H); 8.03~8.01 (dd, J$_1$=1.8 Hz, J$_2$=1.8 Hz, 1H); 7.57~7.10 (m, 7H); 3.51~2.50 (m, 12H).

Example 52

Preparation of 8-{4-[2-(5-chloro-1-benzofuran-3-yl) ethyl]-1-piperazinyl}-6-methyl-quinoline ("Compound 14")

8-{4-[2-(5-chloro-1-benzofuran-3-yl)ethyl]-1-piperazinyl}-6-methyl-quinoline was prepared by generally following the procedure outlined in example 12, step 6, starting from the 2-(5-chloro-1-benzofuran-3-yl)ethyl iodide (306 mg, 1 mmol) and 6-methyl-8-piperazino quinoline (227 mg, 1 mmol). The product was purified by silica-gel column chromatography by initially eluting it with 80% ethyl acetate:hexane and then with 5% methanol:ethyl acetate, yielding a brown oil. Yield: 140 mg (34%); (M+H): 406; $^1$HNMR (400 MHz, CDCl$_3$): δ8.82~8.80 (dd, J$_1$=1.7 Hz, J$_2$=1.7 Hz, 1H), 8.03~7.80 (dd, J$_1$=1.7 Hz, J$_2$=1.7 Hz 1H), 7.60~6.70 (m, 7H), 3.48~2.81 (m, 12H), 2.5 (s, 3H).

Example 53

Preparation of 8-{4-[2-(5-fluoro-1-benzofuran-3-yl) ethyl]-1-piperazinyl}-quinoline ("Compound 15")

Step 1: To a stirred solution of 5-fluoro-2-hydroxy-methyl benzoate (17.0 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to the next step without any purification. White oil; Yield: 23.0 g (89%); (M+H): 257.

Step 2: The methyl-5-fluoro-2-(ethoxy-2-oxoethoxy)benzoate obtained from the step 1, (12.8 g, 50 mmol) was dissolved in THF:MeOH (1:1) (300 ml) and 5N NaOH (100 ml) was added. The reaction mixture was refluxed for 24 hrs and cooled to room temperature. Afterwards, it was concentrated to dryness and dissolved in water. The aqueous layer was acidified with con. HCl and the separated solid were filtered. It was then washed well with water and dried. The product was taken to the next step without any purification. White solid; Yield: 8.3 g (77%); (M+H): 215.

Step 3: The 2-(carboxymethoxy)-5-fluoro-benzoic acid compound obtained from step 2 (10.7 g, 50 mmol) was dissolved in acetic anhydride (100 ml) and anhydrous sodium acetate (10.0 g, excess) was added. The reaction mixture was heated to 150° C. for 4 hrs. During this time, the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 5-fluoro-benzofuran-3 (2H)-one, precipitated from the reaction mixture. It was filtered and washed well with water. It was dried at 40° C. and used for the next step with out further purifications. Yield: 5.8 g (76%); (M+H): 153.

Step 4: A mixture of 5-fluoro-benzofuran-3 (2H)-one (1.52 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and then with 25% ethyl acetate. The product, ethyl(5-fluoro-1-benzofuran-3-yl)acetate, was obtained as a white oil. Yield: 1.8 g (80%); (M+H): 223.

Step 5: To a stirred suspension of LiAlH$_4$ (200 mg, excess) in THF at 0° C., ethyl(5-fluoro-1-benzofuran-3-yl) acetate (1.11 g, 5 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(5-fluoro-1-benzofuran-3-yl)ethanol, was obtained as a white oil and was pure enough to be taken to the next step without purification. Yield: 820 mg (91%); (M+H): 181.

Step 6: To a stirred solution of 2-(5-fluoro-1-benzofuran-3-yl)ethanol (900 mg, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to the next step without any purification.

A mixture of tosylate (334 mg. 1 mmol) (obtained by the above mentioned process) and 8-piperazino quinoline (213 mg, 1 mmol) was heated at 120° C. in DMSO in the presence of N,N-diisopropylethylamine (5 ml, excess) for 24 hrs. At the end, reaction mixture was quenched with water and extracted with chloroform. The organic layer was washed with water and dried over anhydrous MgSO$_4$ and concentrated to dryness. The dark colored solid was purified by silica-gel column chromatography by initially eluting it with 70% ethyl acetate:hexane and then with 5% methanol:ethyl acetate. 8-{4-[2-(5-fluoro-1-benzofuran-3-yl)ethyl]-1-piperazinyl}-quinoline was isolated as a yellow solid. mp 54° C.; Yield: 90 mg (21%); (M+H): 412; $^1$H NMR: δ 11.6 9bs, 1H), 9.2 (bs, 1H), 8.7 (bs, 1H), 8.0-7.2 (m, 9H), 4.0-3.3 (m, 12H).

Example 54

Preparation of 8-{4-[2-(5-fluoro-1-benzofuran-3-yl) ethyl]-1-piperazinyl}-6-methoxy-quinoline ("Compound 16")

8-{4-[2-(5-fluoro-1-benzofuran-3-yl)ethyl]-1-piperazinyl}-6-methoxy-quinoline was prepared by following the procedure outlined in example 15, step 6, starting from the tosylate (334 mg, 1 mmol) and 6-methoxy-8-pierazino quinoline (243 mg, 1 mmol). The product was purified by silica-gel column chromatography by eluting it initially with 80% ethyl acetate:hexane and then with 5% methanol:ethyl acetate, yielding a yellow solid. MP: 80° C. (HCl salt); Yield: 110 mg, (25%); (M+H): 406; $^1$H NMRδ11.3 (bs, 1H), 8.9 (bs, 1H), 8.43 (bs, 1H), 8.32 (s, 1H), 8.03 (s, 1H), 7.7-7.11 (m, 5H), 3.9 (s, 3H), 3.77-3.25 (m, 12H).

Example 55

Preparation of 8-{4-[2-(5-fluoro-1-benzofuran-3-yl) ethyl]-1-piperazinyl}-6-fluoro-quinoline ("Compound 17")

8-{4-[2-(5-fluoro-1-benzofuran-3-yl)ethyl]-1-piperazinyl}-6-fluoro-quinoline was prepared by following the procedure outlined in example 15, step 6, starting from the tosylate (334 mg, 1 mmol) and 6-fluoro-8-pierazino quinoline (231 mg, 1 mmol). The product was purified by silica-gel column chromatography by eluting it initially with 80% ethyl acetate; hexane and latter with 5% methanol; ethyl acetae. Yellow solid; MP: 55° C. (HCl salt); Yield: 140 mg, 32%; 394 (M+H); $^1$H NMR: δ 11.5 (bs, 1H), 8.8 9m, 1H), 8.43 (dd, 1H), 8.04 (s, 1H), 7.7-7.23 (m, 6H), 4.19-3.20 (m, 12H).

Example 56

Preparation of 8-{4-[2-(7-methoxy-1-benzofuran-3-yl)ethyl]-1-piperazinyl}-quinoline ("Compound 18")

Step 1: A mixture of 7-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and then with 25% ethyl acetate. The product, ethyl(7-methoxy-1-benzofuran-3-yl)acetate, was obtained as a white oil. Yield: 1.9 g (81%); (M+H): 235.

Step 2: To a stirred suspension of LiAlH$_4$ (200 mg, excess) in THF at 0° C., ethyl(7-methoxy-1-benzofuran-3-yl)acetate (1.17 g, 5 mmol) in THF (20 mL) was added slowly. After the addition, the reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(7-methoxy-1-benzofuran-3-yl)ethanol, was obtained as a white oil and was pure enough to be taken to the next step without purification. Yield: 800 mg (83%); (M+H): 193.

Step 3: To a stirred solution of 2-(7-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. The mixture was then extracted with chloroform, washed well with 5% Na$_2$S$_2$O$_3$ solution and the organic layer dried over anhydrous MgSO$_4$. It was then filtered and concentrated. The residue was purified by silica-gel column chromatography by eluting it with 30% ethyl acetate:hexane. The product, 2-(7-methoxy-1-benzofuran-3-yl)ethyl iodide, was obtained as a brown liquid. Yield: 1.3 g (86%); (M+H): 302.

A mixture of 2-(7-methoxy-1-benzofuran-3-yl)ethyl iodide (301 mg. 1 mmol) (obtained by the above mentioned process) and 8-piperazino quinoline (213 mg, 1 mmol) was heated at 120° C. in DMSO in the presence of N,N-diisopropylethylamine (5 ml, excess) for 24 hrs. Afterwards, the reaction mixture was quenched with water and extracted with chloroform. The organic layer was washed with water and dried over anhydrous MgSO$_4$ and concentrated to dryness. The dark colored low melting solid was purified by silica-gel column chromatography by initially eluting it with 70% ethyl acetae:hexane and then with 5% methanol:ethyl acetate. 8-{4-[2-(7-methoxy-1-benzofuran-3-yl)ethyl]-1-piperazinyl}-quinoline was isolated as a dark brown low melting solid. Yield: (HCl salt) 90 mg (21%); (M+H): 388; $^1$H NMR: δ☐11.9 (bs, 1H), 9.2 (d, 1H), 9.0 (bs 1H), 8.2 (m, 2H), 7.9 (s1H), 7.84 (m, 2H), 7.45 (d, 1H), 7.21 (t, 1H), 6.98 (d, 1H), 4.01 9s, 3H), 3.77 (m, 4H), 3.67 9m, 2H), 3.59 (m, 4H), 3.3 (m, 2H).

Example 57

Preparation of 8-{4-[2-(7-methoxy-1-benzofuran-3-yl)ethyl]-1-piperazinyl}-6-methoxy-quinolinen ("Compound 19")

8-{4-[2-(7-methoxy-1-benzofuran-3-yl)ethyl]-1-piperazinyl}-6-methoxy-quinoline was prepared by generally following the procedure outlined in example 18, step 3, starting from 2-(7-methoxy-1-benzofuran-3-yl)ethyl iodide (301 mg, 1 mmol) and 6-methoxy-8-piperazino quinoline (243 mg, 1 mmol). The product was purified by silica-gel column chromatography by eluting it initially with 80% ethyl acetate:hexane and then with 5% methanol:ethyl acetate. A HCl salt was prepared, yielding a green spongy solid. MP: 86° C.; Yield: 300 mg, (66%); (M+H): 418; $^1$H NMR δ☐11.8 (bs, 1H), 9.0 (bs, 1H), 8.9 (bs, 1H), 8.0 (s, 1H), 7.8 (m, 1H), 7.5 (m, 2H), 7.3 (m, 2H), 6.9 (d, 1H), 4.0 (s, 6H), 3.8 (m, 6H), 3.4-3.1 (m, 6H).

Example 58

Preparation of 8-{4-[2-(7-methoxy-1-benzofuran-3-yl)ethyl]-1-piperazinyl}-6-chloro-quinoline ("Compound 20")

8-{4-[2-(7-methoxy-1-benzofuran-3-yl)ethyl]-1-piperazinyl}-6-chloro-quinoline was prepared by generally following the procedure outlined in example 18, step 3, starting from 2-(7-methoxy-1-benzofuran-3-yl)ethyl iodide (301 mg, 1 mmol) and 6-chloro-8-piperazino quinoline (247 mg, 1 mmol). The product was purified by silica-gel column chromatography by eluting it initially with 80% ethyl acetate:hexane and then with 5% methanol:ethyl acetate. A HCl salt was prepared, yielding a green spongy solid. mp 248° C.; Yield: 320 mg (69%); (M+H): 424; $^1$H NMR δ 11.8 (bs, 1H), 9.0 (d, 1H), 8.5 (d, 1H), 8.0 (s, 1H), 7.8-7.0 (m, 5H), 6.8 (d, 1H), 4.2 (d, 2H), 3.9 (s, 3H), 3.7-3.2 (m, 10H).

Example 59

Preparation of 8-{4-[2-(5-methoxy-1-benzofuran-3-yl)ethyl]-1-piperazinyl}-quinoline ("Compound 21")

Step 1: To a stirred solution of methyl-5-methoxy-2-hydroxy benzoate (18. 2 g, 0.1 mol) and anhydrous potassium carbonate (50.0 g, excess) in acetone (500 ml) ethyl bromoacetate (16.7 g, 0.1 mol) was added. The reaction mixture was refluxed for 24 hrs and cooled to room temperature. It was filtered and concentrated. The oily residue was extracted with chloroform and washed well with water. The organic layer was dried over anhydrous MgSO$_4$ and filtered. It was concentrated and taken to the next step without any purification. Yellow oil; Yield: 21.0 g (78%); (M+H): 269.

Step 2: The methyl-2-(ethoxy-2-oxoethoxy)-5-methoxy-benzoate obtained from step 1, (13.4 g, 50 mmol) was dissolved in THF:MeOH (1:1) (300 ml) and 5N NaOH (100 ml) was added. The reaction mixture was refluxed for 24 hrs and cooled to room temperature. At the end it was concentrated to dryness and dissolved in water. The aqueous layer was acidified with con. HCl and the separated solid were filtered. It was then washed well with water and dried. The product was taken to the next step without any purification. White solid; Yield: 10.2 g (90%); MP: 150-153° C.; (M+H): 227.

Step 3: The 2-(carboxymethoxy)-5-methoxy-benzoic acid compound obtained from the step 2 (11.3 g, 50 mmol) was dissolved in acetic anhydride (100 ml) and anhydrous sodium acetate (10.0 g, excess) was added. The reaction mixture was heated to 150° C. for 4 hrs. During this time the reaction mixture turned dark red. The reaction mixture was cooled to room temperature and quenched carefully with ice cold water. The red solid obtained was filtered and washed well with water. The red solid obtained was suspended in 1 N HCl and refluxed for 2 hrs. A dark red solid, 5-methoxy-benzofuran-3 (2H)-one, precipitated from the reaction mixture. It was filtered and washed well with water. It was dried at 40° C. and used for the next step without further purification. Yield: 6.2 g (75%); (M+H): 165.

Step 4: A mixture of 5-methoxy-benzofuran-3 (2H)-one (1.64 g, 10 mmol) and (carboxymethylene)triphenylphosphorane (5.22 g, 15 mmol) was refluxed in toluene (100 ml) for 48 hrs. At the end, reaction mixture was concentrated and loaded over a silica-gel column. The column was eluted with hexane (500 ml) and then with 25% ethyl acetate. The product, ethyl(5-methoxy-1-benzofuran-3-yl)acetate, was obtained as a white oil. Yield: 1.6 g (68%); (M+H): 235.

Step 5: To a stirred suspension of LiAlH$_4$ (200 mg, excess) in THF at 0° C., ethyl(5-methoxy-1-benzofuran-3-yl)acetate (1.17 g, 5 mmol) in THF (20 ml) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(5-methoxy-1-benzofuran-3-yl)ethanol, was obtained as a white oil and was pure enough to be taken to the next step without purification, yielding a yellow oil. Yield: 900 mg (93%); (M+H): 193.

Step 6: To a stirred solution of 2-(5-methoxy-1-benzofuran-3-yl)ethanol (960 mg, 5 mmol) in anhydrous THF (50 ml), triphenylphosphine (1.572 g, 6 mmol), iodine (1.518 g, 6 mmol) and imidazole (408 mg, 6 mmol) were added at room temperature. The reaction mixture was stirred at room temperature for 4 hrs and quenched with water. It was then extracted with chloroform, washed well with 5% Na$_2$S$_2$O$_3$ and the organic layer dried over anhydrous MgSO$_4$. It was filtered and concentrated. The residue was purified by silica-gel column chromatography by eluting it with 30% ethyl acetate:hexane. The product, 2-(5-methoxy-1-benzofuran-3-yl)ethyl iodide, was obtained as a brown liquid. Yield: 1.1 g (73%); (M+H): 302.

A mixture of 2-(5-methoxy-1-benzofuran-3-yl)ethyl iodide (301 mg. 1 mmol) (obtained by the above mentioned process) and 8-piperazino quinoline(213 mg, 1 mmol) was heated at 120° C. in DMSO in the presence of N,N-diisopropylethylamine (5 ml, excess) for 24 hrs. At the end, reaction mixture was quenched with water and extracted with chloroform. The organic layer was washed with water and dried over anhydrous MgSO$_4$ and concentrated to dryness. The dark colored solid was purified by silica-gel column chromatography by eluting it initially with 70% ethyl acetae:hexane and then with 5% methanol:ethyl acetate. 8-{4-[2-(5-methoxy-1-benzofuran-3-yl)ethyl]-1-piperazinyl}-quinoline was isolated as brown solid. mp 78° C.; Yield: 120 mg (31%); (M+H): 388; $^1$HNMR (400 MHz, CDCl$_3$): δ 8.90~8.88 (dd, J$_1$=1.7 Hz, J$_2$=1.7 Hz,, 1H); 8.13~8.10 (dd, J$_1$=1.8 Hz, J$_2$=1.8 Hz, 1H); 7.51~6.88 (m, 8H); 3.68 (s, 3H); 3.68~2.82 (m, 12H).

Example 60

Preparation of 8-{4-[2-(5-methoxy-1-benzofuran-3-yl)ethyl]-1-piperazinyl}-6-chloro-quinoline ("Compound 22")

8-{4-[2-(5-methoxy-1-benzofuran-3-yl)ethyl]-1-piperazinyl}-6-chloro-quinoline was prepared by generally following the procedure outlined in example 21, step 6, starting from 2-(5-methoxy-1-benzofuran-3-yl)ethyl iodide (301 mg, 1 mmol) and 6-chloro-8-piperazino quinoline (247 mg, 1 mmol). The product was purified by silica-gel column chromatography by eluting it initially with 80% ethyl acetate:hexane and then with 5% methanol:ethyl acetate, yield a brown solid. MP: 72° C.; Yield: 130 mg (30%); (M+H): 422; $^1$HNMR (400 MHz, CDCl$_3$): δ☐8.86~8.84 (dd, J$_1$=1.7 Hz, J$_2$=1.7 Hz, 1H); 8.05~8.02 (dd, J$_1$=1.7 Hz, J$_2$=1.7 Hz, 1H); 7.60~6.88 (m, 7H); 3.86 (s, 3H); 3.69~2.57 (m, 12H).

Example 61

Preparation of 8-{4-[2-(5-methoxy-1-benzofuran-3-yl)ethyl]-1-piperazinyl}-6-methyl-quinoline ("Compound 23")

8-{4-[2-(5-methoxy-1-benzofuran-3-yl)ethyl]-1-piperazinyl}-6-methyl-quinoline was prepared by generally following the procedure outlined in example 21, step 6, starting from 2-(5-methoxy-1-benzofuran-3-yl)ethyl iodide (301 mg, 1 mmol) and 6-methyl-8-piperazino quinoline (227 mg, 1 mmol). The product was purified by silica-gel column chromatography by eluting it initially with 80% ethyl acetate:hexane and then with 5% methanol:ethyl acetate, yielding a brown oil. Yield: 150 mg (37%); (M+H): 402; $^1$HNMR (400 MHz, CDCl$_3$): δ 8.82~8.73 (dd, J$_1$=1.7 Hz, J$_2$=1.7 Hz, 1H); 8.03~802 (dd, J$_1$=1.7 Hz, J$_2$=1.7 Hz, 1H), 8.00~6.88 (m, 7H); 3.87 (s, 3H) 3.49~2.57 (m, 12H), 2.5 (s, 3H).

Example 62

Preparation of 8-{4-[2-(5-methoxy-1-benzofuran-3-yl)ethyl]-1-piperazinyl}-6-isopropyl-quinoline ("Compound 24")

8-{4-[2-(5-methoxy-1-benzofuran-3-yl)ethyl]-1-piperazinyl}-6-isopropyl-quinoline was prepared by generally following the procedure outlined in example 21, step 6, starting from 2-(5-methoxy-1-benzofuran-3-yl)ethyl iodide (301 mg, 1 mmol) and 6-isopropyl-8-piperazino quinoline (255 mg, 1 mmol). The product was purified by silica-gel column chromatography by eluting it initially with 80% ethyl acetate:hexane and then with 5% methanol:ethyl acetate, yielding a brown oil. Yield: 90 mg (20%); (M+H): 430; $^1$HNMR (400 MHz, CDCl$_3$): δ 8.83~8.12 (dd, J$_1$=1.8 Hz, J$_2$=1.8 Hz, 1H), 8.08~804 (dd,J$_1$=1.8 Hz, J$_2$=1.8 Hz, 1H), 7.75~6.70 (m, 7H), 3.84 (s, 3H), 3.50~2.86 (m, 12H), 2.90~3.01 (m, 1H), 1.34~1.33 (d, 7 Hz, 6H).

Example 63

Preparation of 8-{4-[2-(5-methoxy-1-benzofuran-3-yl)ethyl]-1-piperazinyl}-6-methoxy-quinoline ("Compound 25")

8-{4-[2-(5-methoxy-1-benzofuran-3-yl)ethyl]-1-piperazinyl}-6-methoxy-quinoline was prepared by generally following the procedure outlined in example 21, step 6, starting from 2-(5-methoxy-1-benzofuran-3-yl)ethyl iodide (301 mg, 1 mmol) and 6-methoxyl-8-piperazino quinoline (243 mg, 1 mmol). The product was purified by silica-gel column chromatography by eluting it initially with 80% ethyl acetate:hexane and then with 5% methanol:ethyl acetate, yielding a brown oil. Yield: 90 mg, (21%); (M+H): 418; $^1$HNMR (400 MHZ, CDCl$_3$): δ 8.73~8.71 (dd, J$_1$=1.7 Hz, J$_2$=1.7 Hz, 1H) 8.03~8.00 (dd, J$_1$=1.7 Hz, J$_2$=1.7 Hz, 1H), 7.50~6.71 (m, 7H); 3.91 (s, 3H), 3.87 (s, 3H), 3.55~2.82 (12H).

Example 64

Preparation of 8-{4-[2-(5-methoxy-1-benzofuran-3-yl)ethyl]-1-piperazinyl}-6-fluoro-quinoline ("Compound 26")

8-{4-[2-(5-methoxy-1-benzofuran-3-yl)ethyl]-1-piperazinyl}-6-fluoro-quinoline was prepared by following the procedure outlined in example 21, step 6, starting from 2-(5-methoxy-1-benzofuran-3-yl)ethyl iodide (301 mg, 1 mmol) and 6-fluoro-8-piperazino quinoline (231 mg, 1 mmol). The product was purified by silica-gel column chromatography by eluting it initially with 80% ethyl acetate:hexane and then with 5% methanol:ethyl acetate, yielding a brown low melting solid. Yield: 130 mg (32%); (M+H): 406; $^1$HNMR (400 MHz, CDCl$_3$); δ 8.83~8.82 (dd, J$_1$=1.6 Hz, J$_2$=1.6 Hz, 1H); 8.06~8.05 (dd, J$_1$=1.7 Hz, J$_2$=1.7 Hz, 1H); 7.60~6.88 (m, 7H); 3.86 (s, 3H); 3.66~3.56 (broad s, 4H); 2.93~2.82 (m, 8H).

Example 65

Preparation of 8-{4-[2-(1-benzofuran-3-yl)propyl]-1-piperazinyl}quinoline ("Compound 27")

Step 1: A mixture of benzofuran-3 (2H)-one (1.34 g, 10 mmol) and ethyl-2-(triphenylphosphoranylidene)propionate (5.436 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, ethyl(-1-benzofuran-3-yl)propanoate, was obtained as a white oil. Yield: 1.6 g (67%); (M+H): 219.

Step 2: To a stirred suspension of LiAlH$_4$ (200 mg, excess) in THF at 0° C., ethyl(-1-benzofuran-3-yl)propanoate (1.09 g, 5 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(1-benzofuran-3-yl)-1-propanol, was obtained as a white oil pure enough to be taken to the next step without purification. Yield: 700 mg (79%); (M+H): 177.

Step 3: To a stirred solution of 2-(1-benzofuran-3-yl)-1-propanol (880 mg, 5 mmol) in anhydrous pyridine (20 ml), p-toluenesulfonyl chloride (1.14 g, 6.0 mmol) was added.

The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to the next step without any purification.

A mixture of tosylate (331 mg. 1 mmol) (obtained by the above mentioned process) and 8-piperazino quinoline (213 mg, 1 mmol) was heat at 120° C. in DMSO in the presence of N,N-diisopropylethylamine (5 ml, excess) for 24 hrs. Afterwards, reaction mixture was quenched with water and extracted with chloroform. The organic layer was washed with water and dried over anhydrous MgSO$_4$ and concentrated to dryness. The dark colored solid was purified by silica-gel column chromatography by eluting it with 70% ethyl acetate:hexane 0.8-{4-[2-(1-benzofuran-3-yl)propyl]-1-piperazinyl}quinoline was isolated as a yellow oil. Yield: 50 mg (13%); (M+H): 372; $^1$HNMR (400 MHZ, CDCl$_3$): δ 8.88~8.87 (dd, J$_1$=1.8 Hz, J$_2$=1.8 Hz, 1H); 8.11~8.09 (dd, J$_1$=1.8 Hz, J$_2$=1.8 Hz, 1H); 7.65~6.92 (m, 9H); 3.54~2.58 (m, 11H); 1.45~1.43 (d, J=7.0 Hz, 3H).

Example 66

Preparation of 8-{4-[2-(1-benzofuran-3-yl)propyl]-1-piperazinyl}-6-chloro-quinoline ("Compound 28")

8-{4-[2-(1-benzofuran-3-yl)propyl]-1-piperazinyl}-6-chloro-quinoline was prepared by generally following the procedure outlined in example 27, step 3, starting from the tosylate (example 27, step 3) (331 mg, 1 mmol) and 6-chloro-8-piperazino quinoline (247 mg, 1 mmol). The product was purified by silica-gel column chromatography by eluting it initially with 80% ethyl acetate:hexane and latter with 5% methanol:ethyl acetate, yielding a brown oil. Yield: 40 mg (10%); (M+H): 406; $^1$HNMR (400 MHz, CDCl$_3$): δ 8.85~8.83 (dd, J$_1$=1.8 Hz, J$_2$=1.8 Hz, 1H); 8.01~7.99 (dd, J$_1$=1.8 Hz, J$_2$=1.8 Hz, 1H), 7.73~6.83 (m, 8H); 3.50~2.56 (m, 11H); 1.44~1.41 (d, J=7.0 Hz, 3H).

Example 67

Preparation of 8-{4-[2-(1-benzofuran-3-yl)propyl]-1-piperazinyl}-6-fluoro-quinoline ("Compound 29")

8-{4-[2-(1-benzofuran-3-yl)propyl]-1-piperazinyl}-6-fluoro-quinoline was prepared by generally following the procedure outlined in example 27, step 3, starting from the tosylate (example 27, step 3) (331 mg, 1 mmol) and 6-fluoro-8-piperazino quinoline (231 mg, 1 mmol). The product was purified by silica-gel column chromatography by eluting it initially with 80% ethyl acetate:hexane and then with 5% methanol:ethyl acetate, yielding a brown oil. Yield: 45 mg (11%); (M+H): 390; $^1$HNMR (400 MHz, CDCl$_3$): δ 8.81~8.80 (dd, J$_1$=1.7 Hz, J$_2$=1.7 Hz 1H); 8.12~8.01 (dd, J$_1$=1.8 Hz, J$_2$=1.8 Hz, 1H), 7.65~6.88 (m, 8H); 3.50~2.61 (m, 11H); 1.44~1.43 (d, J=7.0 Hz, 3H).

Example 68

Preparation of 8-{4-[2-(1-benzofuran-3-yl)propyl]-1-piperazinyl}-6-methyl-quinoline ("Compound 30")

8-{4-[2-(1-benzofuran-3-yl)propyl]-1-piperazinyl}-6-methyl-quinoline was prepared by generally following the procedure outlined in example 27, step 3, starting from the tosylate (example 27, step 3) (331 mg, 1 mmol) and 6-methyl-8-piperazino quinoline (227 mg, 1 mmol). The product was purified by silica-gel column chromatography by eluting it initially with 80% ethyl acetate:hexane and then with 5% methanol:ethyl acetate, yielding a brown oil. Yield: 60 mg (15%); (M+H): 386; $^1$HNMR (400 MHz, CDCl$_3$): δ 8.81~880 (dd, J$_1$=1.7 Hz, J$_2$=1.7 Hz, 1H); 8.01~8.00 (dd, J$_1$=1.7 Hz, J$_2$=1.7 Hz, 1H); 7.66~6.93 (m, 8H); 3.50~2.47 (m, 11H); 2.48 (s, 3H); 1.43~1.40 (d, J=7.0 Hz, 3H).

Example 69

Preparation of 8-{4-[2-(7-methoxy-1-benzofuran-3-yl)propyl]-1-piperazinyl}quinoline ("Compound 31")

Step 1: A mixture of 7-methoxy-benzofuran-3 (2H)-one (1.64 g, 10 mmol) and ethyl-2-(triphenylphosphoranylidene) propionate (5.436 g, 15 mmol) was refluxed in toluene (100 ml) for 48 hrs. At the end, the reaction mixture was concentrated and loaded over a silica-gel column. The column was eluted with hexane (500 ml) and later with 25% ethyl acetate. The product, ethyl(7-methoxy-1-benzofuran-3-yl) propanoate, was obtained as a white oil. Yield: 1.9 g (76%); (M+H): 249.

Step 2: To a stirred suspension of LiAlH$_4$ (200 mg, excess) in THF at 0° C., ethyl(7-methoxy-1-benzofuran-3-yl)propanoate (1.24 g, 5 mmol) in THF (20 mL) was added slowly. After the addition, reaction mixture was stirred at room temperature for 1 hr and quenched with saturated NH$_4$Cl solution. The product was extracted with chloroform and washed well with water. It was dried over anhydrous MgSO$_4$, filtered and concentrated. The product, 2-(7-methoxy-1-benzofuran-3-yl)-1-propanol, was obtained as a white oil pure enough to be taken to the next step without purification. Yield: 900 mg (87%); (M+H): 207.

Step 3: To a stirred solution of 2-(7-methoxy-1-benzofuran-3-yl)-1-propanol (1.03 g, 5 mmol) in anhydrous pyridine (20 ml), p-toluenesulfonyl chloride (1.14 g, 6.0 mmol) was added. The reaction mixture was kept at 0° C. for 48 hrs and quenched with ice cold water. The reaction mixture was extracted with chloroform, washed well with water and dried over anhydrous MgSO$_4$. It was filtered and concentrated. The crude product obtained was taken to next step without any purification.

A mixture of tosylate (360 mg. 1 mmol) (obtained by the above mentioned process) and 8-piperazino quinoline (213 mg, 1 mmol) was heated at 120° C. in DMSO in the presence of N,N-diisopropylethylamine (5 ml, excess) for 24 hrs. Afterwards, the reaction mixture was quenched with water and extracted with chloroform. The organic layer was washed with water and dried over anhydrous MgSO$_4$ and concentrated to dryness. The dark colored solid was purified by silica-gel column chromatography by eluting it initially with 70% ethyl acetae:hexane and then with 5% methanol: ethyl acetate. 8-{4-[2-(7-methoxy-1-benzofuran-3-yl)propyl]-1-piperazinyl}quinoline was isolated as a yellow solid. A HCl salt was prepared. mp 192° C.; Yield: 315 mg (72%); (M+H): 402; 10.1 (bs, 1H), 8.95 (d, 1H), 8.51 (bs, 1H), 8.01 (s, 1H), 7.7-7.58 (m, 3H), 7.41 9d, 1H), 7.39 (bs, 1H), 7.23 (t, 1H), 6.97 (d, 1H), 3.9 (s, 3H), 3.7-3.25 (m, 11H), 1.46 (d, 3H).

Example 70

Preparation of 8-{4-[2-(7-methoxy-1-benzofuran-3-yl)propyl]-1-piperazinyl}-6-methyl-quinoline ("Compound 32")

8-{4-[2-(7-methoxy-1-benzofuran-3-yl)propyl]-1-piperazinyl}-6-chloro-quinoline was prepared by generally following the procedure outlined in example 31, step 3, starting from the tosylate (example 31, step 3) (360 mg, 1 mmol) and 6-methyl-8-piperazino quinoline (227 mg, 1 mmol). The product was purified by silica-gel column chromatography by eluting it initially with 80% ethyl acetate:hexane and then with 5% methanol:ethyl acetate, yielding a brown oil; Yield: 45 mg (10%); (M+H): 416; $^1$HNMR (400 MHz, CDCl$_3$): δ 8.81~8.79 (dd, $J_1$=1.8 Hz, $J_2$=1.8 Hz, 1H); 8.01~7.99 (dd, $J_1$=1.8 Hz, $J_2$=1.8 Hz, 1H); 7.32~6.80 (m, 7H); 3.9 (s, 3H); 3.65~2.80 (m, 11H); 2.39 (s, 3H); 1.44~1.42 (d, J=7.0 Hz, 3H)

Example 71

Preparation of 8-{4-[2-(7-methoxy-1-benzofuran-3-yl)propyl]-1-piperazinyl}-6-chloro-quinoline ("Compound 33")

8-{4-[2-(7-methoxy-1-benzofuran-3-yl)propyl]-1-piperazinyl}-6-chloro-quinoline was prepared by generally following the procedure outlined in example 31, step 3, starting from the tosylate (example 31, step 3) (360 mg, 1 mmol) and 6-chloro-8-piperazino quinoline (247 mg, 1 mmol). The product was purified by silica-gel column chromatography by eluting it initially with 80% ethyl acetate:hexane and then with 5% methanol:ethyl acetate. A HCl salt was prepared, yielding a greenish yellow solid. MP: 55-58° C.; Yield: 270 mg (57%); (M+H): 438.

Example 72

Preparation of 8-{4-[2-(7-methoxy-1-benzofuran-3-yl)propyl]-1-piperazinyl}-6-methyl-quinoline ("Compound 34")

8-{4-[2-(7-methoxy-1-benzofuran-3-yl)propyl]-1-piperazinyl}-6-methyl-quinoline was prepared by generally following the procedure outlined in example 31, step 3, starting from the tosylate (example 31, step 3) (360 mg, 1 mmol) and 6-methyl-8-piperazino quinoline (227 mg, 1 mmol). The product was purified by silica-gel column chromatography by eluting it initially with 80% ethyl acetate:hexane and latter with 5% methanol:ethyl acetate, yielding a brown oil. Yield: 120 mg (28%); (M+H): 416; $^1$HNMR (400 MHz, CDCl$_3$): δ 8.69 (d, 1H), 8.01 (d, 1H), 7.56 (s, 1H) , 7.33 (m, 1H), 7.26-6.74 (m, 6H), 3.56~2.78 (m, 11H); 2.39 (s, 3H); 1.44~1.42 (d, J=7.0 Hz, 3H). The racemic mixture was separated by preparative HPLC using a chiral column.

Example 73

Preparation of 8-{4-[2-(7-methoxy-1-benzofuran-3-yl)-1-methylethyl)piperazin-1-yl]quinoline ("Compound 35")

Step 1: A mixture of 7-methoxy-benzofuran-3 (2H)-one (1.64 g, 10 mmol) and 1-triphenylphosphoranylidene-2-propanone (4.77 g, 15 mmol) was refluxed in toluene (100 ml) for 48 hrs. At the end, reaction mixture was concentrated and loaded over a silica-gel column. The column was eluted with hexane (500 ml) and later with 25% ethyl acetate. The product, 1-(7-methoxy-1-benzofuran-3-yl)acetone, was obtained as a red oil. Yield: 1.4 g (68%); (M+H): 205.

Step 2: To a stirred mixture of 1-(7-methoxy-1-benzofuran-3-yl)acetone (204 mg, 1 mmol) and 8-piperazino quinoline (213.0 mg, 1 mmol) in 1,2-dichloroethane (100 ml) and acetic acid (1 ml), sodium triacetoxyborohydride (422 mg, 2 mmol) was added at room temperature. Reaction mixture was stirred at room temperature for 72 hrs. At the end, the reaction mixture was neutralized with 10% NaHCO$_3$ and extracted with chloroform. The organic layer was dried over anhydrous MgSO$_4$, filtered and concentrated. The product obtained was purified by silica-gel column chromatography by eluting it initially with 80% ethyl acetate:hexane and then with 5% methanol:ethyl acetate, yielding a yellow oil. Yield: 60 mg (14%); (M+H): 402; $^1$HNMR (400 MHz, CDCl$_3$): δ 8.90~8.14 (dd, $J_1$=1.8 Hz, $J_2$=1.8 Hz, 1H); 8.13~7.56 (dd, $J_1$=1.8 Hz, $J_2$=1.8 Hz, 1H); 7.46~6.80 (m, 8H); 4.01 (s, 3H); 3.51~1.60 (m, 11H); 1.14(d, J=6.0 Hz, 3H).

Example 74

Preparation of 6-methoxy-8-{4-[2-(7-methoxy-1-benzofuran-3-yl)-1-methylethyl)piperazin-1-yl]quinoline ("Compound 36")

6-methoxy-8-{4-[2-(7-methoxy-1-benzofuran-3-yl)-1-methylethyl)piperazin-1-yl]quinoline was prepared by generally following the procedure outlined in example 35, step 2, starting from the 1-(7-methoxy-1-benzofuran-3-yl)acetone (204 mg, 1 mmol) and 6-methoxy-8-piperazino quinoline (243.0 mg, 1 mmol) in 1,2-dichloroethane (100 ml) and acetic acid (1 ml), sodium triacetoxyborohydride (422 mg, 2 mmol). The product was purified by silica-gel column chromatography by eluting it initially with 80% ethyl acetate:hexane and then with 5% methanol:ethyl acetate, yielding a brown semi-solid. Yield: 75 mg (17%); (M+H): 432.

Example 75

Preparation of 6-methyl-8-{4-[2-(7-methoxy-1-benzofuran-3-yl)-1-methylethyl)piperazin-1-yl]quinoline ("Compound 37")

6-methyl-8-{4-[2-(7-methoxy-1-benzofuran-3-yl)-1-methylethyl)piperazin-1-yl]quinoline was prepared by generally following the procedure outlined in example 35, step 2, starting from the 1-(7-methoxy-1-benzofuran-3-yl)acetone (204 mg, 1 mmol) and 6-methyl-8-piperazino quinoline (227.0 mg, 1 mmol) in 1,2-dichloroethane (100 ml) and acetic acid (1 ml), sodium triacetoxyborohydride (422 mg, 2 mmol). The product was purified by silica-gel column chromatography by eluting it initially with 80% ethyl acetate:hexane and then with 5% methanol:ethyl acetate, yielding a yellow oil. Yield: 40 mg (9%); (M+H): 416; $^1$HNMR (400 MHz, CDCl$_3$): δ 8.86~8.79 (dd, $J_1$=1.8 Hz, $J_2$=1.8 Hz, 1H), 8.02~7.56 (dd, $J_1$=1.8 Hz, $J_2$=1.8 Hz, 1H), 7.56~6.80 (m, 7 H), 3.89 (s, 3H), 3.50~2.60 (m, 11H); 2.50 (s, 3H) 1.12~114 (d, J=7.0 Hz, 3H).

Example 76

Preparation of 8-{4-[2-(5-methoxy-1-benzofuran-3-yl)-1-methylethyl)piperazin-1-yl]quinoline ("Compound 38")

Step 1: A mixture of 5-methoxy-benzofuran-3 (2H)-one (1.64 g, 10 mmol) and 1-triphenylphosphoranylidene-2-propanone (4.77 g, 15 mmol) was refluxed in toluene (100 ml) for 48 hrs. At the end, reaction mixture was concentrated and loaded over silica-gel column. The column was eluted with hexane (500 ml) and later with 25% ethyl acetate. The product, 1-(5-methoxy-1-benzofuran-3-yl)acetone, was obtained as a red oil. Yield: 1.1 g (53%); (M+H): 205.

Step 2: To a stirred mixture of 1-(5-methoxy-1-benzofuran-3-yl)acetone (204 mg, 1 mmol) and 8-piperazino quinoline (213.0 mg, 1 mmol) in 1,2-dichloroethane (100 ml) and acetic acid (1 ml), sodium triacetoxyborohydride (422 mg, 2 mmol) was added at room temperature. Reaction mixture was stirred at room temperature for 72 hrs. At the end, reaction mixture was neutralized with 10% $NaHCO_3$ and extracted with chloroform. The organic layer was dried over anhydrous $MgSO_4$, filtered and concentrated. The product obtained was purified by silica-gel column chromatography by eluting it initially with 80% ethyl acetate:hexane and then with 5% methanol:ethyl acetate, yielding a brown semi-solid. Yield: 60 mg (14%); (M+H): 402; $^1$HNMR (400 MHz, $CDCl_3$): δ 8.90~8.88 (dd, $J_1$=1.8 Hz, $J_2$=1.8 Hz, 1H); 8.13~8.10 (dd, $J_1$=1.8 Hz, $J_2$=1.8 Hz, 1H); 7.60~6.70 (m, 8H); 3.87 (s, 3H); 3.50~2.50 (m, 11H); 1.15~1.13 (d, J=6.0 Hz, 3H).

Example 77

Preparation of 6-chloro-8-{4-[2-(5-methoxy-1-benzofuran-3-yl)-1-methylethyl)piperazin-1-yl]quinoline ("Compound 39")

6-chloro-8-{4-[2-(5-methoxy-1-benzofuran-3-yl)-1-methylethyl)piperazin-1-yl]quinoline was prepared by generally following the procedure outlined in example 38, step 2, starting from the 1-(5-methoxy-1-benzofuran-3-yl)acetone (204 mg, 1. mmol) and 6-chloro-8-piperazino quinoline (247.0 mg, 1 mmol) in 1,2-dichloroethane (100 ml) and acetic acid (1 ml), sodium triacetoxyborohydride (422 mg, 2 mmol). The product was purified by silica-gel column chromatography by eluting it initially with 80% ethyl acetate:hexane and then with 5% methanol:ethyl acetate, yielding a yellow oil.Yield: 54 mg (12%); (M+H): 436; $^1$HNMR (400 MHz, $CDCl_3$): δe8.82~8.81 (dd, $J_1$=1.8 Hz, $J_2$=1.8 Hz, 1H); 8.02~8.00 (dd, $J_1$=1.8 Hz, $J_2$=1.8 Hz, 1H); 7.99~6.58 (m, 7H); 3.87 (s, 3H); 3.46~2.62 (m, 11H); 1.15~1.13 (d, J=6.0 Hz, 3H).

Example 78

Preparation of 6-methyl-8-{4-[2-(5-methoxy-1-benzofuran-3-yl)-1-methylethyl)piperazin-1-yl]quinoline ("Compound 40")

6-methyl-8-{4-[2-(5-methoxy-1-benzofuran-3-yl)-1-methylethyl)piperazin-1-yl]quinoline was prepared by generally following the procedure outlined in example 38, step 2, starting from the 1-(5-methoxy-1-benzofuran-3-yl)acetone (204 mg, 1 mmol) and 6-methyl-8-piperazino quinoline (227.0 mg, 1 mmol) in 1,2-dichloroethane (100 ml) and acetic acid (1 ml), sodium triacetoxyborohydride (422 mg, 2 mmol). The product was purified by silica-gel column chromatography by eluting it initially with 80% ethyl acetate:hexane and then with 5% methanol:ethyl acetate, yielding a yellow oil. Yield: 62 mg (14%); (M+H): 416; $^1$HNMR (400 MHz, $CDCl_3$): δ☐8.82~8.81 (dd, $J_1$=1.8 Hz, $J_2$=1.8 Hz, 1H); 8.02~8.00 (dd, $J_1$=1.8 Hz, $J_2$=1.8 Hz, 1H); 7.99~6.58 (m, 7H); 3.87 (s, 3H); 3.46~2.62(m, 11H); 2.5 (s, 3H); 1.15~1.13 (d, J=6.0 Hz, 3H).

Example 79

Preparation of 8-{4-[4-cis-(1-benzothien-3-yl)cyclohexyl]-1-piperazinyl}-6-chloroquinoline ("Compound 41")

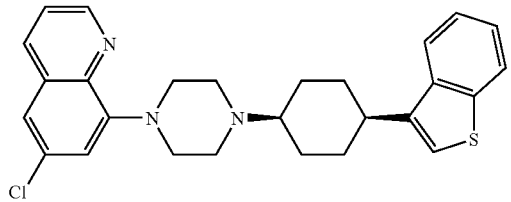

To a solution of 6-chloro-8-piperazino-quinoline (0.280 g) in DCE (10 ml), 4-(3H-inden-1-yl)-cyclohexanone (0.300 g) was added, followed by of sodium triacetoxyborohydride (0.333 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, then 75% ethyl acetate/hexane, to give 0.180 g of the cis product. MP: 164-165° C.; MS (ES) m/z (relative intensity): 463 ($M^+$+H, 100). Elemental analysis for $C_{27}H_{28}ClN_3S$; Calculated: C: 70.19; H: 6.11; N: 9.09; Found: C: 69.87; H: 6.17; N: 8.4.

Example 80

Preparation of 8-{4-[4-trans(1-benzothien-3-yl)cyclohexyl]-1-piperazinyl}-6-chloroquinoline ("Compound 42")

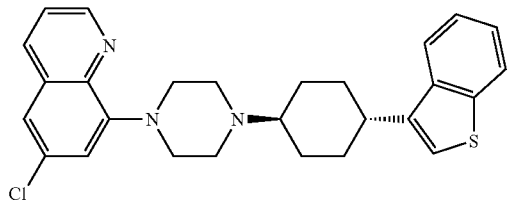

The trans isomer was isolated at the same time as the cis isomer of example 42 above. Off-white solid, 0.100 g; MP: 143-144° C.; MS (ES) m/z (relative intensity): 463 ($M^+$+H, 100). Elemental analysis for $C_{27}H_{28}ClN_3S$; Calculated: C: 70.19; H: 6.11; N: 9.09; Found: C: 69.52; H: 6.31; N: 8.39.

Example 81

Preparation of 8-{4-[4-cis(1-benzothien-3-yl)cyclohexyl]-1-piperazinyl}-6-fluoroquinoline ("Compound 43")

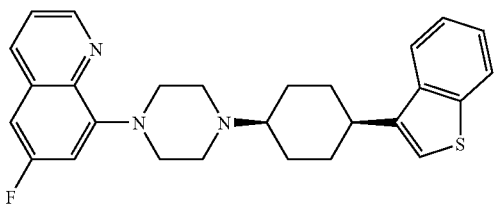

To a solution of 0.200 g of 6-fluoro-8-piperazino-quinoline in DCE (10 ml), was added 0.200 g of 4-(3H-inden-1-yl)-cyclohexanone followed by sodium triacetoxyborohydride (0.230 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 25% ethyl acetate/hexane, then 50% ethyl acetate/hexane, to give 0.130 g of the cis product: MP: 147-151° C.; MS (ES) m/z (relative intensity): 446 ($M^+$+H, 100). Elemental analysis for $C_{27}H_{28}FN_3S$; Calculated: C: 72.78; H: 6.33; N: 9.43; Found: C: 71.69; H: 6.71; N: 6.63.

Example 82

Preparation of 8-{4-[4-trans(1-benzothien-3-yl)cyclohexyl]-1-piperazinyl}-6-fluoroquinoline ("Compound 44")

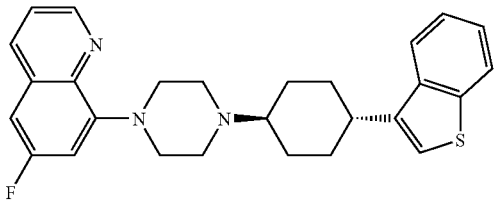

The trans isomer was isolated at the same time as the cis-isomer of example 44, above, as an off-white solid, 0.030 g. MP: 195° C.; MS (ES) m/z (relative intensity): 446 ($M^+$+H, 100). Elemental analysis for $C_{27}H_{28}FN_3S$; Calculated: C: 72.78; H: 6.33; N: 9.43; Found: C: 71.96; H: 6.49; N: 9.

Example 83

Preparation of 8-{4-[4-cis(1-benzothien-3-yl)cyclohexyl]-1-piperazinyl}-6-methoxyquinoline ("Compound 45")

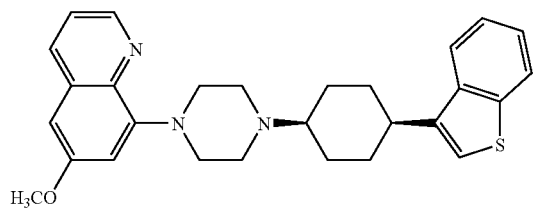

To a solution of 6-methoxy-8-piperazino-quinoline (0.200 g) in DCE (10 ml), 4-(3H-Inden-1-yl)-cyclohexanone (0.200 g) was added, followed by sodium triacetoxyborohydride (0.230 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 25% ethyl acetate/hexane, then 50% ethyl acetate/hexane, to give 0.130 g of the cis product. MP: 148-150° C.; MS (ES) m/z (relative intensity): 458 ($M^+$+H, 100). Elemental analysis for $C_{28}H_{31}N_3OS$; Calculated: C: 73.49; H: 6.83; N: 9.18; Found: C: 73.15; H: 6.9; N: 8.61.

Example 84

Preparation of 8-{4-[4-trans (1-benzothien-3-yl)cyclohexyl]-1-piperazinyl}-6-methoxyquinoline ("Compound 46")

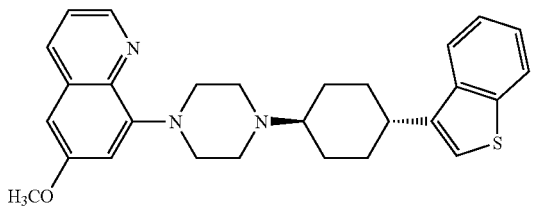

The trans isomer was isolated at the same time as the cis isomer of example 46, above, as an off-white solid, 0.030 g. MP: 166-168° C.; MS (ES) m/z (relative intensity): 458 ($M^+$+H, 100). Elemental analysis for $C_{28}H_{31}N_3OS$; Calculated: C: 73.49; H: 6.83; N: 9.18; Found: C: 71.14; H: 7.36; N: 8.52.

Example 85

Preparation of 6-fluoro-8-{4-[4-cis(5-fluoro-1-benzothien-3-yl)cyclohexyl]piperazin-1-yl}quinoline ("Compound 47")

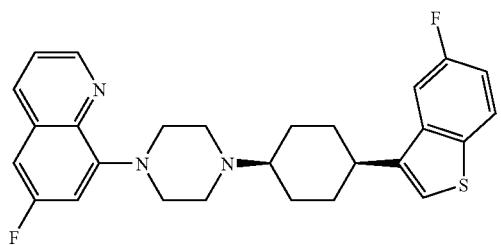

To a solution of 6-fluoro-8-piperazino-quinoline (0.200 g) in DCE (10 ml), 4-(6-fluoro-3H-inden-1-yl)-cyclohexanone (0.200 g) was added, followed by sodium triacetoxyborohydride (0.232 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 30% ethyl acetate/hexane, then 50% ethyl acetate/hexane, to give 0.068 g of the cis product: MS (ES) m/z (relative intensity): 464 ($M^+$+H, 100).

Example 86

Preparation of 6-fluoro-8-{4-[4-trans(5-fluoro-1-benzothien-3-yl)cyclohexyl]piperazin-1-yl}quinoline ("Compound 48")

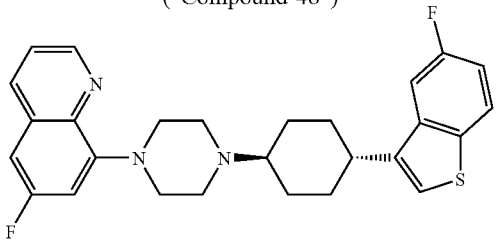

The trans isomer was isolated at the same time as the cis isomer of example 48, above, as an off-white solid, 0.040 g. MP: 143-144° C.; MS (ES) m/z (relative intensity): 464 (M$^+$+H, 100).

Example 87

Preparation of 6-methoxy-8-{4-[4-cis(5-fluoro-1-benzothien-3-yl)cyclohexyl]piperazin-1-yl}quinoline ("Compound 49")

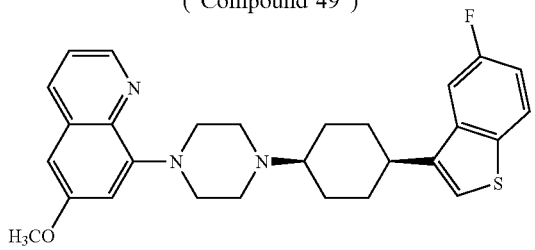

To a solution of 6-methoxy-8-piperazino-quinoline (0.200 g) in DCE (10 ml), 4-(6-fluoro-3H-inden-1-yl)-cyclohexanone (0.200 g) was added, followed by sodium triacetoxyborohydride (0.225 g) and acetic acid (0.2 ml). The reaction was stirred at room temperature overnight. It was quenched with 1N NaOH, and the product was extracted with CH$_2$Cl$_2$. The organic phase was washed with water and dried over magnesium sulfate. The product was filtered through 100 ml of silica gel using 30% ethyl acetate/hexane, 50% ethyl acetate/hexane, and then 100% ethyl acetate to give 0.020 g of the cis product. MS (ES) m/z (relative intensity): 476 (M$^+$+H, 100). Elemental analysis for C$_{28}$H$_{30}$FN$_3$OS; Calculated: C: 70.71; H: 6.36; N: 8.83; Found: C: 69.13; H: 6.31; N: 8.2.

Example 88

Preparation of 6-methoxy-8-{4-[4-trans(5-fluoro-1-benzothien-3-yl)cyclohexyl]piperazin-1-yl}quinoline ("Compound 50")

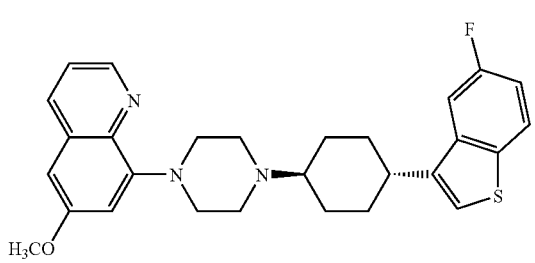

The trans isomer was isolated at the same time as the cis isomer of example 50, above, as an off-white solid, 0.016 g. MS (ES) m/z (relative intensity): 476 (M$^+$+H, 100).

Example 89

Preparation of 5-chloro-8-{4-[4-cis(5-fluoro-1-benzothien-3-yl)cyclohexyl]piperazin-1-yl}quinoline ("Compound 51")

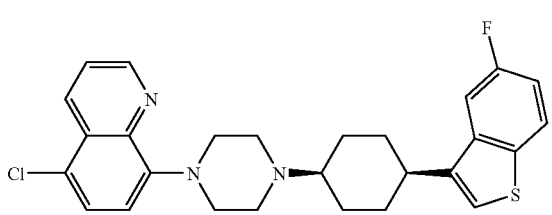

To a solution of 5-chloro-8-piperazino-quinoline (0.254 g) in of DCE (10 ml), was added 4-(6-Fluoro-3H-Inden-1-yl)-cyclohexanone (0.200 g) followed by sodium triacetoxyborohydride (0.274 g) and acetic acid (0.2 ml). The reaction was stirred at room temperature overnight. It was quenched with 1N NaOH, and the product was extracted with CH$_2$Cl$_2$. The organic phase was washed with water and dried over magnesium sulfate. The product was filtered through 100 ml of silica gel using 3:1:1 ethyl acetate/hexane/CH$_2$Cl$_2$ to give 0.050 g of the cis product. MP: 192-197° C.; MS (ES) m/z (relative intensity): 481 (M$^+$+H, 100). Elemental analysis for C$_{27}$H$_{27}$ClFN$_3$S; Calculated: C: 67.56; H: 5.67; N: 8.75; Found: C: 66.29; H: 5.36; N: 7.97.

Example 90

Preparation of 5-chloro-8-{4-[4-trans(5-fluoro-1-benzothien-3-yl)cyclohexyl]piperazin-1-yl}quinoline ("Compound 52")

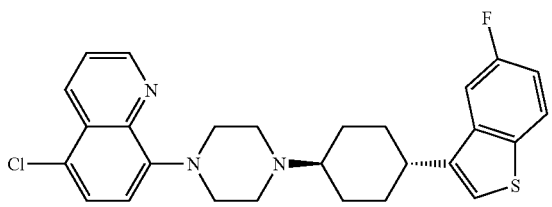

The trans isomer was isolated at the same time as the cis isomer of example 52, above, as an off-white solid, 0.020 g. MP: 195-197° C.; MS (ES) m/z (relative intensity): 481 (M$^+$+H, 100). Elemental analysis for C$_{27}$H$_{27}$ClFN$_3$S; Calculated: C: 67.56; H: 5.67; N: 8.75; Found: C: 66.77; H: 5.6; N: 8.49.

Example 91

Preparation of 8-{4-[4-cis(1-benzofuran-3-yl)cyclohexyl]-1-piperazinyl}-5-fluoroquinoline ("Compound 53")

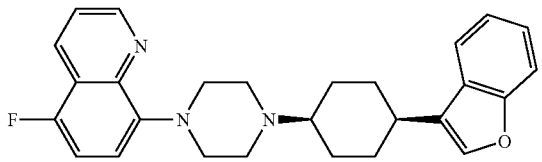

To a solution of 5-fluoro-8-piperazino-quinoline (0.238 g) in of DCE (10 ml), was added 4-benzofuran-3-yl-cyclohexanone (0.200 g) followed by sodium triacetoxyborohydride (0.256 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 75 ml of silica gel using 20% ethyl acetate/hexane, then 50%, to give 0.110 g of the cis product. MP: 142-144° C.; MS (ES) m/z (relative intensity): 430 ($M^+$+H, 100). Elemental analysis for $C_{27}H_{28}FN_3O$; Calculated: C: 75.5; H: 6.57; N: 9.78; Found: C: 75.23; H: 6.69; N: 9.55.

Example 92

Preparation of 8-{4-[4-trans(1-benzofuran-3-yl)cyclohexyl]-1-piperazinyl}-5-fluoroquinoline ("Compound 54")

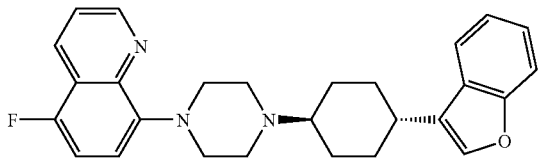

The trans isomer was isolated at the same time as the cis isomer of example 54, above, as an off-white solid, 0.025 g. MP: 162-164° C.; MS (ES) m/z (relative intensity): 430 ($M^+$+H, 100). Elemental analysis for $C_{27}H_{28}FN_3O$; Calculated: C: 75.5; H: 6.57; N: 9.78; Found: C: 75.06; H: 7.1; N: 9.47.

Example 93

Preparation of 8-{4-[4-cis(1-benzofuran-3-yl)cyclohexyl]-1-piperazinyl}-6-fluoroquinoline ("Compound 55")

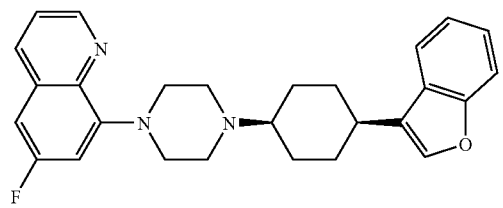

To a solution of 6-fluoro-8-piperazino-quinoline (0.130 g) in DCE (10 ml), was added 4-benzofuran-3-yl-cyclohexanone (0.200 g) followed by sodium triacetoxyborohydride (0.166 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 20% ethyl acetate/hexane, then 50%, to give 0.050 g of the cis product. MS (ES) m/z (relative intensity): 430 ($M^+$+H, 100). Elemental analysis for $C_{27}H_{28}FN_3O$; Calculated: C: 75.5; H: 6.57; N: 9.78; Found: C: 73.83; H: 7.29; N: 9.35.

Example 94

Preparation of 8-{4-[4-trans(1-benzofuran-3-yl)cyclohexyl]-1-piperazinyl}-6-fluoroquinoline ("Compound 56")

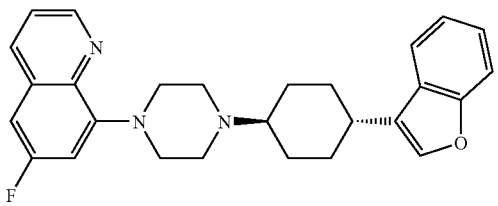

The trans isomer was isolated at the same time as the cis isomer of example 56, above, as an off-white solid, 0.020 g. MP: 195-197°; MS (ES) m/z (relative intensity): 430 ($M^+$+H, 100). Elemental analysis for $C_{27}H_{28}FN_3O$; Calculated: C: 75.5; H: 6.57; N: 9.78; Found: C: 74.75; H: 6.87; N: 9.62.

Example 95

Preparation of 5-fluoro-8-{4-[4-cis(7-methoxy-1-benzofuran-3-yl)cyclohexyl]-1-piperazinyl}quinoline ("Compound 57")

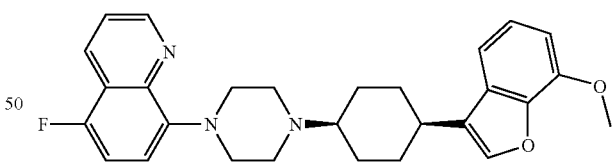

To a solution of 5-fluoro-8-piperazino-quinoline (0.200 g) in DCE (10 ml), was added 4-(7-Mehtoxy-Benzofuran-3-yl)-cyclohexanone (0.184 g) followed by sodium triacetoxyborohydride (0.230 g) and acetic acid (0.1 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 25% ethyl acetate/hexane, then 50% ethyl acetate/hexane, to give 0.025 g of the cis product. MP: 143-146° C.; MS (ES) m/z (relative intensity): 460 ($M^{+30\ H}$, 100). Elemental analysis for $C_{28}H_{30}FN_3O_2$; Calculated: C: 73.18; H: 6.58; N: 9.14; Found: C: 71.95; H: 6.49; N: 8.81.

Example 96

Preparation of 5-fluoro-8-{4-[4-trans(7-methoxy-1-benzofuran-3-yl)cyclohexyl]-1-piperazinyl}quinoline ("Compound 58")

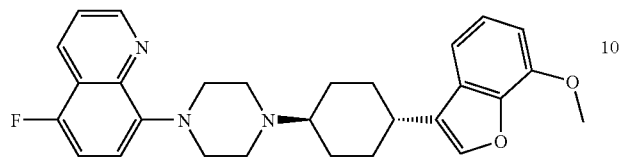

The trans isomer was isolated at the same time as the cis isomer of example 58, above, as an off-white solid, 0.010 g. MS (ES) m/z (relative intensity): 460 (M⁺+H, 100).

Example 97

Preparation of 6-fluoro-8-{4-[4-cis(7-methoxy-1-benzofuran-3-yl)cyclohexyl]-1-piperazinyl}quinoline ("Compound 59")

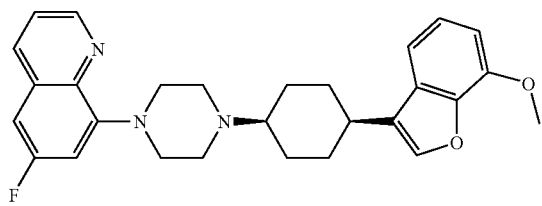

To a solution of 6-fluoro-8-piperazino-quinoline (0.200 g) in DCE (10 ml), was added 4-(7-methoxy-benzofuran-3-yl)-cyclohexanone (0.200 g) followed by sodium triacetoxyborohydride (0.230 g) and acetic acid (0.1 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 30% ethyl acetate/hexane, then 50% ethyl acetate/hexane, to give 0.065 g of the cis product. MP: 75-83° C.; MS (ES) m/z (relative intensity): 460 (M⁺³⁰ ᴴ, 100). Elemental analysis for $C_{28}H_{30}FN_3O_2$; Calculated: C: 73.18; H: 6.58; N: 9.14; Found: C: 72.26; H: 6.61; N: 8.67.

Example 98

Preparation of 6-fluoro-8-{4-[4-trans(7-methoxy-1-benzofuran-3-yl)cyclohexyl]-1-piperazinyl}quinoline ("Compound 60")

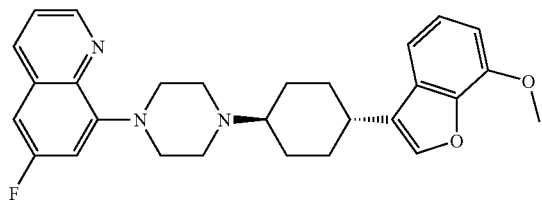

The trans isomer was isolated at the same time as the cis isomer of example 60, above, as an off white solid, 0.029 g. MP: 195-197° C.; MS (ES) m/z (relative intensity): 460 (M⁺+H, 100). Elemental analysis for $C_{28}H_{30}FN_3O_2$; Calculated: C: 73.18; H: 6.58; N: 9.14; Found: C: 72.47; H: 6.4; N: 8.84.

Example 99

Preparation of 8-{4-[4-cis(7-methoxy-1-benzofuran-3-yl)cyclohexyl]-1-piperazinyl}quinoline ("Compound 61")

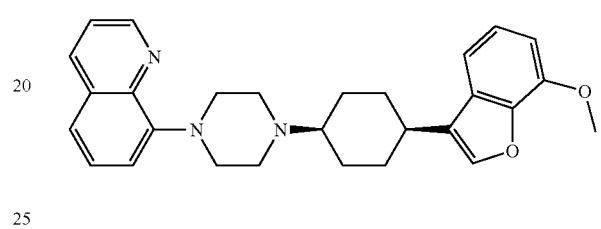

To a solution of 8-piperazino-quinoline (0.350 g) in DCE (10 ml), was added 4-(7-Methoxy-Benzofuran-3-yl)-cyclohexanone (0.200 g) followed by sodium triacetoxyborohydride (0.300 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, to give 0.105 g of the cis product. MP: 66-67° C.; MS (ES) m/z (relative intensity): 442 (M⁺+H, 100). Elemental analysis for $C_{28}H_{31}N_3O2$; Calculated: C: 76.16; H: 7.08; N: 9.52; Found: C: 74.8; H: 7.14; N: 8.88.

Example 100

Preparation of 8-{4-[4-trans(7-methoxy-1-benzofuran-3-yl)cyclohexyl]-1-piperazinyl}quinoline ("Compound 62")

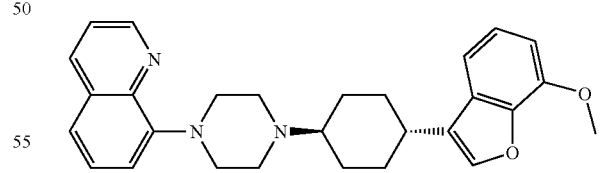

The trans isomer was isolated at the same time as the cis isomer of example 62, above, as an off white solid, 0.015 g. MP: 195-197° C.; MS (ES) m/z (relative intensity): 442 (M⁺+H, 100). Elemental analysis for $C_{28}H_{31}N_3O_2$; Calculated: C: 76.16; H: 7.08; N: 9.52; Found: C: 74.9; H: 7.02; N: 8.98.

Example 101

Preparation of 5-chloro-8-{4-[4-cis(7-methoxy-1-benzofuran-3-yl)cyclohexyl]piperazin-1-yl}quinoline ("Compound 63")

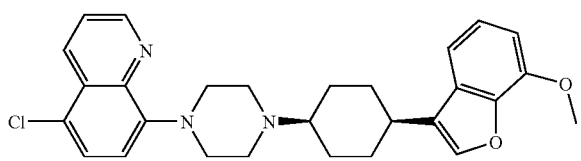

To a solution of 5-chloro-8-piperazino-quinoline (0.200 g) in DCE (10 ml), was added 4-(7-methoxy-benzofuran-3-yl)-cyclohexanone (0.200 g) followed by sodium triacetoxyborohydride (0.224 g) and acetic acid (0.1 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, then 70% ethyl acetate/hexane, to give 0.035 g of the cis product. MS (ES) m/z (relative intensity): 477 ($M^+$+H, 100).

Example 102

Preparation of 5-chloro-8-{4-[4-trans(7-methoxy-1-benzofuran-3-yl)cyclohexyl]piperazin-1-yl}quinoline ("Compound 64")

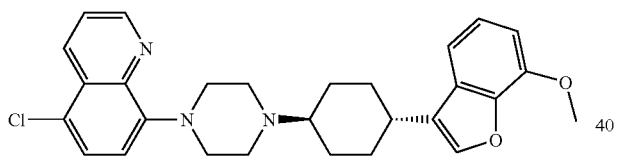

The trans isomer was isolated at the same time as the cis isomer of example 64, above, as an off white solid, 0.010 g. MS (ES) m/z (relative intensity): 477 ($M^+$+H, 100).

Example 103

Preparation of 5-chloro-8-{4-[4-cis(5-methoxy-1-benzofuran-3-yl)cyclohexyl]piperazin-1-yl}quinoline ("Compound 65")

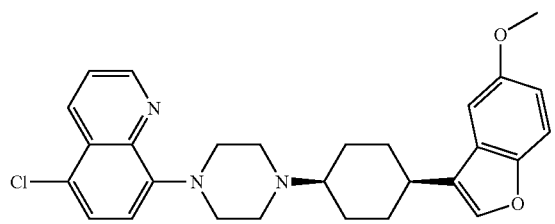

To a solution of 5-chloro-8-piperazino-quinoline (0.200 g) in DCE (10 ml), was added 4-(7-methoxy-benzofuran-3-yl)-cyclohexanone (0.200 g) followed by sodium triacetoxyborohydride (0.224 g) and acetic acid (0.1 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, 75% ethyl acetate/hexane, and finally 100% ethyl acetate to give 0.015 g of the is product. MS (ES) m/z (relative intensity): 477 ($M^+$+H, 100).

Example 104

Preparation of 5-chloro-8-{4-[4-trans(5-methoxy-1-benzofuran-3-yl)cyclohexyl]piperazin-1-yl}quinoline ("Compound 66")

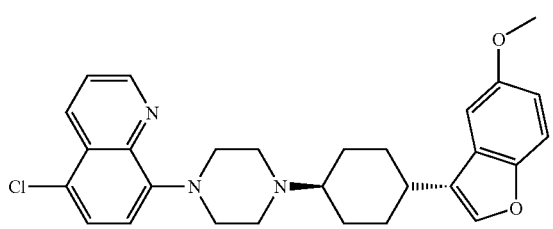

The trans isomer was isolated at the same time as the cis isomer of example 66, above, as an off-white solid, 0.012 g. MS (ES) m/z (relative intensity): 477 ($M^+$+H, 100).

Example 105

Preparation of 6-fluoro-8-{4-[4-cis(5-methoxy-1-benzofuran-3-yl)cyclohexyl]piperazin-1-yl}quinoline ("Compound 67")

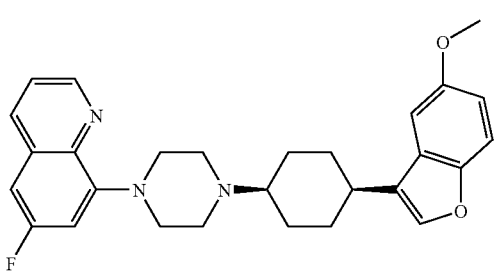

To a solution of 6-fluoro-8-piperazino-quinoline (0.300 g) in DCE (10 ml), was added 4-(7-methoxy-benzofuran-3-yl)-cyclohexanone (0.300 g) followed by of sodium triacetoxyborohydride (0.345 g) and acetic acid (0.2 ml). The reaction was stirred at room temperature overnight. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, to give 0.050 g of the cis product. MP: 153-160° C.; MS (ES) m/z (relative intensity): 460 ($M^+$+H, 100). Elemental analysis for $C_{28}H_{30}FN_3O_2$; Calculated: C: 73.18; H: 6.58; N: 9.14; Found: C: 71.86; H: 6.86; N: 8.73.

Example 106

Preparation of 6-fluoro-8-{4-[4-trans(5-methoxy-1-benzofuran-3-yl)cyclohexyl]piperazin-1-yl}quinoline ("Compound 68")

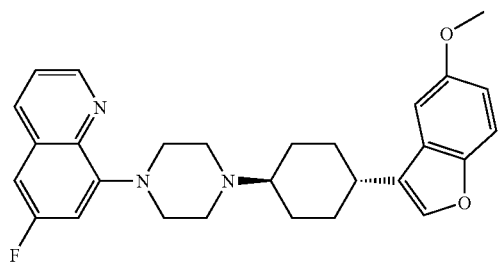

The trans isomer was isolated at the same time as the cis isomer of example 68, above, as an off-white solid (0.030 g). MP: 152-155° C. MS (ES) m/z (relative intensity): 460 (M$^+$+H, 100). Elemental analysis for $C_{28}H_{30}ClN_3O_2$; Calculated: C: 73.18; H: 6.58; N: 9.14; Found: C: 71.96; H: 6.64; N: 8.46.

Example 107

Preparation of 8-[4-(4-benzofuran-2-yl-yclohexyl)-piperazin-1-yl]-6-fluoro-quinoline ("Compound 69")

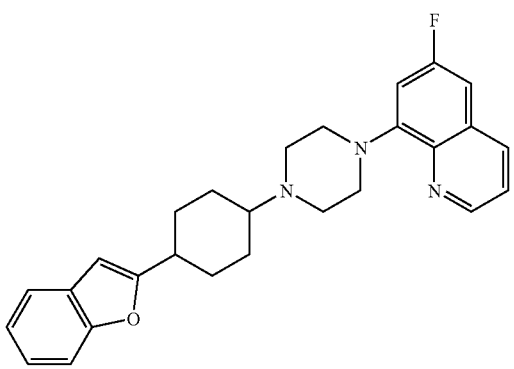

To a solution of 6-fluoro-8-piperazino-quinoline (1.4 g) in DCE (50 ml), was added 4-benzofuran-2-yl-cyclohexanone (0.960 g) followed by sodium triacetoxyborohydride (1.6 g) and acetic acid (2 ml). The reaction was stirred at room temperature for 6 hours. It was quenched with 1N NaOH, and the product was extracted with $CH_2Cl_2$. The organic phase was washed with water and dried over magnesium sulfate. The product was filtered through 100 ml of silica gel using 50% ethyl acetate/hexane, to give 0.050 g of the cis product. MP 91-93° C.; MS (ES) m/z (relative intensity): 430 (M$^+$+H, 100).

Example 108

Preparation of cis-8-[4-(4-thiophene-2-yl-cyclohexyl)-piperazin-1-yl]-6-methoxy-quinoline ("Compound 70")

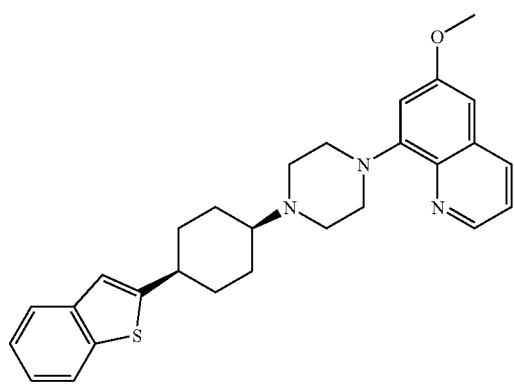

A solution of 4-benzo[b]thiophen-2-yl-cyclohexanone (237 mg, 1 mmol), 6-methoxy-8-piperazin-(250 mg, 1 mmol), Na(OAc)$_3$BH (327 mg, 1.55 mmol) and HOAc (0.12 ml, 2 mmol) in ClCH$_2$CH$_2$Cl (40 ml) was stirred at room temperature overnight. The reaction mixture was quenched with 1 N aqueous NaOH (50 ml) and poured into H$_2$O (50 ml), and extracted into CH$_2$Cl$_2$ (1×100 ml) and EtOAc (2×100 ml). The organic phases were combined, dried over Na$_2$SO$_4$ and concentrated under vacuum. Flash chromatogroaphy on silica gel (5% methanol/ethylacetate) afforded a yellow solid which was one spot by TLC. Analytical HPLC indicated an 80:20 mixture of cis and trans isomers. Preparative HPLC (Primesphere silica column, 50×250 mm, 50/50 hexane/methyl t-butyl ether) afforded 130 mg (28%) of the cis isomer (first eluting) compound as a pale yellow crystalline solid. MP: 184-186° C. MS (ES) m/z (relative intensity): 458 (M$^+$+H, 100). Elemental Analysis for $C_{28}H_{31}N_3OS$; Calculated: C, 73.49; H, 6.83; N, 9.18; Found: C, 73.19; H, 6.93; N, 9.03.

Example 109

Preparation of trans-8-[4-(4-thiophene-2-yl-cyclohexyl)-piperazin-1-yl]-6-methoxy-quinoline ("Compound 71")

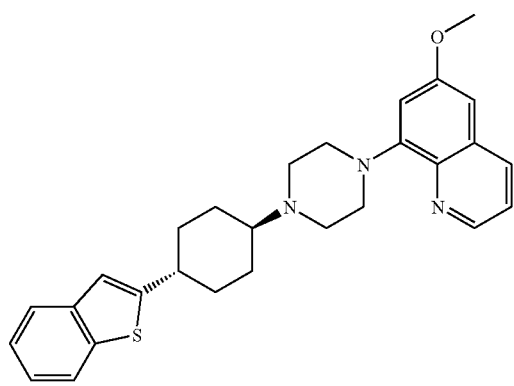

The trans isomer was isolated at the same time as the cis isomer of example 71, above, as an off-white solid. MP: 193-194° C.; MS (ES) m/z (relative intensity): 458 (M⁺+H, 100). Elemental Analysis for $C_{28}H_{31}N_3OS.0.5H_2O$; Calculated: C, 72.07; H, 6.91; N, 9.00; Found: C, 72.23; H, 6.88; N, 8.96.

Example 110

Testing Affinity of Compounds for 5-HT Transporter

The 5-HT transporter affinity of the compounds of this invention was established in accordance with standard pharmaceutically accepted test procedures with representative compounds as follows.

Rat Brain ³H-Paroxetine Binding Assay (RB 5HT Transporter):

This assay was used to determine a compound's affinity of the 5-HT transporter.

A protocol similar to that used by Cheetham et al. (Neuropharmacol., 1993, 32: 737) was used. Briefly, frontal cortical membranes prepared from male S.D. rats were incubated with ³H-parxetine (0.1 nM) for 60 min at 25° C. All tubes also contained either vehicle, test compound (one to eight concentrations), or a saturating concentration of fluoxetine (10 µM) to define specific binding. All reactions were terminated by the addition of ice cold Tris buffer followed by rapid filtration using a Tom Tech filtration device to separate bound from free ³H-paroxetine. Bound radioactivity was quantitated using a Wallac 1205 Beta Plate® counter. Nonlinear regression analysis was used to determine $IC_{50}$ values which were converted to $K_i$ values using the method of Cheng and Prusoff (Biochem. Pharmacol., 1973, 22: 3099).

$K_i=IC_{50}/\text{Radioligand concentration}/(1+KD)$

Inhibition of ³H-5-HT Uptake by Cells Possessing the Human 5-HT Transporter (HC 5HT Transporter)

A human carcinoma cell line (Jar cells) possessing low endogenous levels of the 5-HT-transporter are seeded into 96 well plates and treated with staurosporine at least 18 hrs prior to assay. [Staurosporine greatly increases the expression of the 5-HT-transporter.] On the day of assay, vehicle, excess fluoxetine, or test compound was added to various wells on the plate. All wells then received ³H-5-HT and were incubated at 37° C. for 5 min. The wells were then washed with ice cold 50 mM Tris HCl (pH 7.4) buffer and aspirated to remove free ³H-5-HT. 25 µl of 0.25 M NaOH was then added to each well to lyse the cells and 75 µl scintillation cocktail (Microscint™ 20) was added prior to quantitation on a Packard TopCount machine. Tubes with vehicle represent total possible uptake, radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine $IC_{50}$ values. If the compound is active at inhibiting 5-HT uptake, its counts will be close to that obtained with fluoxetine.

High affinity for the serotonin 5-HT$_{1A}$ receptor was established by testing the claimed compound's ability to displace [³H] 8-OH-DPAT (dipropylaminotetralin) from the 5-HT$_{1A}$ serotonin receptor following a modification of the procedure of Hall et al.(J. Neurochem., 1985, 44: 1685), which utilizes CHO cells stably transfected with human 5-HT1A receptors. The 5-HT$_{1A}$ affinities for the compounds of the invention are reported below as $K_i$'s.

Antagonist activity at 5-HT$_{1A}$ receptors was established by using a ³⁵S-GTPγS binding assay similar to that used by Lazareno and Birdsall (Br. J. Pharmacol., 1993, 109: 1120), in which the test compound's ability to affect the binding of ³⁵S-GTPγS to membranes containing cloned human 5-HT$_{1A}$ receptors was determined. Agonists produce an increase in binding whereas antagonists produce no increase but rather reverse the effects of the standard agonist 8-OH-DPAT. The test compound's maximum inhibitory effect is represented as the $I_{max}$, while its potency is defined by the $IC_{50}$.

Results from these two assays are presented below in Table I.

TABLE 1

| Compound | 5-HT$_{1A}$ $K_i$ (nM) | RB-5HT Transporter $K_i$ (nM) | HC-5HTC Transporter $K_i$(nM) |
|---|---|---|---|
| 1 | 1.94 | 6.50 | 25.30 |
| 2 | 124.20 | 176 | 1710 |
| 3 | 1.93 | 14.00 | 75.60 |
| 4 | 2.48 | 60.00 | 612 |
| 5 | 0.73 | 31.00 | 1.6 |
| 6 | 16.14 | 471 | 1080 |
| 7 | 15.37 | 32%* | 2150 |
| 8 | 36.72 | 403 | 1780 |
| 9 | 0.37 | 33 | 71.30 |
| 10 | 0.94 | 97.00 | 206 |
| 11 | 0.81 | 37 | 540 |
| 12 | 2.92 | 11 | 42.20 |
| 13 | 41.34 | 64 | 270 |
| 14 | 13.48 | 45 | 9.82 |
| 15 | 0.37 | 17 | 67.20 |
| 16 | 8.05 | 62.00 | 180 |
| 17 | 1.59 | 16.50 | 50.90 |
| 18 | 0.11 | 0.65 | 9.46 |
| 19 | Not tested | Not tested | Not tested |
| 20 | 0.14 | 3.79 | 47.70 |
| 21 | 2.83 | 7.25 | 43.65 |
| 22 | 2.69 | 2.00 | 106 |
| 23 | 19.97 | 28.50 | 182.50 |
| 24 | 46%* | 24%* | 3730 |
| 25 | 8.71 | 47.00 | 210.00 |
| 26 | 14.37 | 16.50 | 51.05 |
| 27 | 19.35 | 32.00 | 51.90 |
| 28 | 109.90 | 73.00 | 125.00 |
| 29 | 112.44 | 68.00 | 115.00 |
| 30 | 79.07 | 93.00 | 347.00 |
| 31 | 0.91 | 4.17 | 9.53 |
| 32 | 2.16 | 35.00 | 58.20 |
| 33 | 8.19 | 58.00 | 183.0 |
| 34 | 9.13 | 35.00 | 881 |
| 35 | 1.22 | 119.00 | 1000 |
| 36 | 0.23 | 4.16 | 31.00 |
| 37 | Not Tested | 471.00 | Not Tested |
| 38 | 0.14 | 14.00 | 59.50 |
| 39 | 0.34 | 5.50 | 40.10 |
| 40 | 1.77 | 130.0 | 549.00 |
| 41 | 2.25 | 65.00 | 338.00 |
| 42 | 140.5 | 157.00 | 184.00 |
| 43 | 1.17 | 311.0 | 1440.00 |
| 44 | 130.45 | 380.00 | 1620.00 |
| 45 | 1.73 | 259.00 | 1080.00 |
| 46 | 126.20 | 21.00 | 802.00 |
| 47 | 1.72 | 25%* | 3490.00 |
| 48 | 0.28 | 155.00 | 739.00 |
| 49 | 1.37 | 92.00 | 659.00 |
| 50 | 25.94 | 10.00 | 65.30 |
| 51 | 4.14 | 133.00 | 1150.00 |
| 52 | 42%* | 48.00 | 751.00 |

TABLE 1-continued

| Compound | 5-HT$_{1A}$ K$_i$ (nM) | RB-5HT Transporter K$_i$ (nM) | HC-5HTC Transporter K$_i$ (nM) |
|---|---|---|---|
| 53 | 1.74 | 208.00 | 3910.00 |
| 54 | 25.09 | 38.00 | 220.00 |
| 55 | 0.11 | 116.00 | 471.50 |
| 56 | 16.58 | 77.00 | 337.00 |
| 57 | 0.40 | 163.00 | 3040.00 |
| 58 | 21.06 | 34.00 | 272.00 |
| 59 | 1.93 | 48.00 | 455.00 |
| 60 | 0.16 | 50.00 | 212.00 |
| 61 | 41.37 | 27.00 | 96.80 |
| 62 | 0.26 | 46.00 | 38.00 |
| 63 | 0.92 | 87.00 | 124.00 |
| 64 | 18.69 | 49.00 | 176.20 |
| 65 | 10.12 | 53.00 | 53.00 |
| 66 | 1.99 | 89.00 | 1200.00 |
| 67 | 14.37 | 146.00 | 1200.00 |
| 68 | 0.22 | 121.00 | 3290.00 |
| 69 | 16.32 | 106 | Not tested |
| 70 | 1547 | 47 | 3000 |
| 71 | 162 | Not tested | Not tested |

*% inhibition @ 1 μM concentration.

Hence, the compounds of this invention not only inhibit or block serotonin reuptake (thereby increasing levels of serotonin in the synapse) but also antagonize the 5-HT$_{1A}$ receptors (thereby reducing the latency period). The compounds of the invention would thus be useful in the prevention and/or treatment of diseases affected by disorders of the serotonin affected neurological systems, including depression, anxiety, cognitive deficits, such as those resulting from Alzheimer's disease and other neurodegenerative disorders, schizophrenia, prostate cancer, and nicotine withdrawal, by administration orally, parenterally, or by aspiration to a patient in need thereof.

When ranges are used herein for physical properties, such as molecular weight, or chemical properties, such as chemical formulae, all combinations and subcombinations of ranges specific embodiments therein are intended to be included.

The disclosures of each patent, patent application, and publication cited or described in this document are herby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound selected from the group consisting of:
8-{4-[2-(1-benzofuran-3-yl)ethyl]-1-piperazinyl}-6-fluoroquinoline;
8-{4-[2-(1-benzofuran-3-yl)ethyl]-1-piperazinyl}-6-chloroquinoline;
8-{4-[2-(1-benzofuran-3-yl)ethyl]-1-piperazinyl}-6-methylquinoline;
8-{4-[2-(1-benzofuran-3-yl)ethyl]-1-piperazinyl}-6-methoxyquinoline;
8-{4-[2-(6-chloro-1-benzofuran-3-yl)ethyl]-1-piperazinyl}-quinoline;
8-{4-[2-(6-chloro-1-benzofuran-3-yl)ethyl]-1-piperazinyl}-6-fluoro-quinoline;
8-{4-[2-(6-chloro-1-benzofuran-3-yl)ethyl]-1-piperazinyl}-6-chloro-quinoline;
8-{4-[2-(6-chloro-1-benzofuran-3-yl)ethyl]-1-piperazinyl}-6-methyl-quinoline;
8-{4-[2-(6-methoxy-1-benzofuran-3-yl)ethyl]-1-piperazinyl}-quinoline;
8-{4-[2-(6-methoxy-1-benzofuran-3-yl)ethyl]-1-piperazinyl}-6-methyl-quinoline;
8-{4-[2-(6-methoxy-1-benzofuran-3-yl)ethyl]-1-piperazinyl}-6-chloro-quinoline;
8-{4-[2-(5-chloro-1-benzofuran-3-yl)ethyl]-1-piperazinyl}-quinoline;
8-{4-[2-(5-chloro-1-benzofuran-3-yl)ethyl]-1-piperazinyl}-6-chloro-quinoline;
8-{4-[2-(5-chloro-1-benzofuran-3-yl)ethyl]-1-piperazinyl}-6-methyl-quinoline;
8-{4-[2-(5-fluoro-1-benzofuran-3-yl)ethyl]-1-piperazinyl}-quinoline;
8-{4-[2-(5-fluoro-1-benzofuran-3-yl)ethyl]-1-piperazinyl}-6-methoxy-quinoline;
8-{4-[2-(5-fluoro-1-benzofuran-3-yl)ethyl]-1-piperazinyl}-6-fluoro-quinoline;
8-{4-[2-(7-methoxy-1-benzofuran-3-yl)ethyl]-1-piperazinyl}-quinoline;
8-{4-[2-(7-methoxy-1-benzofuran-3-yl)ethyl]-1-piperazinyl}-6-methoxy-quinoline;
8-{4-[2-(7-methoxy-1-benzofuran-3-yl)ethyl]-1-piperazinyl}-6-chloro-quinoline;
8-{4-[2-(5-methoxy-1-benzofuran-3-yl)ethyl]-1-piperazinyl}-quinoline;
8-{4-[2-(5-methoxy-1-benzofuran-3-yl)ethyl]-1-piperazinyl}-6-chloro-quinoline;
8-{4-[2-(5-methoxy-1-benzofuran-3-yl)ethyl]-1-piperazinyl}-6-methyl-quinoline;
8-{4-[2-(5-methoxy-1-benzofuran-3-yl)ethyl]-1-piperazinyl}-6-isopropyl-quinoline;
8-{4-[2-(5-methoxy-1-benzofuran-3-yl)ethyl]-1-piperazinyl}-6-methoxy-quinoline;
8-{4-[2-(5-methoxy-1-benzofuran-3-yl)ethyl]-1-piperazinyl}-6-fluoro-quinoline;
8-{4-[2-(1-benzofuran-3-yl)propyl]-1-piperazinyl}quinoline;
8-{4-[2-(1-benzofuran-3-yl)propyl]-1-piperazinyl}-6-chloro-quinoline;
8-{4-[2-(1-benzofuran-3-yl)propyl]-1-piperazinyl}-6-fluoro-quinoline;
8-{4-[2-(1-benzofuran-3-yl)propyl]-1-piperazinyl}-6-methyl-quinoline;
8-{4-[2-(7-methoxy-1-benzofuran-3-yl)propyl]-1-piperazinyl}quinoline;
8-{4-[2-(7-methoxy-1-benzofuran-3-yl)propyl]-1-piperazinyl}-6-methyl-quinoline;
8-{4-[2-(7-methoxy-1-benzofuran-3-yl)propyl]-1-piperazinyl}-6-chloro-quinoline;
8-{4-[2-(7-methoxy-1-benzofuran-3-yl)propyl]-1-piperazinyl}-6-methyl-quinoline;
8-{4-[2-(7-methoxy-1-benzofuran-3-yl)-1-methylethyl)piperazin-1-yl]quinoline;
6-methoxy-8-{4-[2-(7-methoxy-1-benzofuran-3-yl)-1-methylethyl)piperazin-1-yl]quinoline;
6-methyl-8-{4-[2-(7-methoxy-1-benzofuran-3-yl)-1-methylethyl)piperazin-1-yl]quinoline;
8-{4-[2-(5-methoxy-1-benzofuran-3-yl)-1-methylethyl)piperazin-1-yl]quinoline;
6-chloro-8-{4-[2-(5-methoxy-1-benzofuran-3-yl)-1-methylethyl)piperazin-1-yl]quinoline;
6-methyl-8-{4-[2-(5-methoxy-1-benzofuran-3-yl)-1-methylethyl)piperazin-1-yl]quinoline;

8-{4-[4-cis-(1-benzothien-3-yl)cyclohexyl]-1-piperazinyl}-6-chloroquinoline;
8-{4-[4-trans(1-benzothien-3-yl)cyclohexyl]-1-piperazinyl}-6-chloroquinoline;
8-{4-[4-cis(1-benzothien-3-yl)cyclohexyl]-1-piperazinyl}-6-fluoroquinoline;
8-{4-[4-trans(1-benzothien-3-yl)cyclohexyl]-1-piperazinyl}-6-fluoroquinoline;
8-{4-[4-cis(1-benzothien-3-yl)cyclohexyl]-1-piperazinyl}-6-methoxyquinoline;
8-{4-[4-trans (1-benzothien-3-yl)cyclohexyl]-1-piperazinyl}-6-methoxyquinoline;
6-fluoro-8-{4-[4-cis(5-fluoro-1-benzothien-3-yl)cyclohexyl]piperazin-1-yl}quinoline;
6-fluoro-8-{4-[4-trans(5-fluoro-1-benzothien-3-yl)cyclohexyl]piperazin-1-yl}quinoline;
6-methoxy-8-{4-[4-cis(5-fluoro-1-benzothien-3-yl)cyclohexyl]piperazin-1-yl}quinoline;
6-methoxy-8-{4-[4-trans(5-fluoro-1-benzothien-3-yl)cyclohexyl]piperazin-1-yl}quinoline;
5-chloro-8-{4-[4-cis(5-fluoro-1-benzothien-3-yl)cyclohexyl]piperazin-1-yl}quinoline;
5-chloro-8-{4-[4-trans(5-fluoro-1-benzothien-3-yl)cyclohexyl]piperazin-1-yl}quinoline;
8-{4-[4-cis(1-benzofuran-3-yl)cyclohexyl]-1-piperazinyl}-5-fluoroquinoline;
8-{4-[4-trans(1-benzofuran-3-yl)cyclohexyl]-1-piperazinyl}-5-fluoroquinoline;
8-{4-[4-cis(1-benzofuran-3-yl)cyclohexyl]-1-piperazinyl}-6-fluoroquinoline;
8-{4-[4-trans(1-benzofuran-3-yl)cyclohexyl]-1-piperazinyl}-6-fluoroquinoline;
5-fluoro-8-{4-[4-cis(7-methoxy-1-benzofuran-3-yl)cyclohexyl]-1-piperazinyl}quinoline;
5-fluoro-8-{4-[4-trans(7-methoxy-1-benzofuran-3-yl)cyclohexyl]-1-piperazinyl}quinoline;
6-fluoro-8-{4-[4-cis(7-methoxy-1-benzofuran-3-yl)cyclohexyl]-1-piperazinyl}quinoline;
6-fluoro-8-{4-[4-trans(7-methoxy-1-benzofuran-3-yl)cyclohexyl]-1-piperazinyl}quinoline;
8-{4-[4-cis(7-methoxy-1-benzofuran-3-yl)cyclohexyl]-1-piperazinyl}quinoline;
8-{4-[4-trans(7-methoxy-1-benzofuran-3-yl)cyclohexyl]-1-piperazinyl}quinoline;
5-chloro-8-{4-[4-cis(7-methoxy-1-benzofuran-3-yl)cyclohexyl]piperazin-1-yl}quinoline;
5-chloro-8-{4-[4-trans(7-methoxy-1-benzofuran-3-yl)cyclohexyl]piperazin-1-yl}quinoline;
5-chloro-8-{4-[4-cis(5-methoxy-1-benzofuran-3-yl)cyclohexyl]piperazin-1-yl}quinoline;
5-chloro-8-{4-[4-trans(5-methoxy-1-benzofuran-3-yl)cyclohexyl]piperazin-1-yl}quinoline;
6-fluoro-8-{4-[4-cis(5-methoxy-1-benzofuran-3-yl)cyclohexyl]piperazin-1-yl}quinoline;
6-fluoro-8-{4-[4-trans(5-methoxy-1-benzofuran-3-yl)cyclohexyl]piperazin-1-yl}quinoline;
8-[4-(4-benzofuran-2-yl-yclohexyl)-piperazin-1-yl]-6-fluoro-quinoline; and pharmaceutically acceptable salts thereof.

\* \* \* \* \*